(12) United States Patent
Feurer et al.

(10) Patent No.: US 7,737,153 B2
(45) Date of Patent: Jun. 15, 2010

(54) HETEROARYLOXY-SUBSTITUTED PHENYLAMINOPYRIMIDINES AS RHO-KINASE INHIBITORS

(75) Inventors: Achim Feurer, Wilhelmsfeld (DE); Samir Bennabi, Lyons (FR); Heike Heckroth, Wuppertal (DE); Hartmut Schirok, Wuppertal (DE); Joachim Mittendorf, Wuppertal (DE); Raimund Kast, Wuppertal (DE); Johannes-Peter Stasch, Solingen (DE); Jean Mark Gnoth, Mettmann (DE); Klaus Münter, Wülfrath (DE); Dieter Lang, Velbert (DE); Santiago Figueroa Perez, Leverkusen (DE); Heimo Ehmke, Hamburg (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 19 days.

(21) Appl. No.: 10/531,889

(22) PCT Filed: Oct. 16, 2003

(86) PCT No.: PCT/EP03/11452

§ 371 (c)(1),
(2), (4) Date: Jun. 5, 2006

(87) PCT Pub. No.: WO2004/039796

PCT Pub. Date: May 13, 2004

(65) Prior Publication Data

US 2006/0241127 A1 Oct. 26, 2006

(30) Foreign Application Priority Data

Oct. 28, 2002 (DE) .................... 102 50 113
Jul. 16, 2003 (DE) .................... 103 32 232

(51) Int. Cl.
| A01N 43/90 | (2006.01) |
| A61K 31/519 | (2006.01) |
| A61K 31/505 | (2006.01) |
| C07D 487/00 | (2006.01) |
| C07D 239/02 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |

(52) U.S. Cl. ............... 514/259.1; 514/269; 514/275; 544/281; 544/314; 544/324

(58) Field of Classification Search .................. None
See application file for complete search history.

(56) References Cited

FOREIGN PATENT DOCUMENTS

| WO | WO0153331 | * | 7/2001 |
| WO | 0160816 |   | 8/2001 |
| WO | 0164654 |   | 9/2001 |

OTHER PUBLICATIONS

U.S. Appl. No. 11/547,975, filed Oct. 2006, Schirock et al.*
Jul. 2007. http://www.thomsonhc.com/pdrel/librarian/PFDefaultActionId/pdrcommon.Stedmans.*
Jul. 2007. http://heartcenter.uc.edu/global.cfm?SecId=Cardiology.*
Jul. 2007. http://www.allabouted.com/my/english/understanding/faqs.html.*
Feb. 2008, http://www.musc.edu/bmt737/Spr_1999/gizelle/heart.html.*
Feb. 2008. http://www.cnn.com/HEALTH/library/DS/00162.html.*
Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Borisy, et. al., Proceedings of the National Academy of Sciences of the United States of America, 100(13) 7977-7982.*
Fukata, Y., et al., "Rho- Rho-Kinase Pathway in Smooth Muscle Contraction and Cytoskeletal Reorganization of Non-muscle Cells", Trends Pharm. Sci., 22(1): 32-39 (Jan. 2001).

* cited by examiner

Primary Examiner—James O Wilson
Assistant Examiner—Jeffrey H Murray
(74) Attorney, Agent, or Firm—Edwards Angell Palmer & Dodge LLP; Nicholas J. DiCeglie, Jr.; Barry Kramer

(57) ABSTRACT

The invention relates to heteroaryloxy-substituted phenylaminopyrimidines, to methods for the production thereof, and to the use of the same for producing medicaments for the treatment and/or prophylaxis of diseases, especially cardiovascular diseases. The inventive compounds inhibit Rho-Kinase.

6 Claims, No Drawings

HETEROARYLOXY-SUBSTITUTED PHENYLAMINOPYRIMIDINES AS RHO-KINASE INHIBITORS

The invention relates to heteroaryloxy-substituted phenylaminopyrimidines, to a process for their preparation and to their use for preparing medicaments for the treatment and/or prophylaxis of diseases in humans and animals, in particular cardiovascular disorders.

An increase in the intracellular calcium concentration is one of the main factors triggering the contraction of the vascular musculature (Somlyo, A. P. and Himpens, B. *FASEB J.* 1989, 3, 2266-2276). This is effected primarily by agonists, such as, for example, phenylephrine or thromboxane A2 which, after stimulation of the phosphatidylinositol cascade, cause the release of calcium from the sarcoplasmatic reticulum. The elevated intracellular calcium activates the MLC kinase (myosin light-chain kinase) which phosphorylates the MLC subunits of the myosin molecule (Kamm, K. H. and Stull, J. T., *Annu. Rev. Pharmacol. Toxicol.* 1985, 25, 593-603). MLC phosphorylation induces the contraction of smooth muscles, MLC dephosphorylation after reduction of the intracellular calcium concentration results in the relaxation of the vessel.

In addition to the calcium-dependent MLC phosphorylation, there is a further, central but calcium-independent, regulation mechanism of the vascular tone. This is the Rho/Rho kinase signal path (Noda, M. et al., *FEBS Lett.* 1995, 367, 246-250; Uehata, M. et al., *Nature* 1997, 389, 990-994; Fukata, Y. et al., *Trends in Pharmacological Sciences* 2001, 22, 32-39). The binding of agonists such as, for example, phenylephrine or thromboxane A2 to their receptors results in the activation of the small G-proteins Rho which then interact with and activate Rho kinase. The activated Rho kinase inhibits myosin phosphatase following phosphorylation of a subunit of the enzyme. At the same time, Rho kinase phosphorylates MLC at the position which is also phosphorylated by MLC kinase. Inhibition of myosin phosphatase and phosphorylation of MLC induces the vascular musculature to contract. In contrast, inhibition of Rho kinase leads to a relaxation of the vessels. Accordingly, inhibitors of Rho kinase lower the blood pressure and increase coronary perfusion.

In addition, inhibitors of Rho kinase cause inhibition of growth of tumor cells and metastases (Itoh et al. *Nat. Med.* 1999, 5, 221; Somlyo et al. *Biochem. Biophys. Res. Commun.* 2000, 269, 652) and inhibit angiogenesis (Uchida et al. *Biochem. Biophys. Res. Commun.* 2000, 269, 633; Gingras et al. *Biochem. J.* 2000, 348 Vol. 2, 273).

Compounds of a similar structure are known for other indications or other mechanisms of action. Thus, for example, U.S. Pat. No. 3,478,030 and U.S. Pat. No. 3,432,493 describe substituted aminopyrimidines capable of increasing coronary perfusion but acting as carboanhydrase inhibitors (*J. Chem. Inf. Comp. Sciences* 2002, 42, 94-102). Other pyrimidine derivatives have been described as anti-cancer and anti-HIV agents (Debi, M.; *Indian J. Exp. Biol.* 1997, 35, 1208-1213) or as cdk2 inhibitors (WO-A 01/64654).

It is an object of the present invention to provide medicaments for treating disorders, in particular cardiovascular disorders.

The present invention provides compounds of the formula (I)

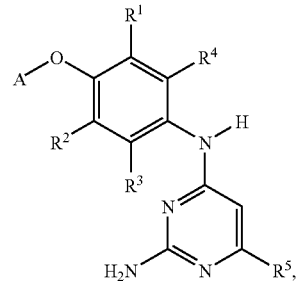

in which
A represents a radical

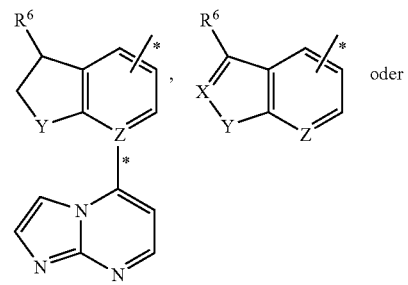

in which
X represents N or C—H,
Y represents N—$R^7$, O or S
  in which
  $R^7$ represents hydrogen, benzyl, phenyl, ($C_1$-$C_6$)-alkyl or ($C_3$-$C_8$)-cycloalkyl,
    where alkyl and cycloalkyl for their part may be substituted by fluorine, hydroxyl, amino, carboxyl, ($C_1$-$C_6$)-alkoxy, ($C_1$-$C_6$)-alkylamino or morpholinyl,
Z represents N or C—H,
$R^6$ represents hydrogen, halogen, trifluoromethyl, ($C_1$-$C_6$)-alkylamino or W—$R^7$,
  in which
  W represents NH, O or a bond,
  $R^7$ is as defined above
and
* denotes the point of attachment to the phenolic oxygen,
$R^1$ and $R^2$ independently of one another represent hydrogen, halogen or cyano,
$R^3$ and $R^4$ independently of one another represent hydrogen, fluorine or chlorine,
$R^5$ represents a radical selected from the group consisting of: hydrogen, hydroxyl, halogen, trifluoromethyl, ($C_3$-$C_8$)-cycloalkyl, ($C_1$-$C_6$)-alkyl, ($C_1$-$C_6$)-alkoxy,
  where cycloalkyl, alkyl and alkoxy for their part may be substituted by hydroxyl, carboxyl, ($C_1$-$C_6$)-alkoxy, ($C_1$-$C_6$)-alkoxycarbonyl, ($C_6$-$C_{10}$)-aryl, $NR^8R^9$ or C(=O)$NR^8R^9$,
    in which
    $R^8$ and $R^9$ independently of one another represent hydrogen, ($C_1$-$C_8$)-alkyl, optionally ($C_1$-$C_6$)-alkyl-substituted ($C_3$-$C_6$)-cycloalkyl, optionally halogen-substituted $(C_6-C_{10})$-aryl or 5- to 10-membered heteroaryl or $R^8$ and $R^9$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, $(C_6-C_{10})$-aryl, $(C_6-C_{10})$-aryloxy, 5- to 10-membered heteroaryl, 5- to 10-membered heteroaryloxy, 5- to 10-membered heterocyclyl which is attached via a carbon atom, where aryl, aryloxy, heteroaryl, heteroaryloxy and heterocyclyl for their part may be substituted by halogen, cyano, nitro, carboxyl, amino, trifluoromethyl, optionally hydroxyl-substituted $(C_1-C_6)$-alkyl, $(C_1-C_6)$-alkoxy, $(C_1-C_6)$-alkylamino, $(C_1-C_6)$-alkanoyl, $(C_1-C_6)$-alkoxycarbonyl, $(C_1-C_6)$-alkanoylamino, $(C_1-C_6)$-alkoxycarbonylamino or 5- or 6-membered heterocyclyl, $NR^{10}R^{11}$ in which $R^{10}$ and $R^{11}$ independently of one another represent hydrogen, $(C_1-C_6)$-alkyl, $(C_3-C_8)$-cycloalkyl, $(C_6-C_{10})$-aryl or 5- to 10-membered heteroaryl, where alkyl and cycloalkyl for their part may be substituted by hydroxyl, $(C_1-C_6)$-alkoxy, $(C_6-C_{10})$-aryl, 5- to 10-membered heteroaryl or $NR^{15}R^{15}$, in which $R^{15}$ and $R^{16}$ independently of one another represent hydrogen, $(C_1-C_6)$-alkyl, $(C_3-C_6)$-cycloalkyl, $(C_6-C_{10})$-aryl or 5- or 6-membered heteroaryl or $R^{15}$ and $R^{16}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, and aryl and heteroaryl for their part may be substituted by halogen, hydroxyl, amino, cyano, trifluoromethyl, $(C_1-C_6)$-alkyl, $(C_1-C_6)$-alkoxy, $(C_1-C_6)$-alkylamino or $(C_1-C_6)$-alkanoylamino, or $R^{10}$ and $R^{11}$ together with the nitrogen atom to which they are attached form a 4- to 6-membered heterocycle which may contain a further heteroatom O or N in the ring and which may be substituted by fluorine, hydroxyl, carboxyl, 5- to 7-membered heterocyclyl which may contain one or two further heteroatoms N and/or O in the ring and which for its part may be substituted by $(C_1-C_4)$-alkyl or $(C_1-C_4)$-alkoxycarbonyl, $(C_1-C_4)$-alkoxy, optionally hydroxyl-, $(C_1-C_4)$-alkoxy- or $NR^{17}R^{18}$-substituted $(C_1-C_4)$-alkyl, $(C_1-C_4)$-alkanoyl, $(C_1-C_4)$-alkoxycarbonyl or $NR^{12}R^{13}$, where $R^{12}$ and $R^{13}$ independently of one another represent hydrogen, $(C_1-C_6)$-alkyl, $(C_1-C_4)$-alkoxycarbonyl, $(C_3-C_8)$-cycloalkyl or $(C_1-C_4)$-alkanoyl or $R^{12}$ and $R^{13}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, and $R^{17}$ and $R^{18}$ independently of one another represent hydrogen, optionally hydroxyl-substituted $(C_1-C_6)$-alkyl, $(C_3-C_6)$-cycloalkyl, $(C_6-C_{10})$-aryl or 5- or 6-membered heteroaryl or $R^{17}$ and $R^{18}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, or $R^{10}$ and $R^{11}$ together with the nitrogen atom to which they are attached form a 7- to 12-membered bicyclic or tricyclic heterocycle which is fused or spirocyclic and which may have one or two further heteroatoms from the group consisting of N and O in the ring and which may be substituted by fluorine, $(C_1-C_4)$-alkyl, $(C_1-C_4)$-alkoxycarbonyl, $(C_1-C_4)$-alkanoyl or benzyl, and $C(=O)R^{14}$, in which $R^{14}$ represents $(C_1-C_6)$-alkoxy, $(C_1-C_6)$-alkylamino or a 5- to 10-membered mono- or bicyclic heterocycle which is attached via a nitrogen atom, which is fused or spirocyclic and which may have one or two further heteroatoms from the group consisting of N and O in the ring, where alkylamino for its part may be substituted by a 5- or 6-membered heterocycle, and their salts, hydrates, hydrates of the salts and solvates.

Compounds according to the invention are the compounds of the formula (I) and their salts, solvates and solvates of the salts; the compounds of the formulae given below embraced by formula (I) and their salts, solvates and solvates of the salts and the compounds given below as embodiments and embraced by formula (I) and their salts, solvates and solvates of the salts, if the compounds given below and embraced by formula (I) are not already salts, solvates and solvates of the salts.

Depending on their structure, the compounds according to the invention can exist in stereoisomeric form (enantiomers, diastereomers). Accordingly, the invention relates to the enantiomers or diastereomers and to their respective mixtures. The stereoisomerically uniform components can be isolated in a known manner from such mixtures of enantiomers and/or diastereomers.

Depending on the structure of the compounds, the invention also relates to tautomers of the compounds.

In the context of the invention, preferred salts are physiologically acceptable salts of the compounds according to the invention.

Physiologically acceptable salts of the compounds (I) include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid or benzenesulfonic acid, naphthalenedisulfonic acid, acetic acid, propionic acid, lactic acid, tartaric acid, malic acid, citric acid, fumaric acid, maleic acid, trifluoroacetic acid and benzoic acid.

Physiologically acceptable salts of the compounds (I) also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabiethylamine, arginine, lysine, ethylenediamine and methylpiperidine.

In the context of the invention, solvates are those forms of the compounds which, in solid or liquid state, form a complex by coordination with solvent molecules. Hydrates are a specific form of solvents where the coordination is with water.

In the context of the present invention, the substituents are as defined below, unless specified otherwise:

alkyl per se and "alk" and "alkyl" in alkoxy, alkanoyl, alkylamino, alkoxycarbonyl, alkoxycarbonylamino and alkanoylamino represent a straight-chain or branched alkyl radical having generally 1 to 6, preferably 1 to 4, particularly preferably 1 to 3, carbon atoms, by way of example and by way of preference methyl, ethyl, n-propyl, isopropyl, tert-butyl, n-pentyl and n-hexyl.

By way of example and by way of preference, alkoxy represents methoxy, ethoxy, n-propoxy, isopropoxy, tert-butoxy, n-pentoxy and n-hexoxy.

By way of example and by way of preference, alkanoyl represents acetyl and propanoyl.

Alkylamino represents an alkylamino radical having one or two alkyl substituents (selected independently of one another), by way of example and by way of preference methylamino, ethylamino, n-propylamino, isopropylamino, tert-butylamino, n-pentylamino, n-hexylamino, N,N-dimethylamino, N,N-diethylamino, N,N-diisopropylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino. $C_1$-$C_4$-Alkylamino, for example, represents a monoalkylamino radical having 1 to 4 carbon atoms or represents a dialkylamino radical having in each case 1 to 4 carbon atoms per alkyl substituent.

By way of example and by way of preference, alkoxycarbonyl represents methoxycarbonyl, ethoxycarbonyl, n-propoxycarbonyl, isopropoxycarbonyl, tert-butoxycarbonyl, n-pentoxycarbonyl and n-hexoxycarbonyl.

By way of example and by way of preference, alkoxycarbonylamino represents methoxycarbonylamino, ethoxycarbonylamino, n-propoxycarbonylamino, isopropoxy-carbonylamino, tert-butoxycarbonylamino, n-pentoxycarbonylamino and n-hexoxy-carbonylamino.

By way of example and by way of preference, alkanoylamino represents acetylamino and ethylcarbonylamino.

Cycloalkyl represents a cycloalkyl group having generally 3 to 8, preferably 5 to 7, carbon atoms, by way of example and by way of preference cyclopropyl, cyclobutyl, cyclopentyl, cyclohexyl and cycloheptyl.

Aryl per se and in aryloxy represents a mono- to tricyclic aromatic carbocyclic radical having generally 6 to 14 carbon atoms; by way of example and by way of preference phenyl, naphthyl and phenanthrenyl.

By way of example and by way of preference, aryloxy represents phenyloxy and naphthyloxy.

Heteroaryl per se and in heteroaryloxy represents an aromatic mono- or bicyclic radical having generally 5 to 10, preferably 5 to 6, ring atoms and up to 5, preferably up to 4, heteroatoms from the group consisting of S, O and N, by way of example and by way of preference thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

By way of example and by way of preference, heteroaryloxy represents pyridyloxy, pyrimidyloxy, indolyloxy, indazolyloxy.

Heterocyclyl and heterocycle represent a mono- or polycyclic, preferably mono- or bicyclic, non-aromatic heterocyclic radical having 4 to 10, generally 5 to 8, preferably or 6, ring atoms and up to 3, preferably up to 2, heteroatoms and/or hetero groups from the group consisting of N, O, S, SO, $SO_2$. The heterocyclyl radicals may be saturated or partially unsaturated. Preference is given to 5- or 6-membered monocyclic saturated heterocyclyl radicals having up to two heteroatoms from the group consisting of O, N and S, such as, by way of example and by way of preference, tetrahydrofuran-2-yl, tetrahydrothienyl, pyrrolidin-2-yl, pyrrolidin-3-yl, pyrrolinyl, pyranyl, piperidin-1-yl, piperidin-2-yl, piperidin-3-yl, piperidin-4-yl, thiopyranyl, morpholin-1-yl, morpholin-2-yl, morpholin-3-yl, perhydroazepinyl, piperazin-1-yl, piperazin-2-yl.

Halogen represents fluorine, chlorine, bromine and iodine.

If radicals in the compounds according to the invention are substituted, the radicals can be mono- or polysubstituted by identical or different substituents unless otherwise specified. A substition by up to three identical or different substituents is preferred. Very particular preference is given to substitution with one substituent.

Preference is given to compounds of the formula (I)

in which

A represents a radical

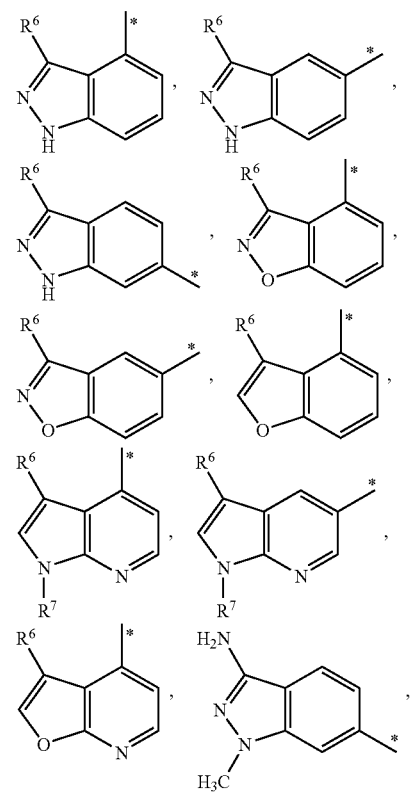

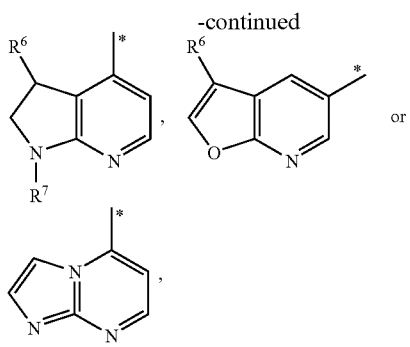

in which
R⁶ represents hydrogen, $(C_1-C_4)$-alkyl or NH—R⁷,
R⁷ represents hydrogen or $(C_1-C_4)$-alkyl
and
* denotes the point of attachment to the phenolic oxygen,
R¹ and R² independently of one another represent hydrogen, fluorine or chlorine,
R³ and R⁴ independently of one another represent hydrogen or fluorine,
R⁵ represents a radical selected from the group consisting of:
hydrogen, chlorine, $(C_3-C_8)$-cycloalkyl, $(C_1-C_6)$-alkyl, $(C_1-C_6)$-alkoxy, where alkyl and alkoxy for their part may be substituted by hydroxyl, carboxyl, $(C_1-C_4)$-alkoxy, $(C_1-C_4)$-alkoxycarbonyl, $NR^8R^9$ or $C(=O)NR^8R^9$,
in which
R⁸ and R⁹ independently of one another represent hydrogen, $(C_1-C_8)$-alkyl, optionally $(C_1-C_4)$-alkyl-substituted $(C_3-C_6)$-cycloalkyl, optionally halogen-substituted phenyl or 5- or 6-membered heteroaryl
or
R⁸ and R⁹ together with the nitrogen atom to which they are attached form a morpholine, piperazine, piperidine or pyrrolidine ring, where the rings for their part may be substituted by $(C_1-C_4)$-alkyl,
$(C_6-C_{10})$-aryl, 5- or 6-membered heteroaryl, 5- or 6-membered heterocyclyl which is attached via a carbon atom,
where aryl, heteroaryl and heterocyclyl for their part may be substituted by halogen, cyano, nitro, carboxyl, amino, trifluoromethyl, optionally hydroxyl-substituted $(C_1-C_4)$-alkyl, $(C_1-C_4)$-alkoxy, $(C_1-C_4)$-alkylamino, $(C_1-C_4)$-alkanoyl, $(C_1-C_4)$-alkoxycarbonyl, $(C_1-C_4)$-alkanoylamino, $(C_1-C_4)$-alkoxycarbonylamino or 6-membered heterocyclyl,
$NR^{10}R^{11}$
in which
R¹⁰ and R¹¹ independently of one another represent hydrogen, $(C_1-C_6)$-alkyl, $(C_3-C_8)$-cycloalkyl, phenyl or 5- or 6-membered heteroaryl,
where alkyl and cycloalkyl for their part may be substituted by hydroxyl, $(C_1-C_4)$-alkoxy, phenyl, 5- or 6-membered heteroaryl or $NR^{15}R^{16}$,
in which
R¹⁵ and R¹⁶ independently of one another represent hydrogen, $(C_1-C_4)$-alkyl, $(C_3-C_6)$-cycloalkyl, phenyl or 5- or 6-membered heteroaryl
or
R¹⁵ and R¹⁶ together with the nitrogen atom to which they are attached form a morpholine, piperazine, piperidine or pyrrolidine ring, where the rings for their part may be substituted by $(C_1-C_4)$-alkyl, and
phenyl and heteroaryl for their part may be substituted by fluorine, chlorine, hydroxyl, amino, cyano, trifluoromethyl, $(C_1-C_4)$-alkyl, $(C_1-C_4)$-alkoxy, $(C_1-C_4)$-alkylamino or $(C_1-C_4)$-alkanoylamino,
or
R¹⁰ and R¹¹ together with the nitrogen atom to which they are attached form a 4- to 6-membered heterocycle which may contain a further heteroatom O or N in the ring and which may be substituted by fluorine, hydroxyl, carboxyl, 5- to 7-membered heterocyclyl which may contain one or two further heteroatoms N and/or O in the ring and which for its part may be substituted by $(C_1-C_4)$-alkyl or $(C_1-C_4)$-alkoxycarbonyl, $(C_1-C_4)$-alkoxy, optionally hydroxyl-, $(C_1-C_4)$-alkoxy- or $NR^{17}R^{18}$-substituted $(C_1-C_4)$-alkyl, $(C_1-C_4)$-alkanoyl, $(C_1-C_4)$-alkoxycarbonyl or $NR^{12}R^{13}$,
where
R¹² and R¹³ independently of one another represent hydrogen or $(C_1-C_4)$-alkyl
or
R¹² and R¹³ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl,
and
R¹⁷ and R¹⁸ independently of one another represent hydrogen, optionally hydroxyl-substituted $(C_1-C_4)$-alkyl or phenyl
or
R¹⁷ and R¹⁸ together with the nitrogen atom to which they are attached form a pyrrolidine ring,
or
R¹⁰ and R¹¹ together with the nitrogen atom to which they are attached form a 7- to 12-membered bicyclic or tricyclic heterocycle which is fused or spirocyclic, which may have one or two further heteroatoms from the group consisting of N and O in the ring and which may be substituted by $(C_1-C_4)$-alkyl, $(C_1-C_4)$-alkoxycarbonyl, $(C_1-C_4)$-alkanoyl or benzyl,
and $C(=O)R^{14}$
in which
R¹⁴ represents $(C_1-C_6)$-alkoxy, $(C_1-C_6)$-alkylamino or a 5- to 10-membered mono- or bicyclic heterocycle which is attached via a nitrogen atom, which is fused or spirocyclic and which may have one or two further heteroatoms from the group consisting of N and O in the ring,
where alkylamino for its part may be substituted by a 5- or 6-membered heterocyclyl
and their salts, hydrates, hydrates of the salts and solvates.
Particular preference is given to compounds of the formula (I)
in which
A represents a radical

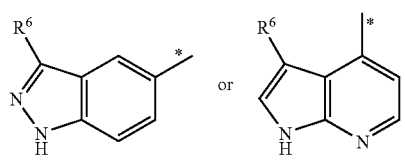

in which

R⁶ represents hydrogen or methyl and

* denotes the point of attachment to the phenolic oxygen, $R^1$ and $R^2$ independently of one another represent hydrogen, fluorine or chlorine, $R^3$ and $R^4$ represent hydrogen, $R^5$ represents a radical selected from the group consisting of:
hydrogen, chlorine, cyclohexyl, $(C_1-C_4)$-alkyl, $(C_1-C_4)$-alkoxy,
where alkyl and alkoxy for their part may be substituted by hydroxyl, carboxyl, $(C_1-C_4)$-alkoxy, methyloxycarbonyl, ethyloxycarbonyl, $NR^8R^9$ or $C(=O)NR^8R^9$,
in which
$R^8$ and $R^9$ independently of one another represent hydrogen, $(C_1-C_8)$-alkyl, cyclopropyl, optionally methyl-substituted cyclopentyl or optionally fluorine-substituted phenyl
or
$R^8$ and $R^9$ together with the nitrogen atom to which they are attached form a piperidine, 2-methylpiperidine or 2,6-dimethylpiperidine ring,
phenyl, pyridyl, pyrrolyl, piperidin-3-yl, piperidin-4-yl, pyrrolidin-2-yl, where phenyl, pyridyl and pyrrolyl for their part may be substituted by fluorine, chlorine, bromine, cyano, nitro, trifluoromethyl, methyl, hydroxymethyl, methoxy, dimethylamino or morpholinyl,
and
piperidin-3-yl, piperidin-4-yl and pyrrolidin-2-yl for their part may be substituted by methyl, ethyl, n-propyl, isopropyl, methylcarbonyl or ethylcarbonyl,
$NR^{10}R^{11}$
in which
$R^{10}$ and $R^{11}$ independently of one another represent hydrogen, $(C_1-C_4)$-alkyl, 3-hydroxypropyl, 2-hydroxycyclohexyl, 2-aminocyclohexyl, phenyl, pyridyl or pyrazolyl,
where phenyl and pyridyl for their part may be substituted by chlorine, hydroxyl, amino, cyano, methyl or methoxy,
or
$R^{10}$ and $R^{11}$ together with the nitrogen atom to which they are attached form a piperazine, 3-methylpiperazine, 3,5-dimethylpiperazine, 4-isobutylpiperazine, morpholine, pyrrolidine, 3-aminopyrrolidine, 3-methylamino-pyrrolidine, 3-(N,N-dimethylamino)pyrrolidine, 2-aminomethylpyrrolidine, 3-hydroxypyrrolidine, 2-hydroxymethylpyrrolidine or 2-methoxymethyl-pyrrolidine ring or a radical

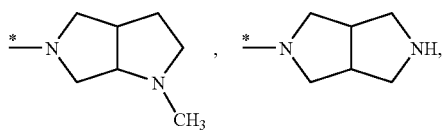

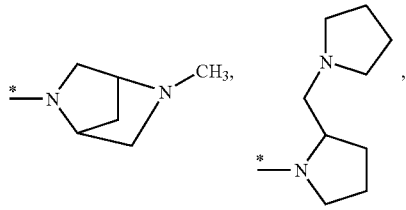

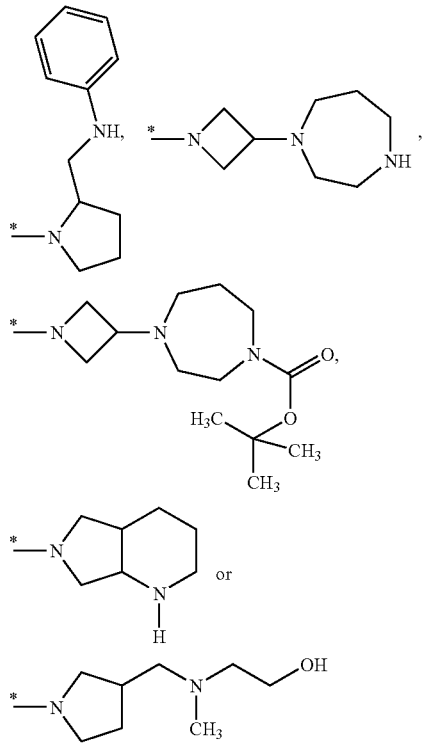

in which
* denotes the point of attachment to the pyrimidine ring,
and $C(=O)R^{14}$
in which
$R^{14}$ represents methoxy, piperidinyl-N-ethylamino, piperidinyl or piperazinyl, and their salts, hydrates, hydrates of the salts and solvates.

Particular preference is also given to compounds of the formula (I) in which A represents a radical

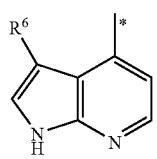

in which
R⁶ represents hydrogen or methyl and
* denotes the point of attachment to the phenolic oxygen.

Particular preference is also given to compounds of the formula (I) in which $R^1$ represents fluorine.

Particular preference is also given to compounds of the formula (I) in which $R^2$ represents fluorine or hydrogen.

Particular preference is also given to compounds of the formula (I) in which $R^3$ and $R^4$ represent hydrogen.

Very particular preference is given to combinations of two or more of the preferred range as mentioned above.

The present invention provides compounds of the formula (I) in which
A represents a radical

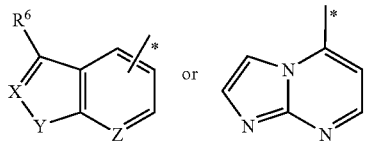

in which
X represents N or C—H,
Y represents N—$R^7$, O or S
in which
$R^7$ represents hydrogen, benzyl, phenyl, $(C_1-C_6)$-alkyl or $(C_3-C_8)$-cycloalkyl,
where alkyl and cycloalkyl for their part may be substituted by fluorine, hydroxyl, amino, carboxyl, $(C_1-C_6)$-alkoxy, $(C_1-C_6)$-alkylamino or morpholinyl,
Z represents N or C—H,
$R^6$ represents hydrogen, halogen, trifluoromethyl, $(C_1-C_6)$-alkylamino or W—$R^7$,
in which
W represents NH, O or a bond,
$R^7$ is as defined above
and
* denotes the point of attachment to the phenolic oxygen,
$R^1$ and $R^2$ independently of one another represent hydrogen, halogen or cyano,
$R^3$ and $R^4$ independently of one another represent hydrogen, fluorine or chlorine,
$R^5$ represents a radical selected from the group consisting of:
hydroxyl, halogen, trifluoromethyl,
$(C_1-C_6)$-alkyl, $(C_1-C_6)$-alkoxy, $(C_3-C_8)$-cycloalkyl,
where alkyl, alkoxy and cycloalkyl for their part may be substituted by hydroxyl, $(C_1-C_6)$-alkoxy, $(C_6-C_{10})$-aryl or $NR^8R^9$,
in which
$R^8$ and $R^9$ independently of one another represent hydrogen, $(C_1-C_6)$-alkyl or 5- to 10-membered heteroaryl
or
$R^8$ and $R^9$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl,
$(C_6-C_{10})$-aryl, $(C_6-C_{10})$-aryloxy, 5- to 10-membered heteroaryl, 5- to 10-membered heteroaryloxy,
where aryl, aryloxy, heteroaryl and heteroaryloxy for their part may be substituted by halogen, nitro, carboxyl, amino, trifluoromethyl, $(C_1-C_6)$-alkyl, $(C_1-C_6)$-alkoxy, $(C_1-C_6)$-alkylamino, $(C_1-C_6)$-alkanoyl, $(C_1-C_6)$-alkoxycarbonyl, $(C_1-C_6)$-alkanoylamino or $(C_1-C_6)$-alkoxycarbonylamino,
and $NR^{10}R^{11}$
in which
$R^{10}$ and $R^{11}$ independently of one another represent hydrogen, $(C_1-C_6)$-alkyl, $(C_3-C_8)$-cycloalkyl, $(C_6-C_{10})$-aryl or 5- to 10-membered heteroaryl,
where alkyl and cycloalkyl for their part may be substituted by hydroxyl, $(C_1-C_6)$-alkoxy, $(C_6-C_{10})$-aryl, 5- to 10-membered heteroaryl or $NR^8R^9$ in which
$R^8$ and $R^9$ are as defined above
and
aryl and heteroaryl for their part may be substituted by fluorine, chlorine, amino, trifluoromethyl, $(C_1-C_6)$-alkyl $(C_1-C_6)$-alkyl-amino or $(C_1-C_6)$-alkanoylamino,
or
$R^{10}$ and $R^{11}$ together with the nitrogen atom to which they are attached form a 5- or 6-membered heterocycle which is substituted by fluorine, carboxyl, 1,1-dioxyethylene, 5- or 6-membered heterocyclyl, having one or two heteroatoms N and/or O (which for its part may be substituted by $(C_1-C_4)$-alkyl), $(C_1-C_4)$-alkoxy, hydroxyl- or $(C_1-C_4)$-alkoxy-substituted $(C_1-C_4)$-alkyl, $(C_1-C_4)$-alkanoyl or $NR^{12}R^{13}$
in which
$R^{12}$ and $R^{13}$ independently of one another represent hydrogen, $(C_1-C_6)$-alkyl, $(C_1-C_4)$-alkoxycarbonyl, $(C_3-C_8)$-cyclo-alkyl or $(C_1-C_4)$-alkanoyl
or
$R^{12}$ and $R^{13}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl,
or
$R^{10}$ and $R^{11}$ together with the nitrogen atom to which they are attached form a 7- to 12-membered bicyclic heterocycle which is fused or spirocyclic, which may have one or two further heteroatoms from the group consisting of N and O in the ring and which may be substituted by fluorine, $(C_1-C_4)$-alkyl, $(C_1-C_4)$-alkoxycarbonyl, $(C_1-C_4)$-alkanoyl or benzyl, and their salts, hydrates, hydrates of the salts and solvates.
Preference is given to compounds of the formula (I)

in which
A represents a radical

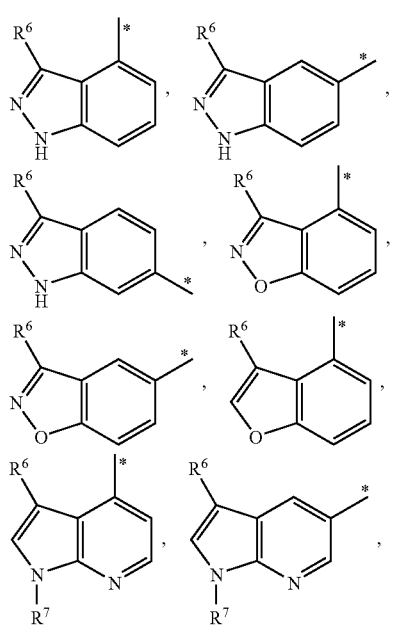

-continued

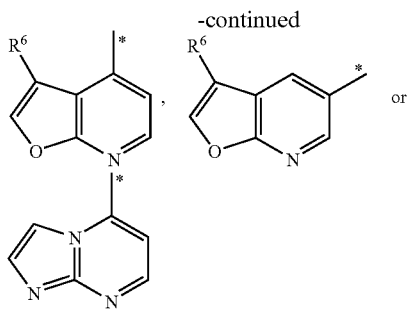

in which
R[6] represents hydrogen, $(C_1-C_4)$-alkyl, hydroxyl, fluorine, chlorine or NH—R[7],
R[7] represents hydrogen or $(C_1-C_4)$-alkyl which may be substituted by fluorine, hydroxyl, methoxy, $(C_1-C_4)$-alkylamino or morpholinyl
and
* denotes the point of attachment to the phenolic oxygen,
R[1] and R[2] independently of one another represent hydrogen, fluorine or chlorine,
R[3] and R[4] represent hydrogen,
R[5] represents a radical selected from the group consisting of: hydroxyl, chlorine, trifluoromethyl,
$(C_1-C_6)$-alkyl, $(C_1-C_6)$-alkoxy, $(C_3-C_8)$-cycloalkyl,
where alkyl, alkoxy and cycloalkyl for their part may be substituted by NR[8]R[9]
in which
R[8] and R[9] independently of one another represent hydrogen, $(C_1-C_4)$-alkyl or 5- or 6-membered heteroaryl or
R[8] and R[9] together with the nitrogen atom to which they are attached form a morpholine, piperazine or N-methylpiperazine ring,
$(C_6-C_{10})$-aryl, $(C_6-C_{10})$-aryloxy, 5- to 10-membered heteroaryl, 5- to 10-membered heteroaryloxy,
where aryl, aryloxy, heteroaryl and heteroaryloxy for their part may be substituted by fluorine, chlorine, nitro, carboxyl, amino, trifluoromethyl, $(C_1-C_4)$-alkyl, $(C_1-C_4)$-alkoxy, $(C_1-C_4)$-alkylamino, $(C_1-C_4)$-alkoxycarbonyl, $(C_1-C_4)$-alkanoylamino or $(C_1-C_4)$-alkoxy-carbonylamino,
and NR[10]R[11]
in which
R[10] and R[11] independently of one another represent hydrogen, $(C_1-C_6)$-alkyl, $(C_3-C_8)$-cycloalkyl, $(C_6-C_{10})$-aryl or 5- to 10-membered heteroaryl,
where alkyl and cycloalkyl for their part may be substituted by hydroxyl, $(C_1-C_6)$-alkoxy, $(C_6-C_{10})$-aryl, 5- to 10-membered heteroaryl or NR[8]R[9]
in which
R[8] and R[9] are as defined above
and
aryl and heteroaryl for their part may be substituted by fluorine, chlorine, amino, trifluoromethyl, $(C_1-C_6)$-alkyl $(C_1-C_6)$-alkyl-amino or $(C_1-C_6)$-alkanoylamino,
or
R[10] and R[11] together with the nitrogen atom to which they are attached form a 5- or 6-membered heterocycle which is substituted by fluorine, carboxyl, 1,1-dioxyethylene, 5- or 6-membered heterocyclyl having one or two heteroatoms N and/or O (which for its part may be substituted by $(C_1-C_4)$-alkyl), $(C_1-C_4)$-alkoxy, hydroxyl- or $(C_1-C_4)$-alkoxy-substituted $(C_1-C_4)$-alkyl, $(C_1-C_4)$-alkanoyl or NR[12]R[13]
in which
R[12] and R[13] independently of one another represent hydrogen, $(C_1-C_6)$-alkyl, $(C_1-C_4)$-alkoxycarbonyl, $(C_3-C_8)$-cycloalkyl or $(C_1-C_4)$-alkanoyl
or
R[12] and R[13] together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl,
or
R[10] and R[11] together with the nitrogen atom to which they are attached form a 7- to 12-membered bicyclic heterocycle which is fused or spirocyclic, which may have one or two further heteroatoms from a group consisting of N and O in the ring and which may be substituted by fluorine, $(C_1-C_4)$-alkyl, $(C_1-C_4)$-alkoxycarbonyl, $(C_1-C_4)$-alkanoyl or benzyl, and their salts, hydrates, hydrates of the salts and solvates.
Particular preference is given to compounds of the formula (I)
in which
A represents a radical

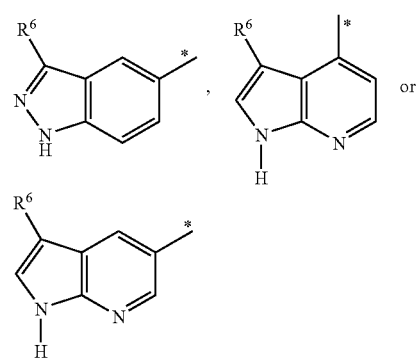

in which
R[6] represents hydrogen or amino
and
* denotes the point of attachment to the phenolic oxygen,
R[1] and R[2] independently of one another represent hydrogen, fluorine or chlorine,
R[3] and R[4] represent hydrogen,
R[5] represents a radical selected from the group consisting of: $(C_1-C_4)$-alkyl, $(C_1-C_4)$-alkoxy,
where alkyl and alkoxy for their part may be substituted by amino or morpholinyl,
phenyl, phenoxy, pyridyl, pyridyloxy,
where phenyl, phenoxy, pyridyl and pyridyloxy for their part may be substituted by fluorine, chlorine, amino, methyl or NH—CO—CH$_3$,
and NR[10]R[11]
in which
R[10] and R[11] independently of one another represent hydrogen, 2-hydroxyethyl, 3-hydroxypropyl, 2-aminoethyl, 3-amino-propyl, 2-morpholinoethyl, 3-morpholinopropyl, 2-aminocyclohexyl, pyridyl or aminopyridyl or
R[10] and R[11] together with the nitrogen atom to which they are attached form a piperazine, N-methylpipera-zine or N-isopropyl-piperazine ring or a radical

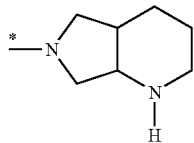

in which
* denotes the point of attachment to the pyrimidine ring, and their salts, hydrates, hydrates of the salts and solvates.

The present invention also provides a process for preparing the compounds of the formula (I) which is characterized in that either

[A] compounds of the formula (II)

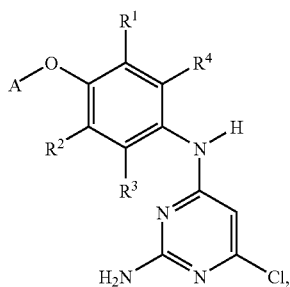

in which
A, R[1], R[2], R[3] and R[4] are as defined above
are reacted with compounds of the formula (III)

$$R^5-X^1 \quad (III),$$

in which
R[5] is as defined above and
X[1] represents hydrogen, B(OH)$_2$ or a boronic acid ester such as

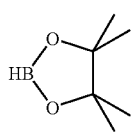

or
[B] compounds of the formula (IV)

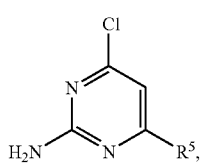

in which
R[5] is as defined above
are reacted with compounds of the formula (V)

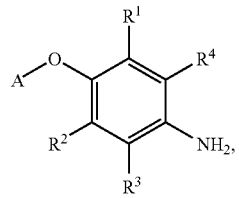

in which
A, R[1], R[2], R[3] and R[4] are as defined above
to give compounds of the formula (I).

In process step [A], if X[1] represents hydrogen, the reaction is carried out, if appropriate in the presence of a base, either in inert solvents at atmospheric pressure in a temperature range of from 20° C. to reflux of the solvents or at elevated pressure in an autoclave at temperatures above the boiling point of the solvent to 250° C. or alternatively neat in the melt.

Inert solvents are, for example, alcohols, such as methanol, ethanol, propanol, isopropanol, butanol or 2-ethylhexanol, N-alkylated carboxamides, such as dimethyl-formamide, dimethylacetamide or N-methylpyrrolidone, alkyl sulfoxides, such as dimethyl sulfoxide, or other solvents, such as acetonitrile or pyridine. Preference is given to ethanol, butanol, 2-ethylhexanol, N-methylpyrrolidone or dimethylformamide.

Bases are, for example, alkali metal hydroxides, such as sodium hydroxide or potassium hydroxide, or alkali metal alkoxides, such as sodium tert-butoxide or potassium tert-butoxide, or alkali metal carbonates, such as cesium carbonate, sodium carbonate or potassium carbonate, or amides, such as lithium diisopropylamide, or other bases, such as DBU, triethylamine or diisopropylethylamine, preferably diisopropylethylamine or triethylamine.

In process step [A], if X[1] represents B(OH)$_2$ or an equivalent group, such as, for example, a boronic acid ester, the conversion into compounds of the formula (I) is generally carried out in inert solvents in the presence of a transition metal catalyst in the presence of a base, preferably in a temperature range of from 70° C. to 150° C., at atmospheric pressure.

Inert solvents are, for example, ethers, such as dioxane, tetrahydrofuran or 1,2-dimethoxyethane, hydrocarbons, such as benzene, xylene or toluene, nitroaromatic compounds, such as nitrobenzene, optionally N-alkylated carboxamides, such as dimethylformamide, dimethylacetamide, alkyl sulfoxides, such as dimethyl sulfoxide, or cyclic lactams, such as N-methylpyrrolidone. If appropriate, the solvents are used with added ethanol or water. Preferred solvents are dimethylformamide, 1,2-dimethoxyethane and toluene/ethanol.

Preferred as transition metal catalysts are palladium(0) or palladium(II) compounds, in particular bis(diphenylphosphaneferrocenyl)palladium(II)chloride, dichlorobis(tri-phenylphosphine)palladium or tetrakis(triphenylphosphine)palladium(0).

Preferred as bases are sodium tert-butoxide or potassium tert-butoxide, or alkali metal hydroxides or alkali metal salts, such as potassium acetate, sodium hydroxide, sodium bicarbonate, sodium carbonate or potassium carbonate, if appropriate in the form of their aqueous solutions.

In process step [B], the conversion into compounds of the formula (I) is carried out in aqueous hydrochloric acid solution, preferably in a temperature range of from 70° C. to 110° C. at atmospheric pressure.

For preparing the compounds of the formula (If) from process step [A], compounds of the formula (V) are reacted with the compound of the formula (VI)

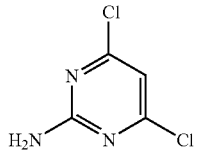
(VI)

under reaction conditions as described for process step [B].

To prepare the compounds of the formula (IV) from process step [B], compounds of the formula (VII)

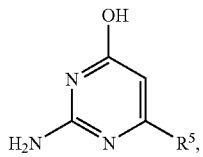
(VII)

in which $R^5$ is as defined above are reacted in phosphoryl chloride with addition of from 0.01 to 1 equivalent of dimethylformamide or N,N-dimethylaniline or N,N-diethylanilin, preferably in a temperature range of from 50° C. to the reflux temperature of the solvent at atmospheric pressure.

In another process variant, to prepare compounds of the formula (IV), compounds of the formula (VI) are reacted with compounds of the formula (III) under reaction conditions as described for process step [A].

To prepare compounds of the formula (VII), compounds of the formula (VII)

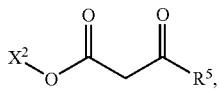
(VIII)

in which $R^5$ is as defined above and $X^2$ represents alkyl preferably methyl or ethyl, are reacted with the compound of the formula (IX)

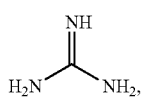
(IX)

or its salts, preferably its carbonate.

The reaction of the compounds of the formulae (VI) and (IX) is carried out, for example, in two steps, initially with concentrated hydrochloric acid in ethanol, preferably in a temperature range of from 50° C. to reflux of the solvents at atmospheric pressure, and then with aqueous sodium hydroxide solution, preferably in a temperature range of from 50° C. to reflux of the solvents under atmospheric pressure.

To prepare the compounds of the formula (V) from process step [B], either compounds of the formula (X)

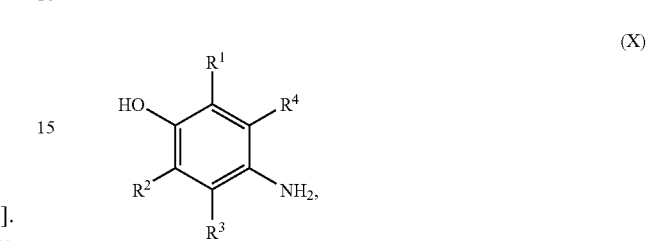
(X)

in which $R^1$, $R^2$, $R^3$ and $R^4$ are as defined above are reacted with compounds of the formula (XI)

$A-X^3$ (XI), in which

A is as defined above and $X^3$ represents halogen, preferably fluorine or chlorine.

If $X^3$ is attached to a pyridine ring, $X^3$ may represent a nitro group.

The reaction is preferably carried out neat in the presence of potassium hydroxide as base in the melt at a temperature of from 200° C. to 280° C. or in an inert solvent, such as, for example, N,N-dimethylformamide, N-methylpyrrolidone or nitrobenzene, in the presence of a base, such as, for example, potassium hydroxide, potassium tert-butoxide or sodium hydride, at a temperature of from 120° C. to 280° C.

Alternatively, compounds of the formula (V) can be prepared by reacting compounds of the formula (XII)

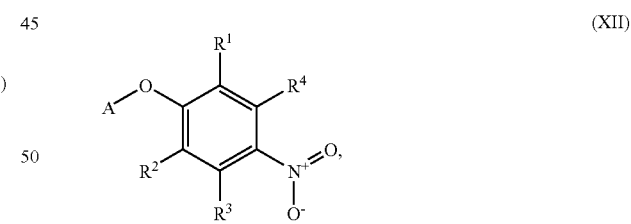
(XII)

in which

A, $R^1$, $R^2$, $R^3$ and $R^4$ are as defined above with reducing agents.

The reaction is generally carried out in inert solvents, preferably in a temperature range of from room temperature to reflux of the solvents at from atmospheric pressure to 3 bar.

Reducing agents are, for example, palladium on activated carbon and hydrogen, platinum oxide on activated carbon and hydrogen, tin dichloride or titanium trichloride; preference is given to palladium on activated carbon and hydrogen in the presence of hydrazine hydrate or platinum oxide on activated carbon and hydrogen.

Inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, alcohols, such as methanol, ethanol, n-propanol, isopropanol, n-butanol, tert-butanol or 2-ethylhexanol, hydrocarbons, such as benzene, xylene, toluene, hexane, cyclohexane or mineral oil fractions, or other solvents, such as dimethylformamide, dimethylacetamide, acetonitrile or pyridine; preferred solvents are ethanol, n-butanol and 2-ethylhexanol.

To prepare the compounds of the formula (XII), compounds of the formula (XIII)

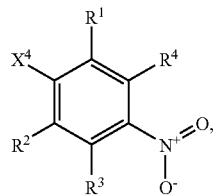

(XIII)

in which $R^1$, $R^2$, $R^3$ and $R^4$ are as defined above and $X^4$ represents halogen, preferably fluorine or chlorine, are reacted with compounds of the formula (XIV)

 A-OH  (XIV)

in which

A is as defined above.

The reaction is generally carried out in inert solvents, if appropriate in the presence of a base, preferably in a temperature range of from room temperature to reflux of the solvents at atmospheric pressure.

Inert solvents are, for example, halogenated hydrocarbons, such as methylene chloride, trichloromethane or 1,2-dichloroethane, ethers, such as dioxane, tetrahydrofuran or 1,2-dimethoxyethane, or other solvents, such as acetone, dimethylformamide, dimethylacetamide, 2-butanone or acetonitrile, preferably acetonitrile, dimethylformamide or 1,2-dimethoxyethane.

Bases are, for example, alkali metal carbonates, such as cesium carbonate, sodium carbonate or potassium carbonate, or sodium methoxide or potassium methoxide, or sodium ethoxide or potassium ethoxide or potassium tert-butoxide, or amides, such as sodium amide, lithium bis(trimethylsilyl) amide or lithium diisopropylamide, or organometallic compounds, such as butyllithium or phenyllithium, or other bases, such as sodium hydride, DBU, preferably potassium tert-butoxide, cesium carbonate, potassium carbonate or sodium carbonate.

The compounds of the formulae (III), (VI), (VIII), (IX), (X), (XI), (XIII) and (XIV) are known per se to the person skilled in the art, or they can be prepared by customary literature methods.

The compounds of the formula (I) can be derivatized further, for example by reaction with oxidizing agents.

The preparation of the compounds according to the invention can be illustrated by the synthesis schemes below.

[A]

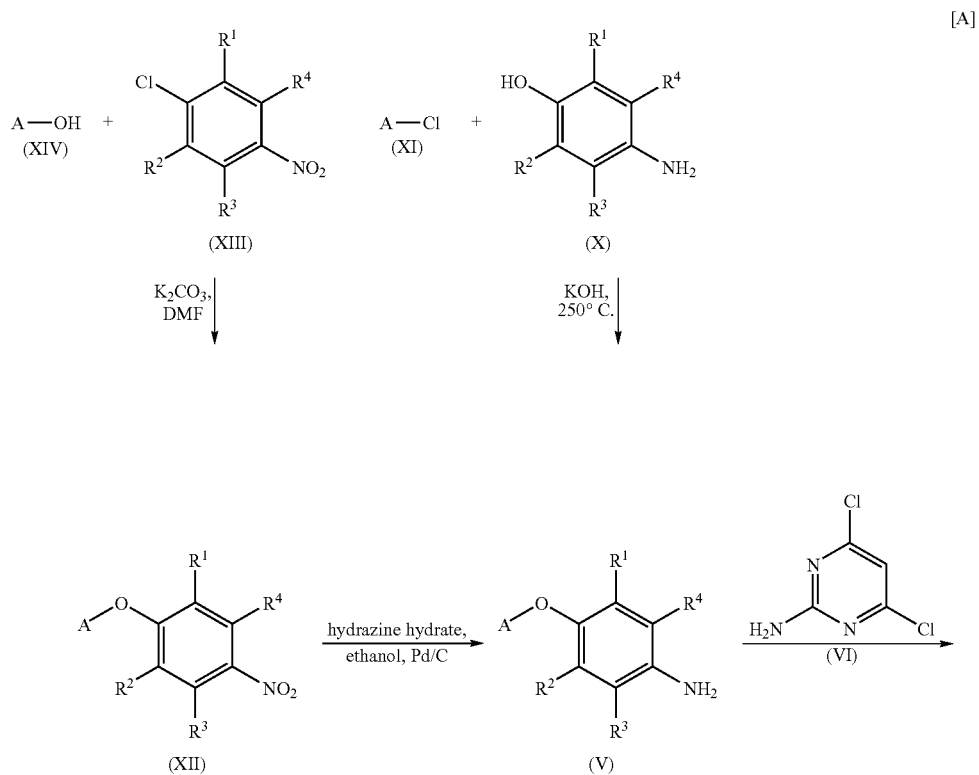

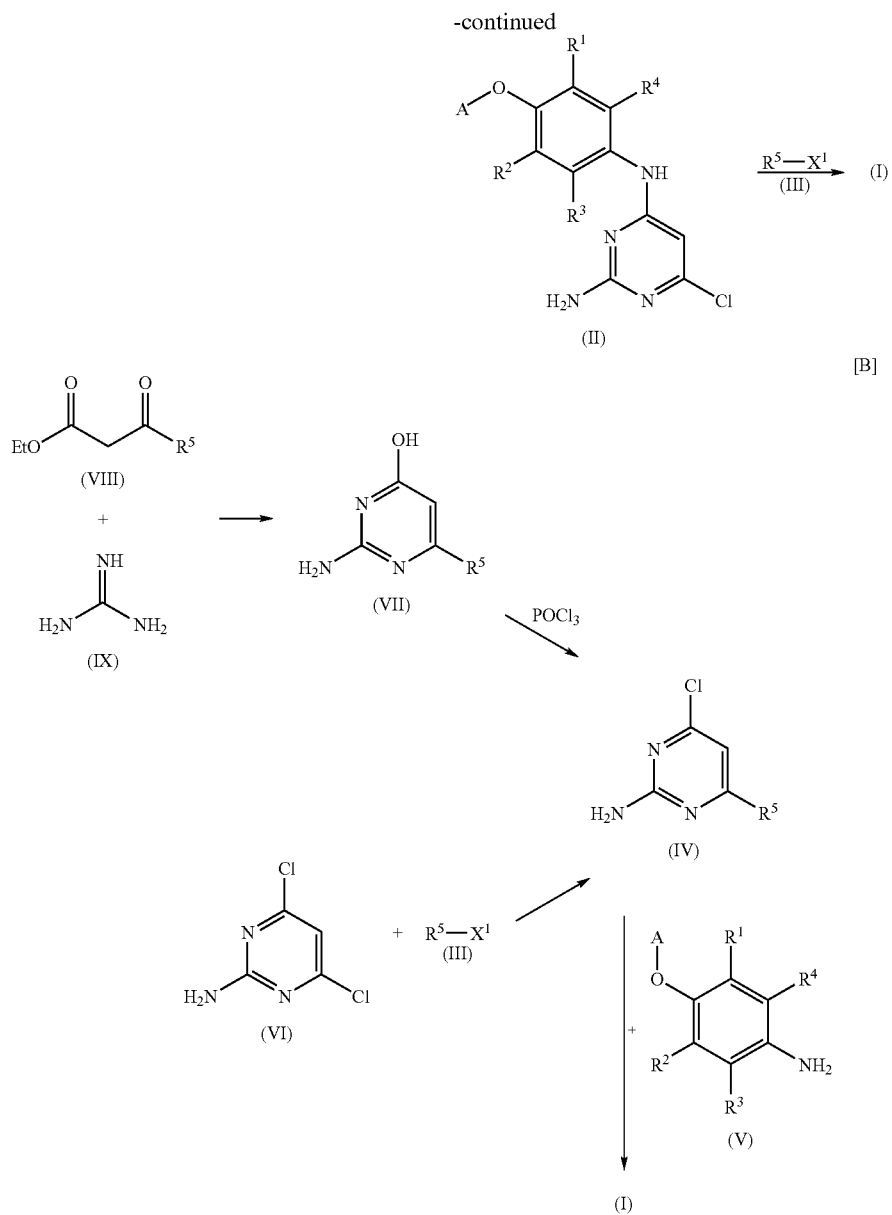

The compounds according to the invention have an unforeseeable useful spectrum of pharmacological and pharmacokinetic actions.

Accordingly, they are suitable for use as pharmaceuticals for the treatment and/or prophylaxis of diseases in humans and animals.

The pharmaceutical activity of the compounds according to the invention can be explained by their action as Rho kinase inhibitors.

The present invention also provides the use of the compounds according to the invention for the treatment of and/or prophylaxis of disorders, preferably cardiovascular disorders.

The compounds according to the invention are suitable for the prophylaxis and/or treatment of cardiovascular disorders such as, for example, hypertension and cardiac insufficiency, stable and unstable angina pectoris, disorders of peripheral and cardiac vessels, of arrhythmias, of thrombolic disorders and ischemias, such as myocardial infarction, stroke, transitory and ischemic attacks, obstruction of peripheral circulation, subarachnoidal hemorrhages, prevention of restenoses, such as, for example, after thrombolysis therapies, percutaneous translumino angioplasties (PTA) percutaneous transluminal coronary angioplasties (PTCA), bypass, and for the prophylaxis and/or treatment of arteriosclerosis, asthmatic disorders, COPD and diseases of the urogenital system, such as, for example, prostate hypertrophy, erectile dysfunction, female sexual dysfunction, osteoporosis, gastroparesis and incontinence.

The compounds according to the invention can furthermore be used for the prophylaxis and/or treatment of cancer, in particular of tumors.

In the context of the present invention, the definition of tumors includes both benign and malignant tumors and thus, for example, also benign neoplasias, dysplasias, hyperplasias, and neoplasias with metastasis formation. Further examples of tumors are carcinomas, sarcomas, carcincosarcomas, tumors of the hemopoietic organs, tumors of the nervous tissue, for example of the brain, or tumors of skin cells. In tumor formation, uncontrolled or inadequately controlled cell division occurs. The tumor can be locally restricted, but it can also infiltrate the surrounding tissue and then get lodged by the lymphatic system or by the bloodstream in a new location. There are thus primary and secondary tumors. Primary tumors are originally formed in the organ in which they are found. Secondary tumors have been lodged in another organ by metastasis formation and then spread in their new location.

The present invention also provides the use of the compounds according to the invention for the prophylaxis and/or treatment of disorders, in particular the syndromes mentioned above.

The present invention also provides the use of the compounds according to the invention for preparing medicaments for the prophylaxis and/or treatment of disorders, in particular the syndromes mentioned above.

The present invention also provides a method for the prophylaxis and/or treatment of disorders, in particular the disorders mentioned above, using a cardiovascularly effective amount of the compound according to the invention.

The present invention also provides medicaments, comprising a compound according to the invention and one or more further active compounds, in particular for the prophylaxis and/or treatment of the disorders mentioned above.

The compound according to the invention can act systemically and/or locally. For this purpose, it can be administered in a suitable manner, such as, for example, orally, parenterally, pulmonarily, nasally, sublingually, lingually, buccally, rectally, transdermally, conjunctivally, otically, as stents or as an implant.

For these administration routes, the compound according to the invention can be administered in suitable administration forms.

Suitable for oral administration are administration forms working according to the prior art, which release the compounds according to the invention rapidly and/or in modified form and which contain the compounds according to the invention in crystalline and/or amorphized and/or dissolved form, such as, for example, tablets (non-coated or coated tablets, for example coated with enteric, slowly dissolving or insoluble coats which control the release of the compounds according to the invention), tablets which decompose rapidly in the oral cavity or films/wafers, capsules, sugar-coated tablets, granules, pellets, powders, emulsions, suspensions, aerosols or solutions.

Parenteral administration can take place with circumvention of an absorption step (intravenous, intraarterial, intracardiac, intraspinal or intralumbar) or with involvement of an absorption (intramuscular, subcutaneous, intracutaneous, percutaneous or intraperitoneal). For parenteral administration, suitable administration forms are, inter alia, injection and infusion preparations in the form of solutions, suspensions, emulsions, lyophilisates and sterile powders.

Suitable for the other administration routes are, for example, pharmaceutical forms for inhalation (inter alia powder inhalers, nebulizers), nasal drops/solutions, sprays; tablets or capsules to be applied lingually, sublingually or buccally, suppositories, ear and eye preparations, gyno capsules, aqueous suspensions (lotions, shake lotions), lipophilic suspensions, ointments, creams, milk, pastes, dusting powder or implants.

The compounds according to the invention can be converted into the administration forms mentioned in a manner known per se. This takes place using inert non-toxic, pharmaceutically acceptable auxiliaries. These include, inter alia, carriers (for example microcrystalline cellulose), solvents (for example liquid polyethylene glycols), emulsifiers (for example sodium dodecylsulfate), dispersants (for example polyvinylpyrrolidone), synthetic and natural biopolymers (for example albumin), stabilizers (for example antioxidants, such as ascorbic acid), colorants (for example inorganic pigments, such as iron oxides) or taste and/or odor corrigens.

The present invention also provides medicaments comprising at least one compound according to the invention, preferably together with one or more inert non-toxic, pharmaceutically acceptable auxiliaries, and their use for the purposes mentioned above.

In general, it has been found to be advantageous both in human and in veterinary medicine to administer the compound according to the invention in total amounts of from about 0.01 to about 700, preferably 0.01 to 100, mg/kg of body weight per 24 hours, if appropriate in the form of a plurality of individual doses, to obtain the desired results. An individual dose contains the compound according to the invention preferably in amounts of from about 0.1 to about 80, in particular 0.1 to 30, mg/kg of body weight.

In spite of this, it may be necessary, if appropriate, to deviate from the amounts mentioned, namely depending on the body weight, the route of administration, the individual response to the active compound, the type of preparation and the time or interval at which administration takes place. Thus, in some cases it may be sufficient to use less than the above-mentioned minimum amount, whereas in other cases the upper limit mentioned has to be exceeded. In the case of the administration of relatively large amounts, it may be advisable to divide these into several individual administrations over the course of the day.

The percentages in the tests and examples below are, unless indicated otherwise, percentages by weight; parts are parts by weight. Solvent ratios, dilution ratios and concentrations of liquid/liquid solutions are in each case based on the volume.

A. EXAMPLES

Abbreviations

| | |
|---|---|
| TLC | thin-layer chromatography |
| DCI | direct chemical ionization (in MS) |
| DCM | dichloromethane |
| DIEA | N,N-diisopropylethylamine |
| DMA | dimethylacetamide |
| DMF | N,N-dimethylformamide |
| DMSO | dimethyl sulfoxide |
| EA | ethyl acetate |
| EI | electron impact ionization (in MS) |
| ESI | electrospray ionization (in MS) |
| m.p. | melting point |
| sat. | saturated |
| h | hour |
| HATU | O-(7-azabenzotriazol-1-yl)-N,N,N',N'-tetramethyluronium hexafluorophosphate |
| HOAT | 3H-[1,2,3]-triazol [4,5-b]pyridin-3-ole |
| HOBt | 1-hydroxy-1H-benzotriazole x $H_2O$ |
| HPLC | high pressure, high performance liquid chromatography |
| conc. | concentrated |
| LC-MS | liquid chromatography-coupled mass spectroscopy |
| LDA | lithium diisopropylamide |
| min | minutes |

-continued

| MPLC | medium pressure, medium performance liquid chromatography |
| MS | mass spectroscopy |
| NMR | nuclear magnetic resonance spectroscopy |
| org. | organic |
| RF | reflux |
| $R_f$ | retention factor (in TLC) |
| RP-HPLC | reverse Phase HPLC |
| RT | room temperature |
| $R_t$ | retention time (in HPLC) |
| TFA | trifluoroacetic acid |
| THF | tetrahydrofuran |

HPLC, LCMS and GCMS Methods:

Method 1 (LC/MS)

Instrument: Micromass Platform LCZ, HP1100; column: Symmetry C18, 50 mm×2.1 mm, 3.5 µm; mobile phase A: water+0.05% formic acid, mobile phase B: acetonitrile+0.05% formic acid; gradient: 0.0 min 90% A→4.0 min 10% A→6.0 min 10% A; oven: 40° C.; flow rate: 0.5 ml/min; UV detection: 208-400 nm.

Method 2 (LC/MS)

Instrument: Micromass Platform LCZ with HPLC Agilent Series 1100; column: Grom-SIL120 ODS-4 HE, 50 mm×2.0 mm, 3 µm; mobile phase A: 1 l water+1 ml 50% strength formic acid, mobile phase B: 1 l acetonitrile+1 ml 50% strength formic acid; gradient: 0.0 min 100% A→0.2 min 100% A→2.9 min 30% A→3.1 min 10% A→4.5 min 10% A; oven: 55° C., flow rate: 0.8 ml/min, UV detection: 208-400 nm.

Method 3 (LC/MS)

Instrument: Finnigan MAT 900S, TSP: P4000, AS3000, UV3000HR; column: Symmetry C 18, 150 mm×2.1 mm, 5.0 µm; mobile phase C: water, mobile phase B: water+0.3 g 35% strength hydrochloric acid, mobile phase A: acetonitrile; gradient: 0.0 min 2% A→2.5 min 95% A→5 min 95% A; Oven: 70° C.; flow rate: 1.2 ml/min; UV detection: 210 nm.

Method 4 (LC/MS)

Instrument: Micromass Quattro LCZ, HP1100; column: Symmetry C18, 50 mm×2.1 mm, 3.5 µm; mobile phase A: acetonitrile+0.1% formic acid, mobile phase B: water+0.1% formic acid; gradient: 0.0 min 10% A→4.0 min 90% A→6.0 min 90% A; oven: 40° C.; flow rate: 0.5 ml/min; UV detection: 208-400 nm.

Method 5 (LC/MS)

Instrument: Micromass Quattro LCZ with HPLC Agilent Series 1100; column: UPTISPHERE HDO, 50 mm×2.0 mm, 3 µm; mobile phase A: 1 l water+1 ml 50% strength formic acid, mobile phase B: 1 l acetonitrile+1 ml 50% strength formic acid; gradient: 0.0 min 100% A→0.2 min 100% A→2.9 min 30% A→3.1 min 10% A→4.5 min 10% A; Oven: 55° C., Flow rate: 0.8 ml/min, UV detection: 208-400 nm.

Method 6 (LC/MS)

Instrument MS: Micromass ZQ; instrument HPLC: Waters Alliance 2790; column: Uptisphere C 18, 50 mm×2.0 mm, 3.0 µm; mobile phase B: acetonitrile+0.05% formic acid, mobile phase A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 7 (HPLC)

Instrument: HP 1100 with DAD detection; column: Kromasil RP-18, 60 mm×2 mm, 3.5 µm; mobile phase A: 5 ml $HClO_4$/l water, mobile phase B: acetonitrile; gradient: 0 min 2% B, 0.5 min 2% B, 4.5 min 90% B, 6.5 min 90% B; flow rate: 0.75 ml/min; temp.: 30° C.; UV detection: 210 nm.

Method 8 (LC/MS)

Instrument MS: Micromass ZQ; instrument HPLC: Waters Alliance 2790; column: Grom-Sil 120 ODS-4 HE 50 mm×2 mm, 3.0 µm; mobile phase B: acetonitrile+0.05% formic acid, mobile phase A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 9 (LC/MS)

Instrument: Micromass Quattro LCZ, with HPLC Agilent Series 1100; column: Grom-SIL120 ODS-4 HE, 50 mm×2.0 mm, 3 µm; mobile phase A: 1 l water+1 ml 50% strength formic acid, mobile phase B: 1 l acetonitrile+1 ml 50% strength formic acid; gradient: 0.0 min 100% A→0.2 min 100% A→2.9 min 30% A→3.1 min 10% A→-4.5 min 10% A; oven: 55° C., flow rate: 0.8 ml/min, UV detection: 208-400 nm.

Method 10 (LC/MS)

Instrument MS: Micromass ZQ; instrument HPLC: HP 1100 Series; UV DAD; column: Grom-Sil 120 ODS-4 HE 50 mm×2 mm, 3.0 µm; mobile phase A: water+500 g 50% strength formic acid/l, mobile phase B: acetonitrile+500 µl 50% strength formic acid/l; gradient: 0.0 min 0% B→2.9 min 70% B→3.1 min 90% B→4.5 min 90% B; oven: 50° C., flow rate: 0.8 ml/min, UV detection: 210 nm.

Method 11 (HPLC)

Instrument: HP 1100 with DAD detection; column: Kromasil RP-18, 60 mm×2 mm, 3.5 µm; mobile phase A: 5 ml $HClO_4$/l water, mobile phase B: acetonitrile; gradient: 0 min 2% B, 0.5 min 2% B, 4.5 min 90% B, 9 min 90% B; flow rate: 0.75 ml/min, temp.: 30° C., UV detection: 210 nm.

Method 12 (LC/MS)

Instrument: Micromass Platform LCZ with HPLC Agilent Series 1100; column: Grom-SIL120 ODS-4 HE, 50 mm×2.0 mm, 3 µm; mobile phase A: 1 l water+1 ml 50% strength formic acid, mobile phase B: 1 l acetonitrile+1 ml 50% strength formic acid; gradient: 0.0 min 100% A→0.2 min 100% A→2.9 min 30% A→3.1 min 10% A→4.5 min 10% A; oven: 55° C., flow rate: 0.8 ml/min, UV detection: 210 nm.

Method 13 (LC/MS)

Instrument MS: Micromass ZQ; instrument HPLC: HP 1100 Series; UV DAD; column: Phenomenex Synergi 2µ Hydro-RP Mercury 20 mm×4 mm; mobile phase A: 1 l water+0.5 ml 50% strength formic acid, mobile phase B: 1 l acetonitrile+0.5 ml 50% strength formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 14 (LC/MS)

Instrument: Micromass Quattro LCZ with HPLC Agilent Series 1100; column: Phenomenex Synergi 2µ Hydro-RP Mercury 20 mm×4 mm; mobile phase A: 1 l water+0.5 ml 50% strength formic acid, mobile phase B: 1 l acetonitrile+0.5 ml 50% strength formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 208-400 nm.

Method 15 (LC/MS)

Instrument MS: Micromass ZQ; instrument HPLC: Waters Alliance 2795; column: Phenomenex Synergi 2μ Hydro-RP Mercury 20 mm×4 mm; mobile phase A: 1 l water+0.5 ml 50% strength formic acid, mobile phase B: 1 l acetonitrile+ 0.5 ml 50% strength formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 16 (LC/MS)

Instrument MS: Micromass ZQ; instrument HPLC: Waters Alliance 2795; column: Merck Chromolith SpeedROD RP-18e 50 mm×4.6 mm; mobile phase A: water+500 μl 50% strength formic acid/l; mobile phase B: acetonitrile+500 μl 50% strength formic acid/l; gradient: 0.0 min 10% B→3.0 min 95% B→4.0 min 95% B; oven: 35° C.; flow rate: 0.0 min 1.0 ml/min, 3.0 min 3.0 ml/min, 4.0 min 3.0 ml/min; UV detection: 210 nm.

Method 17 (LC/MS)

Instrument: Micromass Platform LCZ with HPLC Agilent Series 1100; column: Phenomenex Synergi 2μ Hydro-RP Mercury 20 mm×4 mm; mobile phase A: 1 l water+0.5 ml 50% strength formic acid, mobile phase B: 1 l acetonitrile+ 0.5 ml 50% strength formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 18 (LC/MS)

Instrument MS: Micromass ZQ; instrument HPLC: HP 1100 Series; UV DAD; column: Grom-Sil 120 ODS-4 HE 50 mm×2 mm, 3.0 μm; mobile phase A: water+500 μl 50% strength formic acid/l, mobile phase B: acetonitrile+500 μl 50% strength formic acid/l; gradient: 0.0 min 70% B→4.5 min 90% B; oven: 50° C., flow rate: 0.8 ml/min, UV detection: 210 nm.

Preparative HPLC

Column: YMC Gel ODS-AQ S-5/15 μM, 250 mm×30 mm, mobile phase A: water, mobile phase B: acetonitrile; gradient: 0.00 min 30% B→3.00 min 30% B→34.0 min 95% B→38.0 min 30% B; temp.: room temperature; Flow rate: 50 ml/min; UV detection.

Starting Materials

Example I

3-Methyl-1H-indazol-4-ol

526 mg (10.5 mmol) of hydrazine hydrate and 1 ml of glacial acetic acid are added to 800 mg (5.26 mmol) of 2,6-dihydroxyacetophenone. After 15 minutes of stirring at 110° C., the reaction mixture is cooled to room temperature. After addition of 6 ml of polyphosphoric acid, the mixture is heated at 120° C. for 20 min. After cooling to room temperature, 0.8 g (7.89 mmol) of acetic anhydride is added dropwise. The mixture is once more heated at 120° C. for 20 min. The reaction mixture, cooled to room temperature, is then poured onto ice. The mixture is neutralized using 1N sodium hydroxide solution and extracted three times with ethyl acetate. The combined organic phases are washed twice with water. After drying over sodium sulfate, the solvent is removed under reduced pressure. The product is purified by column chromatography. The mobile phase used is a mixture of cyclohexane and ethyl acetate (1:1).

Yield: 429 mg (55%)

LC-MS (Method 1): $R_f$=1.8 min

MS (ESI pos.): m/z=149 (M+H)$^+$ $^1$H-NMR (DMSO-$d_6$, 300 MHz): δ=2.54 (s, 3H), 6.31 (d, 1H), 6.79 (d, 1H), 7.02 (t, 1H), 9.84 (s, 1H), 12.3 (s, 1H).

Example II 4-(2-Fluoro-4-nitrophenoxy)-3-methyl-1H-indazole

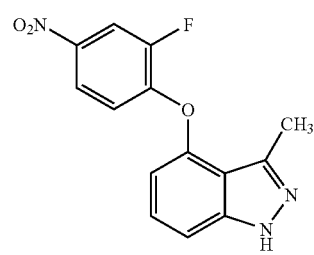

100 mg (0.63 mmol) of 3,4-difluoronitrobenzene, 93.1 mg (0.63 mmol) of 3-methyl-1H-indazol-4-ol (from example I) and 95.6 mg (0.69 mmol) of potassium carbonate are suspended in 5 ml of anhydrous dimethylformamide and stirred at 50° C. for five hours. The reaction solution is then diluted with water and extracted twice with ethyl acetate. The combined organic phases are dried over sodium sulfate. The solvent is removed under reduced pressure and the residue is purified by column chromatography. The mobile phase used is a mixture of cyclohexane and ethyl acetate (1:1).

Yield: 93 mg (51.5%)

LC-MS (Method 2): $R_f$=3.7 min

MS (ESI pos.): m/z=288 (M+H)$^+$ $^1$H-NMR (DMSO-$d_6$, 300 MHz): δ=2.36 (s, 3H), 6.73 (dd, 1H), 7.07 (t, 1H), 7.37 (m, 2H), 8.06 (m, 1H), 8.37 (dd, 1H), 13.06 (s, 1H).

Example III

3-Fluoro-4-[(3-methyl-1H-indazol-4-yl)oxy]phenylamine

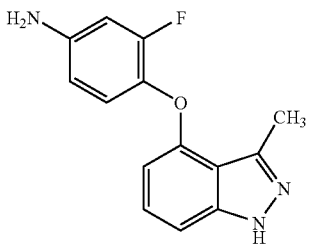

75 mg (0.26 mmol) of 4-(2-fluoro-4-nitrophenoxy)-3-methyl-1H-indazole (from example II) are dissolved in 3 ml of ethanol, and 261 mg (5.22 mmol) of hydrazine hydrate and 10 mg of 10% palladium on activated carbon are added. The mixture is heated at 80° C. for two hours and then filtered through kieselguhr. The filtrate is concentrated under reduced pressure.

Yield: 65 mg (96.8%)

LC-MS (Method 5): $R_t$=3.23 min

MS (ESI pos.): m/z=258 (M+H)$^+$ $^1$H-NMR (DMSO-d$_6$, 300 MHz): δ=2.61 (s, 3H), 5.32 (s, 2H), 6.06 (d, 1H), 6.41 (dd, 1H), 6.52 (dd, 1H), 6.96 (t, 1H), 7.08 (m, 2H), 12.63 (s, 1H).

Example IV

4-Methoxy-1,2-benzisoxazole-3-amine

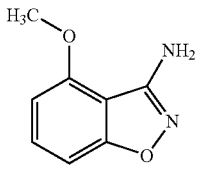

709.5 mg (9.45 mmol) of acetohydroxamic acid are initially charged in 8 ml of anhydrous dimethylformamide, and 1.06 g (9.45 mmol) of potassium tert-butoxide are added at room temperature. After 40 minutes of stirring, 1 g (6.62 mmol) of 2-fluoro-6-methoxybenzonitrile is added. The mixture is heated at 60° C. for 16 hours. 20 ml of saturated sodium chloride solution are then added to the reaction mixture. The precipitated crystals are filtered off with suction and washed with water.

Yield: 358 mg (23%)

LC-MS (Method 6): $R_t$=2.59 min

MS (ESI pos.): m/z=165 (M+H)$^+$ $^1$H-NMR (DMSO-d$_6$, 300 MHz): δ=3.91 (s, 3H), 5.91 (s, 2H), 6.71 (d, 1H), 6.98 (d, 1H), 7.43 (t, 1H).

Example V

3-Amino-1,2-benzisoxazol-4-ole

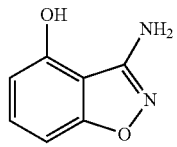

250 mg (1.52 mmol) of 4-methoxy-1,2-benzisoxazole-3-amine (from example IV) are dissolved in 5 ml of absolute methylene chloride, and 7.6 ml (7.6 mmol) of a 1M solution of boron tribromide in methylene chloride are added under argon. The mixture is stirred at room temperature overnight and then carefully hydrolyzed with water. The precipitate is filtered off, washed with water and dried under high vacuum.

Yield: 195 mg (85.3%)

LC-MS (Method 6): $R_t$=1.78 min

MS (ESI pos.): m/z=151 (M+H)$^+$ $^1$H-NMR (DMSO-d$_6$, 300 MHz): δ=5.90 (s, 2H), 6.70 (d, 1H), 6.97 (d, 1H), 7.42 (t, 1H).

Example VI

4-(2-Fluoro-4-nitrophenoxy)-1,2-benzisoxazole-3-amine

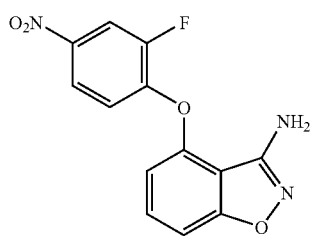

94.37 mg (0.63 mmol) of 3-amino-1,2-benzisoxazol-4-ol (from example V), 100 mg (0.63 mmol) of 3,4-difluoronitrobenzene and 95.56 mg (0.69 mmol) of potassium carbonate are suspended in 3 ml of anhydrous dimethylformamide and stirred at room temperature for 16 hours. The reaction solution is then diluted with water, and the precipitate is filtered off. The product is dried under high vacuum.

Yield: 151 mg (83.1%)

LC-MS (Method 2): $R_t$=3.5 min

MS (ESI pos.): m/z=290 (M+H)$^+$ $^1$H-NMR (DMSO-d$_6$, 300 MHz): δ=6.15 (s, 2H), 6.64 (d, 1H), 7.28 (d, 1H), 7.49 (m, 2H), 8.14 (m, 1H), 8.39 (dd, 1H).

Example VII

4-(4-Amino-2-fluorophenoxy)-1,2-benzisoxazole-3-amine

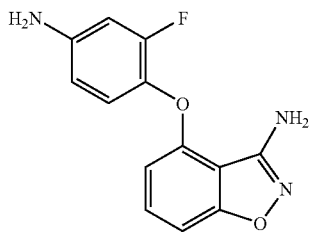

120 mg (0.41 mmol) of 4-(2-fluoro-4-nitrophenoxy)-1,2-benzisoxazole-3-amine (from example VI) and 468 mg (2.07 mmol) of tin(II) chloride dihydrate are dissolved in 8 ml of ethyl acetate and heated at 70° C. for 4 hours. After cooling to room temperature, the reaction solution is adjusted to pH 9 using saturated sodium bicarbonate solution, which gives a colorless precipitate. 5 g of kieselguhr are added to the suspension, and the mixture is filtered. The filtrate is extracted repeatedly with ethyl acetate. The combined organic phases are washed with water and dried over sodium sulfate. Removal of the solvent under reduced pressure gives the product.

Yield: 102 mg (94.8%)
LC-MS (Method 2): $R_t$=2.95 min
MS (ESI pos.): m/z=260 (M+H)$^+$
$^1$H-NMR (DMSO-d$_6$, 300 MHz): δ=5.40 (s, 2H), 6.03 (s, 2H), 6.24 (d, 1H), 6.43 (m, 1H), 6.46 (dd, 1H), 7.04 (m, 2H), 7.34 (t, 1H).

Example VIII

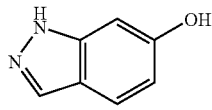

Dilute sulfuric acid (8 ml of concentrated sulfuric acid in 52.8 ml of H$_2$O) is added to 8.00 g (60.1 mmol) of 6-aminoindazole, and the mixture is cooled to 0° C. An aqueous sodium nitrite solution (4.48 g of sodium nitrite in 12.8 ml of water) is slowly added dropwise. The mixture is stirred at 0° C. for one hour. After addition of 5.60 g (90.6 mmol) of boric acid and a further 8 ml of dilute sulfuric acid, the mixture is heated under reflux for 15 minutes. The reaction solution is cooled and neutralized using 25% strength ammonia solution. The precipitated solid is filtered off with suction and boiled in water. The mixture is filtered hot. The filtrate is extracted repeatedly with ethyl acetate. The combined organic phases are dried over magnesium sulfate and concentrated.

Yield: 5.15 g (58%)
LC-MS (Method 2): $R_t$=2.25 min
MS (ESI pos.): m/z=134 (M+H)$^+$
$^1$H-NMR (DMSO-d$_6$, 200 MHz): δ=6.62 (dd, 1H), 6.77 (d, 1H), 7.51 (d, 1H), 7.88 (s, 1H), 9.63 (s, 1H), 12.58 (s, 1H).

Example IX

5-(2-Fluoro-4-nitrophenoxy)-1H-indazole

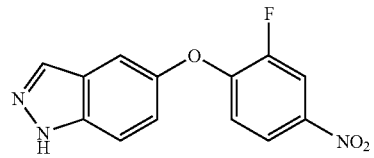

5.00 g (37.3 mmol) of 5-hydroxyindazole are dissolved in 40 ml of anhydrous DMF. 5.93 g (37.3 mmol) of 3,4-difluoronitrobenzene and 5.15 g (37.3 mmol) of potassium carbonate are added, and the mixture is stirred at 40° C. overnight. For work-up, the mixture is filtered off with suction through kieselguhr, diluted with water and extracted three times with ethyl acetate. The combined organic phases are washed 1× with saturated aqueous sodium chloride solution, dried over sodium sulfate and concentrated using a rotary evaporator. The residue is chromatographed twice on silica gel using cyclohexane/ethyl acetate 3:1→1:1→1:2 and then purified by preparative HPLC.

Yield: 4.02 g (39%)
MS (ESI pos.): m/z=274 (M+H)$^+$
$^1$H-NMR (DMSO-d$_6$, 300 MHz): δ=6.98 (t, 1H), 7.22 (dd, 1H), 7.58-7.69 (m, 2H), 7.95-8.12 (m, 2H), 8.33 (dd, 1H), 13.20-13.36 (br. s, 1H).

The following compounds are prepared in an analogous manner:

| Ex. No. | Structure | MS (ESI pos.) | HPLC |
|---|---|---|---|
| X | ![structure] | m/z = 290 (M + H)$^+$ | Method 7: $R_t$ = 4.56 min |
| XI | ![structure] | m/z = 274 (M + H)$^+$ | Method 7: $R_t$ = 4.40 min |

Example XII 5-(4-Amino-2-fluorophenoxy)-1H-indazole

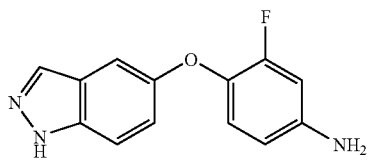

1.96 g (7.17 mmol) of 5-(2-fluoro-4-nitrophenoxy)-1H-indazole (from example IX) are dissolved in 50 ml of ethanol. 0.16 g (0.71 mmol) of platinum(IV) oxide are added, and the mixture is hydrogenated at room temperature under atmospheric pressure for two hours. For work-up, the mixture is filtered off with suction through kieselguhr, the filtercake is washed with ethanol and the filtrate is concentrated.

Yield: 1.66 g (95%)
MS (ESI pos.): m/z=244 (M+H)$^+$
$^1$H-NMR (DMSO-d$_6$, 300 MHz): δ=5.26 (s, 2H), 6.39 (dd, 1H), 6.49 (dd, 1H), 6.88 (t, 1H), 7.00 (d, 1H), 7.08 (dd, 1H), 7.48 (d, 1H), 7.90 (s, 1H), 12.83-13.04, (br. s, 1H).

The following compounds are prepared in an analogous manner:

the precipitate formed is added. The mixture is filtered through silica gel (mobile phase: dichloromethane/methanol 95:5) and the product fractions are dried after concentration under high vacuum.

Yield: 145 g (75%)
HPLC (Method 7): R$_t$=2.02 min
MS (ESI pos.): m/z=135 (M+H)$^+$, 152 (M+NH4)$^+$, 269 (2M+H)+
$^1$H-NMR (DMSO-d$_6$, 200 MHz): δ=6.58 (d, 1H), 7.07 (dd, 1H), 7.48 (d, 1H), 7.65 (d, 1H), 8.17 (d, 1H), 12.42-12.64 (br. s, 1H).

Example XVI

4-Nitro-1H-pyrrolo[2,3-b]pyridine 7-oxide

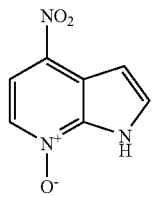

| Ex. No. | Structure | MS (ESI pos.) | HPLC/LC-MS |
|---|---|---|---|
| XIII | 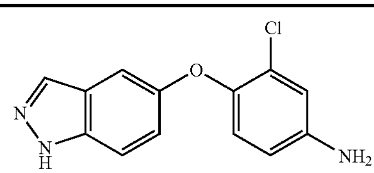 | m/z = 260 (M + H)$^+$ | HPLC: Method 7: R$_t$ = 3.45 min |
| XIV | 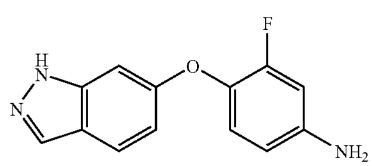 | m/z = 243 (M + H)$^+$ | LC-MS Method 8: R$_t$ = 2.87 min |

Example XV

1H-Pyrrolo[2,3-b]pyridine 7-oxide

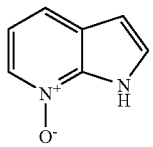

539.7 g (2.35 mol) of 3-chloroperbenzoic acid are dissolved in 6.11 l of dichloromethane, and water that separates off is removed. The organic phase is dried over sodium sulfate and cooled to 0° C. A solution of 163 g (1.38 mol) of 1H-pyrrolo[2,3-b]pyridine in 1.00 l of dichloromethane is then added, and the temperature is allowed to increase to room temperature. After 2 hours, sufficient methanol to re-dissolve Based on the results of differential thermal analysis, it is not recommended to carry out the reaction on a scale larger than that described below.

A solution of 20.0 g (149 mmol) of 1H-pyrrolo[2,3-b]pyridine 7-oxide (from example XV) in 160 ml of trifluoroacetic acid is cooled to room temperature. 69.3 ml of 65% strength nitric acid are then slowly added dropwise, and the mixture is stirred at room temperature overnight. The mixture is poured onto ice and the pH is adjusted to 8-9 using 45% strength sodium hydroxide solution. The precipitate is filtered off with suction and washed with water. The cooled products of four batches of the size described above and a 13 g batch carried out analogously are combined and jointly purified. The crude products are suspended in water and adjusted to pH 8-9 using 2N sodium hydroxide solution. After 10 min of stirring, the precipitate is filtered off with suction and dried under high vacuum.

Yield: 29.7 g (24%)
HPLC (Method 7): R$_t$=3.02 min

MS (ESI pos.): m/z=180 (M+H)+, 197 (M+NH4)+, 359 (2M+H)+

¹H-NMR (DMSO-d₆, 200 MHz): δ=7.03 (d, 1H), 7.80 (d, 1H), 8.03 (d, 1H), 8.31 (d, 1H), 13.22-13.41 (br. s, 1H).

Example XVII

4-Amino-1H-pyrrolo[2,3-b]pyridine

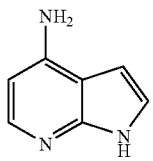

9.35 g (167 mmol) of iron powder are added to a solution of 3.00 g (16.8 mmol) of 4-nitro-1H-pyrrolo[2,3-b]pyridine 7-oxide (from example (XVI) in 225 ml of acetic acid, and the mixture is heated under reflux for 2 hours. The crude mixtures of two such batches are combined and jointly worked up further. The solid is separated off and washed with 50 ml of acetic acid and 100 ml of tetrahydrofuran. Using a rotary evaporator, the filtrate is concentrated to dryness. The residue is diluted with 50 ml of water and the solution is made alkaline using 45% strength sodium hydroxide solution. Dichloromethane is then added, and the mixture is filtered off with suction through kieselguhr. The filtrate is extracted six times with in each case 100 ml of dichloromethane and the organic phase is dried over sodium sulfate and evaporated to dryness using a rotary evaporator. The residue is dried under high vacuum. For further purification, the residue is triturated with tetrahydrofuran and the solid is filtered off with suction. The filtrate is concentrated and the residue is taken up in dichloromethane, dried and concentrated.

Yield: 3.5 g (78%)

MS (ESI pos.): m/z=134 (M+H)+, 267 (2M+H)+

¹H-NMR (DMSO-d₆, 200 MHz): δ=6.05 (s, 2H), 6.09 (d, 1H), 6.47 (d, 1H), 7.02 (d, 1H), 7.70 (d, 1H), 10.90-11.28 (br. s, 1H).

Example XVIII

4-Chloro-1H-pyrrolo[2,3-b]pyridine

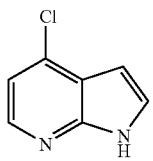

750 mg (5.63 mmol) of 4-amino-1H-pyrrolo[2,3-b]pyridine (from example XVII) are dissolved in a mixture of 67.5 ml of glacial acetic acid and 0.67 ml of concentrated sulfuric acid. The mixture is cooled to 12° C. 3.67 ml (3.20 g, 117 mmol) of isopentyl nitrite are slowly added dropwise, and the mixture is stirred at 12° C. for 3 hours. This solution is then added to a suspension (temperature: 50° C.) of 6.07 g (61.4 mmol) of copper(I) chloride in 34 ml of concentrated hydrochloric acid, and the mixture is then heated at 80-90° C. for 30 min. The mixture is cooled to RT and stirred overnight. For work-up, the reaction solution is concentrated and made alkaline using 1N aqueous sodium hydroxide solution, the precipitated copper salts are filtered off with suction through kieselguhr and the mixture is extracted 3× with ethyl acetate. The organic phase is dried over magnesium sulfate and concentrated using a rotary evaporator.

Yield: 548 mg (64%)

LC-MS (Method 5): R_t=3.21 min

MS (ESI pos.): m/z=153 (M+H)+

¹H-NMR (DMSO-d₆, 200 MHz): δ=6.44-6.55 (m, 1H), 7.20 (d, 1H), 7.60 (t, 1H), 8.10-8.27 (m, 1H), 12.05 (br. s, 1H).

Alternatively, the compound described above (example XVIII) can also be prepared by the process below:

Example XVIII

Alternative Preparation Method

4-Chloro-1H-pyrrolo[2,3-b]pyridine

100 mg (0.76 mmol) of 1H-pyrrolo[2,3-b]pyridine 7-oxide (from example XV) in 3 ml of phosphorus oxychloride are heated at reflux until a clear solution is formed. After cooling to room temperature, the reaction mixture is carefully hydrolyzed with ice. The mixture is made alkaline using ammonia and extracted repeatedly with ethyl acetate. The organic phase is washed with water and saturated sodium chloride solution. After drying over magnesium sulfate, the solvent is removed under reduced pressure. This gives a yellow oil which is purified by preparative HPLC.

Yield: 210 mg (73%)

LC-MS (Method 8): R_t=2.9 min

MS (ESI pos.): m/z=153 (M+H)+

¹H-NMR (DMSO-d₆, 300 MHz): δ=6.51 (dd, 1H), 7.20 (d, 1H), 7.60 (t, 1H), 8.17 (d, 1H), 12.05 (s, 1H).

Example XIX

3-Fluoro-4-(1H-pyrrolo[2,3-b]pyridin-4-yloxy)aniline

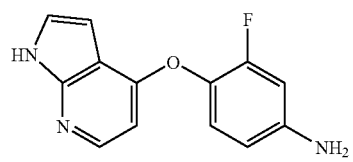

543 mg (3.56 mmol) of 4-chloro-1H-pyrrolo[2,3-b]pyridine (from example XVIII, 905 mg (7.12 mmol) of 3-fluoro-4-hydroxyaniline and 399 mg (7.12 mmol) of powdered potassium hydroxide are heated at 260° C. for 8 hours. Another 905 mg (7.12 mmol) of 3-fluoro-4-hydroxyaniline and 200 mg (3.56 mmol) of powdered potassium hydroxide are added, and the mixture is reacted at 260° C. for another 8 h. For work-up, the mixture is cooled to room temperature, diluted with water and extracted three times with ethyl acetate. The organic phase is dried over magnesium sulfate and concentrated using a rotary evaporator. The residue is purified by preparative HPLC. The fractions which, according to LC-MS, contain 39% of product are used without further purification for the next reaction.

Alternatively, the compound described above (example XIX) can also be prepared by the process described below:

Example XIX

Alternative Preparation Method

3-Fluoro-4-(1H-pyrrolo[2,3-b]pyridin-4-yloxy)aniline

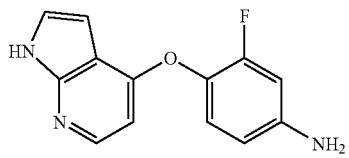

3.2 g (11.5 mmol) of {4-[(6-chloro-1H-pyrrolo[2,3-b]pyridin-4-yl)oxy]-3-fluoro-phenyl}amine (from example XXXI) are dissolved in ethanol at 50° C. The solution is then allowed to cool to RT, and 2.45 g (2.30 mmol) of 10% palladium on activated carbon are added. The mixture is hydrogenated overnight under a hydrogen pressure of 2 bar. The palladium is then filtered off with suction through kieselguhr and washed with ethanol, and the filtrate is concentrated.

Yield: 2.5 g (89%)
LC-MS (Method 8): $R_t$=2.43 min
MS (ESI pos.): m/z=244 (M+H)$^+$
$^1$H-NMR (DMSO-$d_6$, 200 MHz): δ=5.45 (mc, 2H), 6.25 (mc, 2H), 6.40-6.55 (br. 2H), 7.05 (t, 1H), 7.33 (mc, 1H), 8.25 (d, 1H), 11.69 (s, 1H).

Example XX

2-Fluoro-4-(1H-pyrrolo[2,3-b]pyridin-4-yloxy)aniline

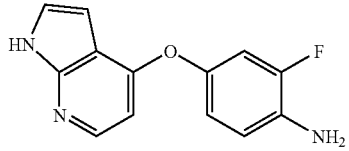

100 mg (660 μmol) of 4-chloro-1H-pyrrolo[2,3-b]pyridine (from example XVIII), 166 mg (1.31 mmol) of 2-fluoro-4-hydroxyaniline and 73.5 mg (1.31 mmol) of powdered potassium hydroxide are heated at 260° C. for 8 hours. For work-up, the mixture is cooled to room temperature, diluted with water and extracted three times with ethyl acetate. The organic phase is dried over magnesium sulfate and concentrated using a rotary evaporator. The residue is purified by preparative HPLC.

Yield: 11 mg (6.7%)
LC-MS (Method 6): $R_t$=2.37 min

Example XXI

1-Benzofuran-4-ol

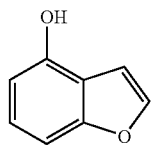

3.76 g (27.6 mmol) of 6,7-dihydro-1-benzofuran-4(5H)-one (prepared according to *Tetrahedron Lett.* 1994, 35, 6231) and 10% of palladium on activated carbon in 34 ml of decalin and 6 ml of dodecene are heated in a metal bath at 200° C. overnight. The mixture is cooled to 80° C., ethanol is added and the mixture is filtered off through CELITE (diatomaceous earth). The CELITE (diatomaceous earth) is washed twice with ethanol and the filtrate is concentrated. The residue, which still contains decalin and dodecene, is mixed with petroleum ether and cooled in an ice bath. An oily precipitate forms. The solvent is decanted off and the oil is purified by preparative HPLC.

Yield: 180 mg (5%)
LC-MS (Method 5): $R_t$=3.1 min

Example XXII 4-(2-Fluoro-4-nitrophenoxy)-1-benzofuran

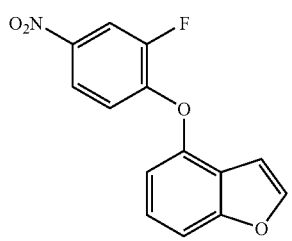

2.40 g (5.37 mmol) of 1-benzofuran-4-ol (from example XXI), 0.90 g (5.64 mmol) of 3,4-difluoronitrobenzene and 1.48 g (10.7 mmol) of potassium carbonate are suspended in 20 ml of anhydrous dimethylformamide, and the mixture is stirred at 50° C. for 5 hours. The reaction solution is then diluted with water and extracted twice with ethyl acetate. The combined organic phases are dried over sodium sulfate. The solvent is removed under reduced pressure. The crude product is purified on a silica gel column (mobile phase: cyclohexane:ethyl acetate (10:1)).

Yield: 254 mg (38%)
LC-MS (Method 6): $R_t$=4.14 min
MS (ESI pos.): m/z=291 (M+NH$_4$)$^+$

Example XXIII 4-(1-Benzofuran-4-yloxy)-3-fluorophenylamine

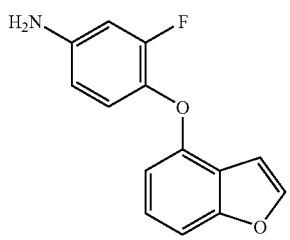

Under argon, 150 mg (0.55 mmol) of 4-(2-fluoro-4-nitrophenoxy)-1-benzofuran (from example XXII) are initially charged in 5 ml of ethanol/tetrahydrofuran (1:1), platinum (IV) oxide is added and the mixture is hydrogenated under atmospheric pressure for 2 hours. The suspension is filtered off through CELITE (diatomaceous earth), the filtercake is washed with ethanol and the filtrate is concentrated using a rotary evaporator.

Yield: 33 mg (25%)
LC-MS (Method 2): $R_f$=3.7 min
MS (ESI pos.): m/z=261 (M+NH$_4$)$^+$
$^1$H-NMR (DMSO-d$_6$, 200 MHz): δ=6.49 (m, 2H), 6.60 (d, 1H), 6.84 (dd, 1H), 7.00 (t, 1H), 7.24 (m, 2H), 7.95 (d, 1H).

Example XXIV

1H-Indazol-4-ol

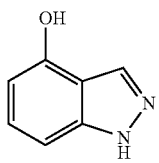

500 mg (375 mmol) of 1H-indazol-4-ylamine (prepared according to *J. Chem. Soc.* 1955, 2412, 2419) are stirred in 10% strength sulfuric acid at 180° C. in an autoclave at intrinsic pressure overnight. The reaction solution is cooled to room temperature and neutralized with 1N sodium hydroxide solution, and the salts are filtered off. The filtrate is concentrated to dryness.

Yield: 480 mg (95%)
LC-MS (Method 6): $R_f$=1.22 min
MS (ESI pos.): m/z=135 (M+H)$^+$
$^1$H-NMR (DMSO-d$_6$, 300 MHz): δ=6.38 (d, 1H), 6.92 (d, 1H), 7.11 (t, 1H), 8.0 (s, 1H), 9.8 (s, 1H), 12.8 (s, 1H).

Example XXV 4-(2-Fluoro-4-nitrophenoxy)-1H-indazole

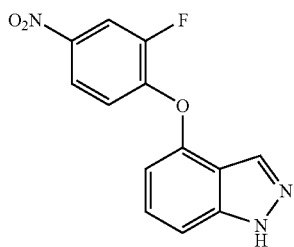

100 mg (0.75 mmol) of 1H-indazol-4-ol (from example XXIV), 94 mg (0.64 mmol) of 3,4-difluoronitrobenzene and 103 mg (0.75 mmol) of potassium carbonate are suspended in 2 ml of anhydrous dimethylformamide, and the mixture is stirred at 50° C. for 5 hours. The reaction solution is then diluted with water and extracted 2× with ethyl acetate. The combined organic phases are dried over sodium sulfate. The solvent is removed under reduced pressure. The crude product is purified by preparative HPLC.

Yield: 78 mg (38%)
LC-MS (Method 6): $R_f$=3.5 min
MS (ESI pos.): m/z=274 (M+H)$^+$
$^1$H-NMR (DMSO-d$_6$, 300 MHz): δ=6.79 (d, 1H), 7.20 (t, 1H), 7.41 (m, 2H), 7.94 (s, 1H), 8.07 (m, 1H), 8.36 (dd, 1H), 13.39 (s, 1H).

Example XXVI

3-Fluoro-4-(1H-indazol-4-yloxy)aniline

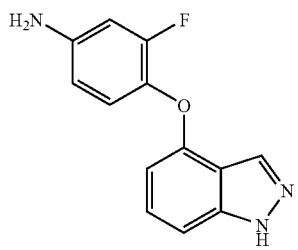

Under argon, 60 mg (0.22 mmol) of 4-(2-fluoro-4-nitrophenoxy)-1H-indazole (from example XXV) are initially charged in 5 ml of ethanol/tetrahydrofuran (1:1), 9.97 mg (0.04 mmol) of platinum(IV) oxide are added and the mixture is hydrogenated under atmospheric pressure for 2 hours. The suspension is filtered off through CELITE (diatomaceous earth), the filtercake is washed with ethanol and the filtrate is concentrated under reduced pressure.

Yield: 50 mg (94%)
LC-MS (Method 6): $R_f$=2.9 min
MS (ESI pos.): m/z=244 (M+H)$^+$
$^1$H-NMR (DMSO-d$_6$, 300 MHz): δ=5.36 (s, 2H), 6.24 (d, 1H), 6.42 (dd, 1H), 6.51 (dd, 1H), 7.0 (t, 1H), 7.17 (m, 2H), 7.88 (s, 1H), 13.13 (s, 1H).

Example XXVII

Ethyl 3-oxo-3-(4-pyridinyl)propanoate

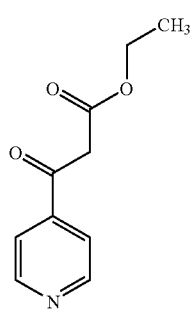

25 g (203 mmol) of isonicotinic acid, 35.12 g (243.7 mmol) of 2,2-dimethyl-1,3-dioxolane-4,6-dione and 49.6 g (406 mmol) of 4-dimethylaminopyridine are initially charged in 300 ml of dichloromethane, and the mixture is cooled to 0° C. A 1N solution of 46.1 g (223.4 mmol) of 1,3-dicyclohexylcarbodiimide in dichloromethane is added dropwise. The mixture is stirred at room temperature for 2 hours. The precipitate formed is filtered off and washed with dichloromethane. The filtrate is concentrated under reduced pressure. The residue is dissolved in 1200 ml of ethanol, a solution of 96.6 g (507.7 mmol) of p-toluenesulfonic acid monohydrate in 300 ml of ethanol is added and the mixture is stirred under reflux for one hour. After cooling, the ethanol is removed under reduced pressure. The residue is taken up in 1000 ml of ethyl acetate and 900 ml of water and dissolved by heating. The organic phase is separated off, washed with 600 ml of saturated sodium bicarbonate solution and saturated sodium chloride solution and dried over sodium sulfate. The mixture is concentrated under reduced pressure. The crude product is filtered through a silica gel frit using dichloromethane/methanol 10:1. Since there is still product present in the aqueous phase, it is extracted with dichloromethane and the extract is dried over sodium sulfate and concentrated under reduced pressure. The crude product is filtered through a silica gel frit using dichloromethane/methanol 10:1. This gives a total of 25.9 g (42% of theory) of product.

LC-MS (Method 3): $R_t$=2.40 min
MS (ESI pos): m/z=194 (M+H)$^+$
$^1$H-NMR (300 MHz, DMSO-d$_6$): δ=1.17 (t, 3H), 4.12 (q, 2H), 4.25 (s, 2H), 7.82 (dd, 2H), 8.83 (dd, 2H).

Example XXVIII

2-Amino-6-(4-pyridinyl)-4-pyrimidinol

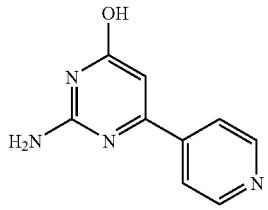

25 g (81.52 mmol) of the compound (from example XXVII) and 13.22 g (73.37 mmol) of guanidinium carbonate are dissolved in 250 ml of ethanol, 2.5 ml (29.76 mmol) of concentrated hydrochloric acid are added and the mixture is stirred under reflux overnight. After cooling, the precipitate is filtered off with suction, washed with ethanol and dried under high vacuum. 250 ml of 1N sodium hydroxide solution are added to the solid, and the mixture is stirred under reflux for 2 hours. After cooling, the mixture is acidified using concentrated acetic acid and the precipitated product is filtered off with suction and washed with diethyl ether. Drying under high vacuum gives 12.52 g (82% of theory) of product.

LC-MS (Method 4): $R_t$=0.30 min
MS (ESI pos): m/z=189 (M+H)$^+$
$^1$H-NMR (300 MHz, DMSO-d$_6$): δ=6.23 (s, 1H), 6.89 (br.s, 2H), 7.86 (dd, 2H), 8.64 (dd, 2H).

Example XXIX

4-Chloro-6-(4-pyridinyl)-2-pyrimidinamine

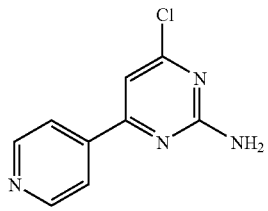

32 g (170.04 mmol) of the compound (from example XXVIII) are dissolved in 87.1 ml (0.93 mmol) of phosphoryl chloride. 2.80 ml (22.11 mmol) of N,N-dimethylaniline are slowly added dropwise, and the mixture is stirred at 100° C. for one hour. The reaction solution is then stirred at room temperature for another two hours. The phosphoryl chloride is removed under reduced pressure using a rotary evaporator. Water/dichloromethane 9:1 is added to the residue, which is then boiled for 5 minutes. The mixture is then neutralized using saturated sodium bicarbonate solution and the product is filtered off with suction and dried under high vacuum.

Yield: 18.8 g (48%)
LC-MS (Method 4): $R_t$=1.08 min
MS (ESI pos): m/z=207 (M+H)$^+$
$^1$H-NMR (300 MHz, DMSO-d$_6$): δ=7.31 (br.s, 2H), 7.38 (s, 1H), 8.00 (dd, 2H), 8.74 (dd, 2H).

Example XXX

6-Chloro-4-nitro-1H-pyrrolo[2,3-b]pyridine

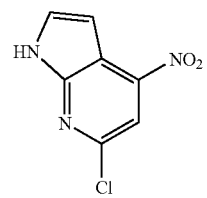

Under an atmosphere of argon, 5.00 g (27.9 mmol) of 4-nitro-1H-pyrrolo[2,3-b]pyridine 7-oxide (from example XVI) and 11.8 ml (55.8 mmol) of hexamethyldisilazane are initially charged in 290 ml of THF. At room temperature, 10.8 ml (139.6 mmol) of methyl chloroformate are added. The solution is stirred at RT overnight. The reaction solution is filtered through a silica gel cartridge, and is then washed with DCM/methanol 10:1.

Yield: 2.8 g (70%)
LC-MS (Method 8): $R_t$=2.74 min
MS (ESI pos.): m/z=198 (M+H)$^+$
$^1$H-NMR (DMSO-d$_6$, 200 MHz): δ=7.00 (mc, 1H), 7.97 (s, 1H), 8.00 (t, 1H), 12.79 (s, 1H).

Example XXXI

{4-[(6-Chloro-1H-pyrrolo[2,3-b]pyridin-4-yl)oxy]-3-fluorophenyl}amine

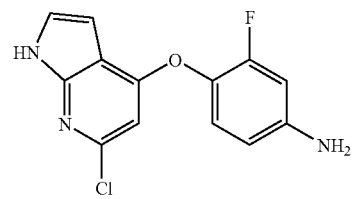

4-Amino-2-fluorophenol (0.77 g, 6.07 mmol) is dissolved in DMF. Potassium tert-butoxide (0.68 g, 6.07 mmol) is added, and the mixture is stirred at room temperature for 30 minutes. Powdered potassium carbonate (0.35 g, 2.53 mmol) and 1 g (5.06 mmol) of 6-chloro-4-nitro-1H-pyrrolo[2,3-b]pyridine (from example XXX) are then added successively. The mixture is stirred at 120° C. for 12 hours. After cooling, the mixture is diluted with ethyl acetate (200 ml). The suspension is filtered off with suction through Celite®, and the filtercake is washed with ethyl acetate. The solution is extracted successively with aqueous sodium bicarbonate solution and sodium chloride solution. The organic phase is dried over anhydrous magnesium sulfate and concentrated. The residue is purified by column chromatography (silica gel 60, mobile phase: DCM:acetone=5:1). This gives 0.95 g (67% of theory) of product.

LC-MS (Method 16): $R_t$=1.99 min
MS (ESI pos): m/z=278 (M+H)$^+$

Example XXXII

4-Amino-2,6-difluorophenol

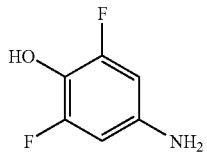

1.00 g (5.71 mmol) of 2,6-difluoro-4-nitrophenol (prepared by nitration of 2,6-difluorophenol according to Kirk, K. L.; *J. Heterocycl. Chem.* 1976, 13, 1253-1256) is initially charged in 35 ml of ethanol. 80 mg of palladium on carbon (10%) are added, and the mixture is hydrogenated under atmospheric pressure for 1.5 hours. With ice-cooling, 2 ml of conc. hydrochloric acid are added dropwise. The catalyst is filtered off and the solvent is removed under reduced pressure. The residue is suspended in diethyl ether and a little methanol. The suspension is filtered off with suction and the filtercake is washed with diethyl ether, giving the title compound (Qiu, Jian; Stevenson, Scott H.; O'Beirne, Michael J.; Silverman, Richard B.; *J. Med. Chem.* 1999, 42 (2), 329-332) as the hydrochloride.

Yield: 939 mg (91%)
LC-MS (Method 9): $R_t$=0.29 min
MS (ESI pos.): m/z=146 (M+H)$^+$
$^1$H-NMR (DMSO-d$_6$, 300 MHz): δ=6.89 (mc, 2H), 4.5-9.0 (br. s, 3H), 10.1 (br. s, 1H).

Example XXXIII

{4-[(6-Chloro-1H-pyrrolo[2,3-b]pyridin-4-yl)oxy]-3,5-difluorophenyl}amine

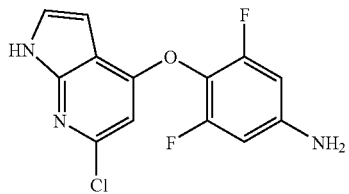

664 mg (3.36 mmol) of 6-chloro-4-nitro-1H-pyrrolo[2,3-b]pyridine (from example XXX), 1.39 g (10.1 mmol) of powdered potassium carbonate and 877 mg (5.04 mmol) of sodium dithionite are suspended in 10 ml of DMSO. The mixture is degassed, and 915 mg (5.04 mmol) of 4-amino-2,6-difluorophenol hydrochloride (from example XXXII) are added. The mixture is heated at 120° C. for 4 hours. After addition of ethyl acetate, the mixture is filtered off with suction through CELITE (diatomaceous earth) and the filtercake is washed with ethyl acetate. The filtrate is extracted three times with sat. sodium bicarbonate solution and with sat. sodium chloride solution. The filtrate is dried over sodium sulfate and the solvent is removed under reduced pressure. The residue is purified by column chromatography (silical gel 60, mobile phase: DCM:methanol=50:1).

Yield: 356 mg (36%)
HPLC (Method 7): $R_t$=4.12 min
MS (ESI pos.): m/z=296 (M+H)$^+$
$^1$H-NMR (DMSO-d$_6$, 400 MHz): δ=5.84 (s, 2H), 6.28 (mc, 1H), 6.38-6.41 (m, 3H), 7.42 (mc, 1H), 12.02 (s, 1H).

Example XXXIV

[3,5-Difluoro-4-(1H-pyrrolo[2,3-b]pyridin-4-yloxy)phenyl]amine

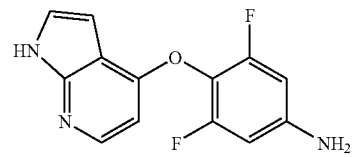

Analogously to example XIX (alternative method), the title compound is obtained by catalytic hydrogenation of 408 mg (1.38 mmol) of {4-[(6-chloro-1H-pyrrolo[2,3-b]pyridin-4-yl)oxy]-3,5-difluorophenyl}amine (from example XXXIII).

Yield: 360 mg (100%)
LC-MS (Method 10): $R_t$=2.19 min
MS (ESI pos.): m/z=262 (M+H)$^+$

Example XXXV 2-(4-Amino-2-chlorophenoxy)-6-fluorobenzonitrile

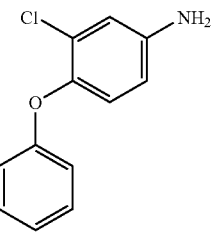

1.00 g (7.19 mmol) of 2,6-difluorobenzonitrile is initially charged in 10 ml of acetonitrile. 1.99 g (14.4 mmol) of potassium carbonate and 1.03 g (7.19 mmol) of 3-chloro-4-hydroxyaniline are added, and the mixture is heated at reflux for 45 min. The mixture is filtered and the filtercake is washed with ethyl acetate and DCM. The solvent is removed under reduced pressure and the residue is by column chromatography (silica gel 60, gradient column: mobile phase: DCM:petroleum ether=2:1, then DCM).

Yield: 1.13 g (60%)
HPLC (Method 7): $R_t$=4.04 min
MS (DCI): m/z=280 (M+NH$_4$)$^+$
$^1$H-NMR (DMSO-d$_6$, 200 MHz): δ=5.53 (br. s, 2H), 6.51 (d, 1H), 6.59 (dd, 1H), 6.76 (d, 1H), 7.10 (d, 1H), 7.17 (t, 1H), 7.65 (dt, 1H).

Example XXXVI 4-(4-Amino-2-chlorophenoxy)-1H-indazole-3-amine

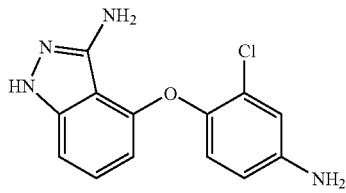

60 mg (0.23 mmol) of 2-(4-amino-2-chlorophenoxy)-6-fluorobenzonitrile (from example XXXV) and 17 mg (0.34 mmol) of hydrazine hydrate in 0.2 ml of 1-butanol are heated in a pressure vessel at 120° C. overnight. The solvent is then removed under reduced pressure and the residue is suspended in DCM and filtered off with suction.

Yield: 47 mg (73%)
HPLC (Method 7): $R_t$=3.05 min
MS (ESI pos.): m/z=275 (M+H)$^+$
$^1$H-NMR (DMSO-d$_6$, 200 MHz): δ=5.03 (br. s, 2H), 5.37 (br. s, 2H), 5.78 (d, 1H), 6.58 (dd, 1H), 6.74 (d, 1H), 6.82 (d, 1H), 6.96-7.05 (m, 2H), 11.52 (br. s, 1H).

Example XXXVII

3-Methyl-1H-pyrrolo[2,3-b]pyridine 7-oxide

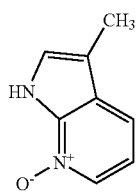

Analogously to example XV, the title compound is obtained by oxidation of 11 g (54.1 mmol) of 3-methyl-1H-pyrrolo[2,3-b]pyridine (Hands, D.; Bishop, B.; Cameron, M.; Edwards, T. S.; Cottrell, I. F.; Wright, S. H. B.; *Synthesis* 1996 (7), 877-882) using 24.2 g (108.2 mmol) of 3-chloroperbenzoic acid.

Yield: 5.4 g (67%)
LC-MS (Method 13): $R_t$=1.19 min
MS (ESI pos.): m/z=149 (M+H)$^+$
$^1$H-NMR (DMSO-d$_6$, 300 MHz): δ=2.25 (m, 3H), 7.05 (m, 1H), 7.21 (s, 1H), 7.59 (m, 1H), 8.10 (s, 1H), 12.06 (s, 1H).

Example XXXVIII

4-Chloro-3-methyl-1H-pyrrolo[2,3-b]pyridine

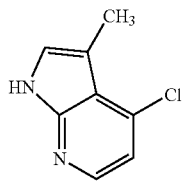

1.00 g (6.75 mmol) of 3-methyl-1H-pyrrolo[2,3-b]pyridine 7-oxide (from example XXXVII) is suspended in 5 ml of phosphoryl chloride. 2 ml of chloroform are then added, and the mixture is heated under reflux overnight. The mixture is allowed to cool to RT and poured into ethyl acetate/ice water. Solid sodium carbonate is then added. The phases are separated and the aqueous phase is washed with ethyl acetate. The organic phases are dried over sodium sulfate and concentrated. The residue is purified by column chromatography (silica gel 60, mobile phase: cyclohexane:methanol=4:1).

Yield: 200 mg (18%)
LC-MS (Method 13): $R_t$=2.05 min
$^1$H-NMR (DMSO-d$_6$, 200 MHz): δ=2.41 (m, 3H), 7.10 (d, 1H), 7.31 (s, 1H), 8.07 (d, 1H), 12.44 (s, 1H).

Example XXXIX

4-Chloro-3-methyl-1H-pyrrolo[2,3-b]pyridine 7-oxide

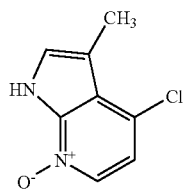

Analogously to example XV, the title compound is obtained by oxidation of 898 mg (5.39 mmol) of 4-chloro-3-methyl-1H-pyrrolo[2,3-b]pyridine (from example XXXVIII) using 2.42 g (10.78 mmol) of 3-chloroperbenzoic acid.

Yield: 688 mg (70%)
LC-MS (Method 13): $R_t$=1.75 min
MS (ESI pos.): m/z=183 (M+H)$^+$
$^1$H-NMR (DMSO-d$_6$, 200 MHz): δ=2.41 (m, 3H), 7.10 (d, 1H), 7.30 (s, 1H), 8.07 (d, 1H), 12.44 (s, 1H).

Example XL

1-Acetyl-4,6-dichloro-3-methyl-1H-pyrrolo[2,3-b]pyridine

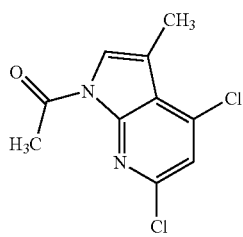

Analogously to example XXX, the title compound is obtained from 688 mg (3.77 mmol) of 4-chloro-3-methyl-1H-pyrrolo[2,3-b]pyridine 7-oxide (from example XXXIX) and 1.78 g (18.84 mmol) of methyl chloroformate and 0.61 g (3.77 mmol) of hexamethyldisilazane.

Yield: 420 mg (22%)
LC-MS (Method 13): $R_t$=2.44 min
MS (ESI pos.): m/z=259 (M+H)$^+$
$^1$H-NMR (DMSO-dr, 200 MHz): δ=3.99 (s, 3H), 2.40 (m, 3H), 7.61 (s, 1H), 7.77 (d, 1H).

Example XLI

{4-[(6-Chloro-3-methyl-1H-pyrrolo[2,3-b]pyridin-4-yl)oxy]-3-fluorophenyl}amine

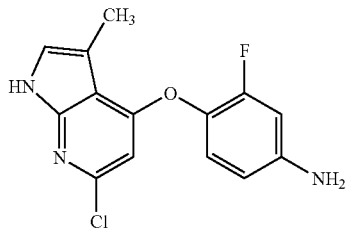

300 mg (1.16 mmol) of 1-acetyl-4,6-dichloro-3-methyl-1H-pyrrolo[2,3-b]pyridine (from example XL) and 320 mg (2.32 mmol) of powdered potassium carbonate are suspended in 9 ml of DMSO. The mixture is degassed, and 442 mg (3.48 mmol) of 4-amino-2-fluorophenol are added. The mixture is heated at 120° C. for 4 hours. After addition of ethyl acetate, the mixture is filtered off with suction through CELITE (diatomaceous earth) and the filtercake is washed with ethyl acetate. The filtrate is extracted three times with sat. sodium bicarbonate solution and with sat. sodium chloride solution. The filtrate is dried over sodium sulfate and the solvent is removed under reduced pressure. The residue is purified by column chromatography (silica gel 60, mobile phase: DCM:methanol=50:1).

Yield: 142 mg (42%)
LC-MS (Method 13): $R_t$=2.32 min
MS (ESI pos.): m/z=292 (M+H)$^+$

Example XLII

{3-Fluoro-4-[(3-methyl-1H-pyrrolo[2,3-b]pyridin-4-yl)oxy]phenyl}amine

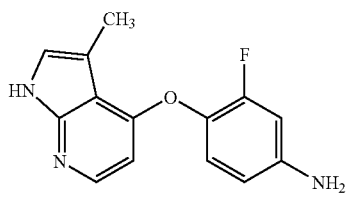

Analogously to example XIX (alternative method), the title compound is obtained by catalytic hydrogenation of 142 mg (0.49 mmol) of {4-[(6-chloro-3-methyl-1H-pyrrolo[2,3-b]pyridin-4-yl)oxy]-3-fluorophenyl}amine (from example XLI).

Yield: 125 mg (100%)
LC-MS (Method 13): $R_t$=1.58 min

The following compound is prepared analogously to example XLVII:

Example XLIV

N-[3-Fluoro-4-({1-[(4-methylphenyl)sulfonyl]-1H-pyrrolo[2,3-b]pyridin-4-yl}oxy)phenyl]-4-methylphenylsulfonamide

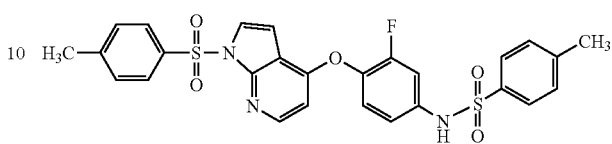

147 mg (0.60 mmol) of the compound from example XIX are dissolved in 10 ml of THF, 48 mg (1.21 mmol) of sodium hydride (in THF) are added and the mixture is then stirred at RT for one hour. 242 mg (1.27 mmol) of p-toluenesulfonyl chloride are then added, and the reaction solution is stirred at 60° C. for another hour. The suspension is filtered through CELITE (diatomaceous earth), the filtercake is washed with THF and a little DCM/methanol 10:1 and the filtrate is concentrated using a rotary evaporator. The residue in the flask is taken up in DMSO and purified by RP-HPLC chromatography (gradient: acetonitrile/water).

Yield: 94 mg (28%)
LC-MS (Method 15): $R_t$=2.72 min
$^1$H-NMR (DMSO-d$_6$, 300 MHz): δ=2.35 (s, 3H), 2.37 (s, 3H), 6.49-6.52 (m, 2H), 6.95 (m, 1H), 7.10 (m, 1H), 7.31 (t, 1H), 7.41 (m, 4H), 7.69 (m, 2H), 7.79 (d, 1H), 7.98 (d, 2H), 8.19 (d, 1H), 10.55 (s, 1H).

Example XLV

N-[3-Fluoro-4-({1-[(4-methylphenyl)sulfonyl]-2,3-dihydro-1H-pyrrolo[2,3-b]pyridin-4-yl}oxy)phenyl]-4-methylphenylsulfonamide

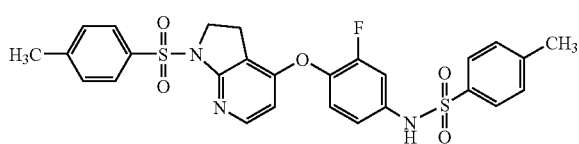

50 mg (0.09 mmol) of N-[3-fluoro-4-({1-[(4-methylphenyl)sulfonyl]-1H-pyrrolo[2,3-b]pyridin-4-yl}oxy)phenyl]-4-methylphenylsulfonamide (from example XLIV) are dis-

| Ex. No. | Structure | MS | HPLC, LC-MS |
|---|---|---|---|
| XLIII | 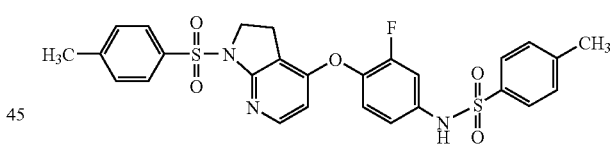 | MS (ESI pos.): m/z = 251 (M + H)$^+$ | LC-MS (Method 9): $R_t$ = 2.92 min. | solved in 30 ml of methanol, and 48.2 mg (0.05 mmol) of 10% palladium on activated carbon are added. The mixture is hydrogenated overnight under a hydrogen pressure of 3.5 bar. The palladium is then filtered off with suction through kieselguhr and washed with ethanol, and the filtrate is concentrated.

Yield: 48 mg (95%)
LC-MS (Method 9): $R_t$=3.35 min

Example XLVI

[4-(2,3-Dihydro-1H-pyrrolo[2,3-b]pyridin-4-yloxy)-3-fluorophenyl]amine

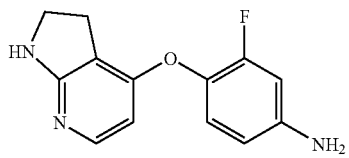

50 mg (0.09 mmol) of N-[3-fluoro-4-({1-[(4-methylphenyl)sulfonyl]-2,3-dihydro-1H-pyrrolo[2,3-b]pyridin-4-yl}oxy)phenyl]-4-methylphenylsulfonamide (from example XLV) are dissolved in 1.00 ml of sulfuric acid (95%) and stirred at RT overnight. With ice-cooling, the reaction solution is neutralized with 20% strength aqueous sodium hydroxide solution, and the mixture is extracted three times with ethyl acetate. The organic phase is dried over anhydrous magnesium sulfate and concentrated.

Yield: 20 mg (91%)
LC-MS (Method 8): $R_t$=2.22 min

Example XLVII

4-[(2-Amino-6-chloropyrimidin-4-yl)amino]benzonitrile

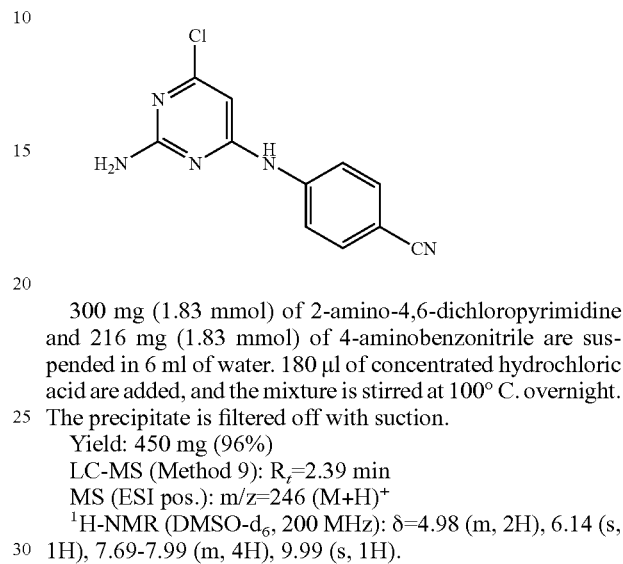

300 mg (1.83 mmol) of 2-amino-4,6-dichloropyrimidine and 216 mg (1.83 mmol) of 4-aminobenzonitrile are suspended in 6 ml of water. 180 µl of concentrated hydrochloric acid are added, and the mixture is stirred at 100° C. overnight. The precipitate is filtered off with suction.

Yield: 450 mg (96%)
LC-MS (Method 9): $R_t$=2.39 min
MS (ESI pos.): m/z=246 (M+H)$^+$
$^1$H-NMR (DMSO-d$_6$, 200 MHz): δ=4.98 (m, 2H), 6.14 (s, 1H), 7.69-7.99 (m, 4H), 9.99 (s, 1H).

The following compounds are prepared analogously to example XLVII:

| Ex. No. | Structure | MS | HPLC, LC-MS |
|---|---|---|---|
| XLVIII | 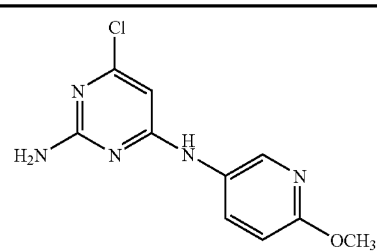 | | LC-MS (Method 9): $R_t$ = 2.09 min |
| XLIX | 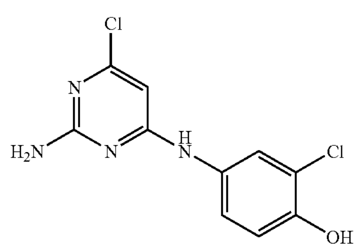 | MS (ESI pos.): m/z = 272 (M + H)$^+$ | LC-MS (Method 16): $R_t$ = 1.66 min |
| L | 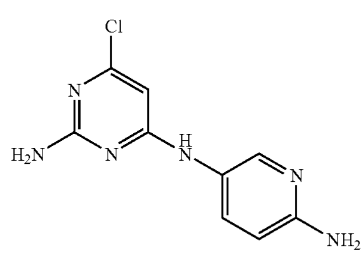 | MS (ESI pos.): m/z = 238 (M + H)$^+$ | LC-MS (Method 16): $R_t$ = 0.95 min |

| Ex. No. | Structure | MS | HPLC, LC-MS |
|---|---|---|---|
| LI | 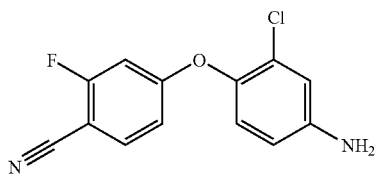 | MS (ESI pos.): m/z = 211 (M + H)+ | LC-MS (Method 10): R$_t$ = 2.10 min |

Example LII 4-(4-Amino-2-chlorophenoxy)-2-fluorobenzonitrile

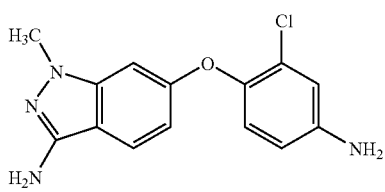

2.00 g (14.4 mmol) of 2,4-difluorobenzonitrile, 2.06 g (14.4 mmol) of 3-chloro-4-hydroxyaniline and 3.97 g (28.8 mmol) of potassium carbonate in 20 ml of acetonitrile are heated at RF for one hour. Ethyl acetate is added, the mixture is filtered and the solvent is removed under reduced pressure. The residue is purified by column chromatography (silica gel 60), giving the product which is a regioisomer mixture with a ratio of 62:38.

Yield: 2.55 g (68%)
HPLC (Method 7): R$_t$=3.90 min (major isomer), 4.01 min (minor isomer).
MS (ESI pos.): m/z=263 (M+H)+

Example LIII 6-(4-Amino-2-chlorophenoxy)-1-methyl-1H-indazole-3-amine

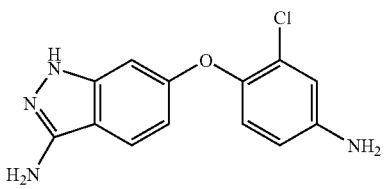

1.00 g (3.81 mmol) of 4-(4-amino-2-chlorophenoxy)-2-fluorobenzonitrile (contaminated by its regioisomer; from example LII) and 1.05 g (22.8 mmol) of methyl hydrazine in 4 ml of 1-butanol are heated at RF for 5 hours. Volatile components are removed under reduced pressure and the residue is purified by preparative HPLC.

Yield: 496 mg (45%)
HPLC (Method 7): R$_t$=3.26 min
MS (ESI pos.): m/z=289 (M+H)+

$^1$H-NMR (DMSO-d$_6$, 200 MHz): δ=3.57 (s, 3H), 5.33 (s, 2H), 5.37 (s, 2H), 6.47-6.59 (m, 3H), 6.72 (d, 1H), 6.91 (d, 1H), 7.58 (m, 1H).

Example LIV 6-(4-Amino-2-chlorophenoxy)-1H-indazole-3-amine

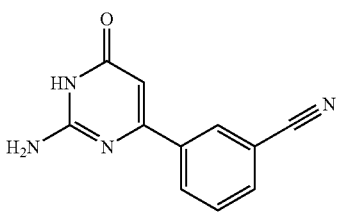

The title compound is synthesized analogously to example LIU from 2.3 g (8.76 mmol) of 4-(4-amino-2-chlorophenoxy)-2-fluorobenzonitrile (from example LII) and hydrazine hydrate.

Yield: 750 mg (31%)
HPLC (Method 7): R$_t$=3.24 min
MS (ESI pos.): m/z=275 (M+H)+
$^1$H-NMR (DMSO-d$_6$, 200 MHz): δ=5.29 (br. s, 2H), 5.35 (br. s, 2H), 6.30 (d, 1H), 6.53-6.62 (m, 2H), 6.73 (d, 1H), 6.94 (d, 1H), 7.59 (d, 1H), 11.06 (s, 1H).

Example LV 3-(2-Amino-6-oxo-1,6-dihydropyrimidin-4-yl)benzonitrile 12.0 g (49.8 mmol) of ethyl 3-(3-cyanophenyl)-3-oxopropanoate (Fevig, John M. et al.; Bioorg. Med. Chem. Lett. 2001, 11 (5), 641-646) are dissolved in 110 ml of ethanol. 5.39 g (29.9 mmol) of guanidinium carbonate and 0.95 ml of conc. hydrochloric acid are added, and the mixture is heated at RF overnight. The mixture is allowed to cool, and the precipitated crystals are filtered off with suction and washed with ethanol. This gives the title compound.

Yield: 8.02 g (76%)
HPLC (Method 7): $R_t$=2.99 min
MS (ESI pos.): m/z=213 (M+H)$^+$
$^1$H-NMR (DMSO-d$_6$, 200 MHz): δ=6.27 (s, 1H), 6.71 (br. s, 2H), 7.65 (t, 1H), 7.91 (d, 1H), 8.28 (d, 1H), 8.39 (s, 1H), 10.96 (s, 1H).

Example LVI 3-(2-Amino-6-chloropyrimidin-4-yl)benzonitrile

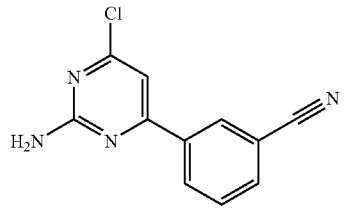

2.00 g (9.42 mmol) of 3-(2-amino-6-oxo-1,6-dihydropyrimidin-4-yl)benzonitrile (from example LV) are suspended in 10 ml of phosphoryl chloride. Over a period of one hour, 180 mg (1.23 mmol) of N,N-diethylaniline are added dropwise, and over a period of a further hour, the mixture is heated to 115° C. The mixture is then heated at RF for one hour. The mixture is allowed to cool to RT and poured into ice water. The mixture is extracted twice with ethyl acetate and the solvent is removed under reduced pressure. The residue is suspended in water. With ice-cooling, the solution is neutralized by addition of conc. sodium hydroxide solution. Saturated sodium carbonate solution is added, and the mixture is stirred at RT overnight. The precipitate is filtered off with suction and washed with water. This gives the title compound.

Yield: 1.58 g (73%)
LC-MS (Method 9): $R_t$=2.54 min
MS (ESI pos.): m/z=231 (M+H)$^+$
$^1$H-NMR (DMSO-d$_6$, 300 MHz): δ=7.27 (br. s, 2H), 7.41 (s, 1H), 7.73 (t, 1H), 8.00 (dt, 1H), 8.42 (dt, 1H), 8.53 (t, 1H).

The following compounds are prepared analogously to example LVI:

| Ex. No. | Structure | MS | HPLC, LC-MS |
|---|---|---|---|
| LVII | 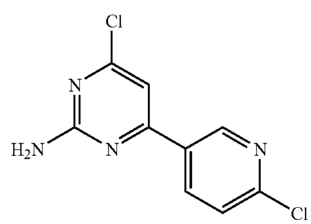 | MS (ESI pos.): m/z = 241 (M + H)$^+$ | LC-MS (Method 10): $R_t$ = 2.98 min |
| LVIII | 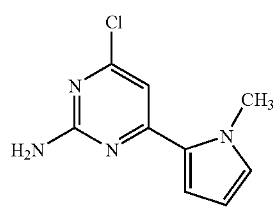 | MS (ESI pos.): m/z = 209 (M + H)$^+$ | LC-MS (Method 16): $R_t$ = 2.02 min |
| LIX | 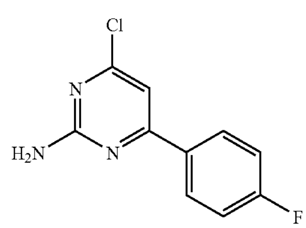 | MS (ESI pos.): m/z = 223 (M + H)$^+$ | LC-MS (Method 8): $R_t$ = 3.52 min |
| LX | 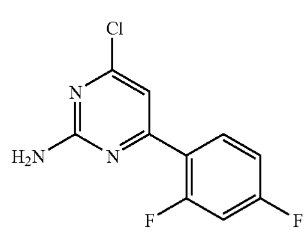 | MS (ESI pos.): m/z = 242 (M + H)$^+$ | HPLC (Method 7): $R_t$ = 4.38 min |

-continued

| Ex. No. | Structure | MS | HPLC, LC-MS |
|---|---|---|---|
| LXI | 4-(2-amino-6-chloropyrimidin-4-yl)-4-methoxyphenyl structure | MS (ESI pos.): m/z = 236 (M + H)+ | LC-MS (Method 10): R_t = 2.80 min |
| LXII | 4-(2-amino-6-chloropyrimidin-4-yl)benzonitrile structure | MS (ESI pos.): m/z = 231 (M + H)+ | LC-MS (Method 9): R_t = 2.54 min |
| LXIII | 2-amino-4-chloro-6-(pyridin-3-yl)pyrimidine structure | MS (ESI pos.): m/z = 207 (M + H)+ | LC-MS (Method 8): R_t = 2.12 min |
| LXIV | 2-amino-4-chloro-6-(6-methylpyridin-3-yl)pyrimidine structure | MS (ESI pos.): m/z = 221 (M + H)+ | LC-MS (Method 10): R_t = 2.15 min |
| LXV | 2-amino-4-chloro-6-(3-nitrophenyl)pyrimidine structure | MS (ESI pos.): m/z = 251 (M + H)+ | LC-MS (Method 2): R_t = 3.40 min |
| LXVI | 2-amino-4-(4-bromophenyl)-6-chloropyrimidine structure | MS (ESI pos.): m/z = 284 (M + H)+ | LC-MS (Method 10): R_t = 3.60 min |

-continued

| Ex. No. | Structure | MS | HPLC, LC-MS |
|---|---|---|---|
| LXVII | 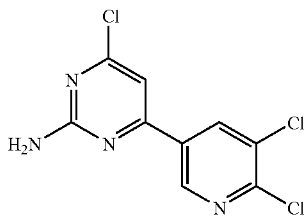 | MS (ESI pos.): m/z = 275 (M + H)⁺ | LC-MS (Method 18): $R_t$ = 3.48 min |
| LXVIII | 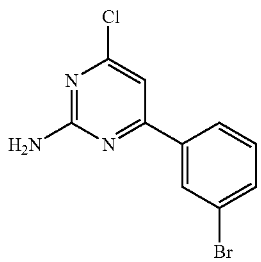 | MS (ESI pos.): m/z = 284 (M + H)⁺ | LC-MS (Method 9): $R_t$ = 4.21 min |

Example LXIX

Ethyl-(2-amino-6-chloropyrimidin-4-yl)acetate

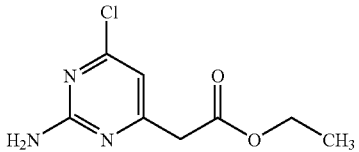

The title compound is synthesized analogously to example LVI in two steps from 3-diethyl 3-oxopentanedioate.

Yield: 394 mg (32%)

LC-MS (Method 10): $R_t$=2.62 min MS (ESI pos.): m/z=216 (M+H)⁺

¹H-NMR (DMSO-d₆, 300 MHz): δ=1.18 (t, 3H), 3.60 (s, 2H), 4.09 (q, 2H), 6.65 (s, 1H), 7.11 (s, 2H).

Example LXX 4-(2-Amino-6-chloropyrimidin-4-yl)butyric acid

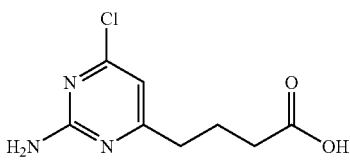

The title compound is synthesized analogously to example LVI in two steps from diethyl 3-oxoheptanedioate. During the second reaction step, the ester is hydrolyzed to give the carboxylic acid.

Yield: 394 mg (32%)

LC-MS (Method 12): $R_t$=2.46 min

MS (ESI pos.): m/z=216 (M+H)⁺

¹H-NMR (DMSO-d₆, 400 MHz): δ=1.83 (tt, 2H), 2.23 (t, 2H), 2.50 (t, 2H), 6.65 (s, 1H), 7.02 (s, 2H), 12.08 (br. s, 1H).

Example LXXI

Benzyl 3-(2-amino-6-hydroxypyrimidin-4-yl)piperidine-1-carboxylate

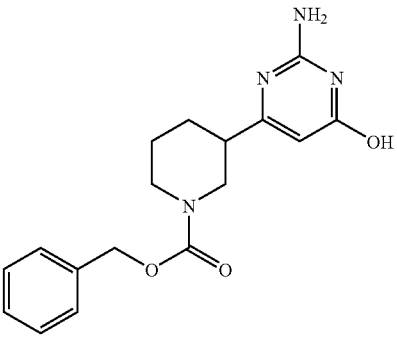

2 g (7.59 mmol) of 1-benzyl piperidine-1,3-dicarboxylate, 1.31 g (9.11 mmol) of 2,2-dimethyl-1,3-dioxolane-4,6-dione and 1.85 g (15.19 mmol) of 4-dimethylamino-pyridine are initially charged in 12 ml of dichloromethane, and the mixture is cooled to 0° C. 1.60 g (8.35 mmol) of (3-dimethylaminopropyl)ethylcarbodiimide hydrochloride are added. The mixture is stirred at 0° C. for one hour and then at room temperature for 18 hours. The reaction mixture is diluted with dichloromethane (50 ml) and washed successively with water (20 ml), 1N hydrochloric acid (30 ml), saturated aqueous sodium bicarbonate solution (30 ml) and saturated aqueous sodium chloride solution. The organic phase is dried over anhydrous magnesium sulfate. The solution is concentrated under reduced pressure. The residue (1.2 g) is dissolved in 30 ml of ethanol, 0.13 ml (0.61 mmol) of 37% strength hydrochloric acid is added and the mixture is stirred under reflux for one hour. After cooling, 0.59 g (3.18 mmol) of guanidinium carbonate is added and the reaction mixture is stirred at reflux (oil bath temperature 93° C.) for 18 hours. The solution is concentrated. The crude product is purified on a silica gel column using dichloromethane/methanol 20:1. This gives 0.68 g (27% of theory) of product.

HPLC (Method 7): $R_t$=3.77 min

MS (ESI pos): m/z=329 (M+H)$^+$ $^1$H-NMR (200 MHz, DMSO-d$_6$): δ=1.29 (m, 2H), 1.76 (dd, 2H), 2.29 (m, 1H), 2.79 (m, 2H), 4.03 (m, 2H), 5.07 (s, 2H), 5.42 (s, 1H), 6.49 (s, 2H), 7.35 (m, 5H), 10.65 (s, 1H).

Example LXXII

Benzyl 3-(2-amino-6-chloropyrimidin-4-yl)piperidine-1-carboxylate

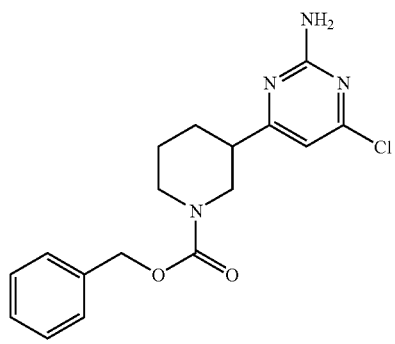

4.14 g (12.60 mmol) of benzyl 3-(2-amino-6-hydroxypyrimidin-4-yl)piperidine-1-carboxylate (from example LXXI) are suspended in 150 ml of acetonitrile. 3.29 ml (18.91 mmol) of N,N-diisopropylethylamine and 0.57 g (2.52 mmol) of benzyltriethylammonium chloride are added successively. The mixture is cooled to 0° C. At 0° C., 4.7 ml (50.43 mmol) of phosphoryl chloride are then slowly added dropwise. The mixture is stirred at room temperature for 18 hours. For work-up, the reaction solution is cooled to 0° C. and carefully added dropwise to ice water (150 ml). The aqueous suspension is neutralized using a 45% strength sodium hydroxide solution and extracted three times with ethyl acetate (in each case 70 ml). The organic phase is dried over anhydrous magnesium sulfate and concentrated. The residue is purified on a silica gel column using dichloromethane/methanol 30:1. This gives 2.80 g (64% of theory) of product.

HPLC (Method 7): $R_t$=4.30 min

MS (ESI pos): m/z=347 (M+H)$^+$ $^1$H-NMR (300 MHz, DMSO-d$_6$): δ=1.44 (m, 1H), 1.67 (m, 2H), 1.92 (m, 1H), 2.57 (m, 1H), 2.91 (m, 2H), 4.04 (dd, 2H), 5.09 (m, 2H), 6.61 (s, 1H), 7.02 (s, 2H), 7.35 (m, 5H).

Example LXXIII

Ethyl(2-amino-6-chloropyrimidin-4-yl)acetate

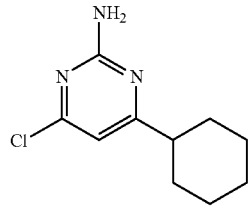

The title compound is synthesized analogously to example LXXI in two steps from cyclohexanecarboxylic acid.

Yield: 100 mg (44%)

LC-MS (Method 16): $R_t$=2.27 min

MS (ESI pos.): m/z=212 (M+H)$^+$ $^1$H-NMR (DMSO-d$_6$, 200 MHz): δ=1.35 (m, 5H), 1.75 (m, 5H), 2.40 (m, 1H), 6.54 (s, 1H), 6.97 (s, 2H).

Example LXXIV

Benzyl 3-(2-amino-6-{[3-fluoro-4-(1H-pyrrolo[2,3-b]pyridin-4-yloxy)phenyl]-amino}pyrimidin-4-yl)piperidine-1-carboxylate

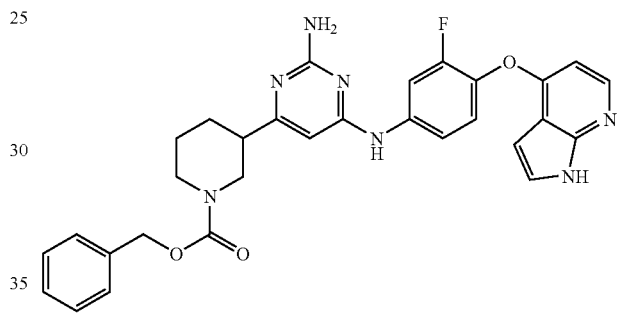

1.05 g (2.89 mmol) of benzyl 3-(2-amino-6-chloropyrimidin-4-yl)piperidine-1-carboxylate (from example LXXII) and 0.75 g (2.89 mmol) of [3-fluoro-4-(1H-pyrrolo[2,3-b]pyridin-4-yloxy)phenyl]amine (from example XIX) are suspended in 35 ml of water and 4 ml of ethanol. 0.29 ml (3.47 mmol) of 37% strength hydrochloric acid is added. The mixture is stirred at 100° C. for 18 hours. After cooling, the mixture is neutralized using a saturated aqueous sodium bicarbonate solution and extracted three times with ethyl acetate (in each case 30 ml). The organic phase is dried over anhydrous magnesium sulfate and concentrated. The residue is purified on a silica gel column using dichloromethane/methanol 20:1. This gives 1.38 g (86% of theory) of product.

HPLC (Method 7): $R_t$=4.23 min

MS (ESI pos): m/z=554 (M+H)$^+$ $^1$H-NMR (200 MHz, DMSO-d$_6$): δ=1.55 (m, 2H), 1.67 (m, 2H), 1.84 (m, 2H), 2.54 (m, 1H), 2.85 (m, 2H), 4.10 (dd, 2H), 5.09 (s, 2H), 5.92 (s, 1H), 6.25 (dd, 1H), 6.35 (m, 3H), 7.27 (t, 1H), 7.36 (m, 7H), 8.06 (d, 1H), 8.21 (dd, 1H), 9.42 (s, 1H), 11.08 (s, 1H).

The following compounds are prepared analogously to example LXXIV:

| Ex. No. | Structure | MS | HPLC, LC-MS |
|---|---|---|---|
| LXXV | 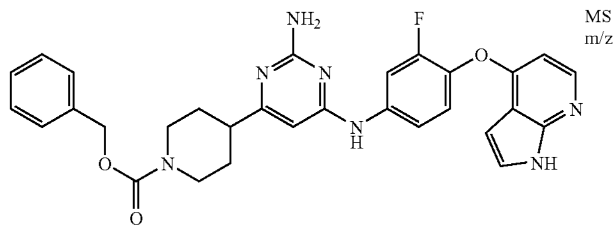 | MS (ESI pos.): m/z = 554 (M + H)⁺ | HPLC (Method 11): $R_t$ = 4.14 min |
| LXXVI | 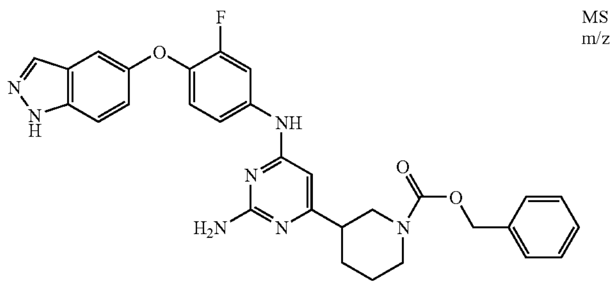 | MS (ESI pos.): m/z = 554 (M + H)⁺ | LC-MS (Method 15): $R_t$ = 1.49 min |
| LXXVII | 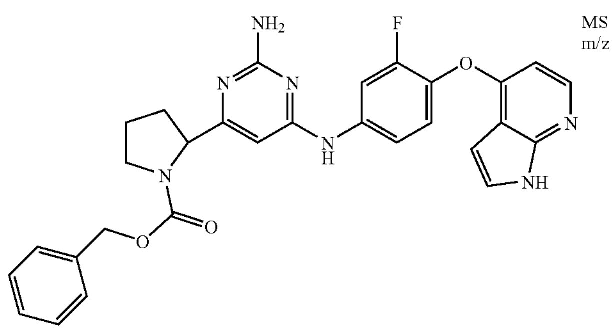 | MS (ESI pos.): m/z = 209 (M + H)⁺ | LC-MS (Method 16): $R_t$ = 2.02 min |

Example LXXVIII (2-Amino-6-chloropyrimidin-4-yl)methanol

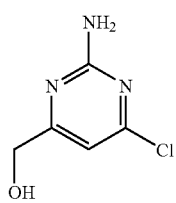

10.5 g (55.97 mmol) of methyl 2-amino-6-chloropyrimidine-4-carboxylate (prepared according to G. Doyle Daves, Fred Baiocchi, Roland K. Robins, and C. C. Cheng, *J. Org. Chem.*, 26 (1961), 2755-2763) are initially charged in 450 ml of ethanol. 21.17 g (559.74 mmol) of sodium borohydride are added, and the mixture is stirred at room temperature for 2 hours. 500 ml of ethyl acetate and 500 ml of water are added, and the solution is stirred for 30 minutes. The phases are separated and the aqueous phase is extracted three times with ethyl acetate (in each case 100 ml). The combined organic phases are washed with saturated aqueous sodium chloride solution, dried with anhydrous magnesium sulfate and concentrated. This gives 7.21 g (85% of theory) of product.

LC-MS (Method 13): $R_t$=0.58 min

MS (ESI pos): m/z=160 (M+H)⁺

¹H-NMR (200 MHz, DMSO-d₆): δ=4.31 (d, 2H), 5.49 (t, 1H), 6.66 (s, 1H), 7.05 (s, 2H).

Beispiel LXXIX 4-(Bromomethyl)-6-chloropyrimidine-2-amine and 4-(bromomethyl)-6-bromopyrimidine-2-amine

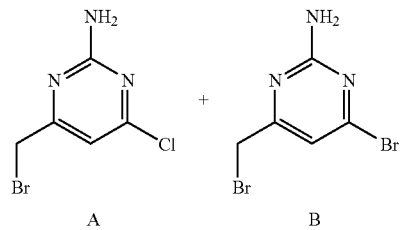

A     B 0.55 g (3.49 mmol) of (2-amino-6-chloropyrimidin-4-yl)methanol (from example LXXVIII) is initially charged in 11 ml of THF. 0.73 ml (7.67 mmol) of phosphorus tribromide are added, and the mixture is stirred at room temperature for 3 hours. 20 ml of ethyl acetate and 20 ml of ice water are added, and the solution is stirred for 30 minutes. The phases are separated and the aqueous phase is extracted three times with ethyl acetate (in each case 10 ml). The combined organic phases are washed with saturated aqueous sodium bicarbonate solution and sodium chloride solution, dried with anhydrous magnesium sulfate and concentrated. This gives 0.55 g (62% of theory) of a mixture of A and B (8:1).

LC-MS (Method 14): $R_t$=1.74 min and 1.83 min
MS (ESI pos): m/z=224 and 268 (M+H)$^+$
$^1$H-NMR (200 MHz, DMSO-d$_6$): δ=4.34 (d, 0.7H), 4.37 (d, 1.3H), 6.81 (s, 0.7H), 6.94 (s, 0.3H), 7.28 (s, 2H).

Example LXXX

4-[(tert-Butylamino)methyl]-6-chloropyrimidine-2-amine and 4-[(tert-butylamino)-methyl]-6-bromopyrimidine-2-amine

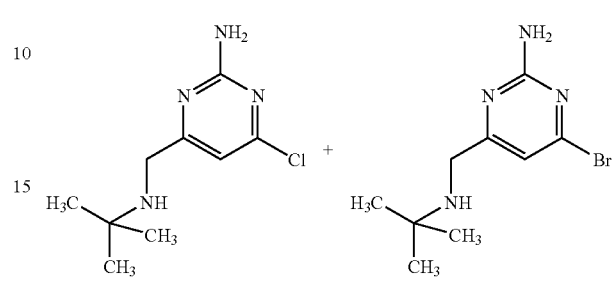

0.1 g (0.45 mmol) of the mixture of 4-(bromomethyl)-6-chloropyrimidine-2-amine and 4-(bromomethyl)-6-bromopyrimidine-2-amine (from example LXXIX) is initially charged in 1 ml of dimethylformamide. 0.07 ml (0.67 mmol) of tert-butylamine is added, and the mixture is stirred at room temperature for 2 hours. The solution is purified by RP-HPLC chromatography (gradient: acetonitrile/water). This gives 0.063 g (65%) of product.

LC-MS (Method 14): $R_t$=0.46 min
MS (ESI pos): m/z=215 and 259 (M+H)$^+$

The following compounds are prepared analogously to example LXXX:

| Ex. No. | Structure | MS | HPLC, LC-MS |
|---|---|---|---|
| LXXXI | (piperidine-CH$_2$-pyrimidine-NH$_2$-Cl) | MS (ESI pos.): m/z = 227 (M[Cl] + H)$^+$, 271 (M[Br] + H)$^+$ | LC-MS (Method 14): $R_t$ = 0.35 (Cl), 0.41 (Br) min |
| LXXXII | (2-methylpiperidine-CH$_2$-pyrimidine-NH$_2$-Cl) | MS (ESI pos.): m/z = 241 (M[Cl] + H)$^+$, 285 (M[Br] + H)$^+$ | LC-MS (Method 15): $R_t$ = 0.47 min |
| LXXXIII | (2,6-dimethylpiperidine-CH$_2$-pyrimidine-NH$_2$-Cl) | MS (ESI pos.): m/z = 255 (M[Cl] + H)$^+$, 299 (M[Br] + H)$^+$ | LC-MS (Method 15): $R_t$ = 0.60, 0.68 min |

-continued

| Ex. No. | Structure | MS | HPLC, LC-MS |
|---|---|---|---|
| LXXXIV | ![structure] | MS (ESI pos.): m/z = 243 (M[Cl] + H)+ | LC-MS (Method 15): $R_t$ = 0.55 min |
| LXXXV | ![structure] | MS (ESI pos.): m/z = 241 (M[Cl] + H)+, 285 (M[Br] + H)+ | LC-MS (Method 15): $R_t$ = 0.59 min |
| LXXXVI | ![structure] | MS (ESI pos.): m/z = 253 (M[Cl] + H)+, 297 (M[Br] + H)+ | LC-MS (Method 13): $R_t$ = 2.10 (Cl), 2.15 (Br) min |
| LXXXVII | ![structure] | MS (ESI pos.): m/z = 201 (M[Cl] + H)+, 245 (M[Br] + H)+ | LC-MS (Method 13): $R_t$ = 0.27 min |
| LXXXVIII | ![structure] | MS (ESI pos.): m/z = 199 (M[Cl] + H)+, 243 (M[Br] + H)+ | LC-MS (Method 14): $R_t$ = 0.44 min |
| LXXXIX | ![structure] | MS (ESI pos.): m/z = 281 (M[Cl] + H)+, 315 (M[Br] + H)+ | LC-MS (Method 15): $R_t$ = 1.12 (Cl), 1.21 (Br) min |
| XC | ![structure] | MS (ESI pos.): m/z = 201 (M[Cl] + H)+, 245 (M[Br] + H)+ | LC-MS (Method 15): $R_t$ = 0.51 min |

The following compound is prepared analogously to example LXXIV:

| Ex. No. | Structure | MS | HPLC, LC-MS |
|---|---|---|---|
| XCI | (structure shown) | MS (ESI pos.): m/z = 554 (M + H)$^+$ | LC-MS (Method 9): $R_t$ = 2.31 min |

Preparation Examples

Example 1

N-[2-Amino-6-(4-pyridinyl)-4-pyrimidinyl]-N-{3-fluoro-4-[(3-methyl-1H-indazol-4-yl)oxy]phenyl}amine

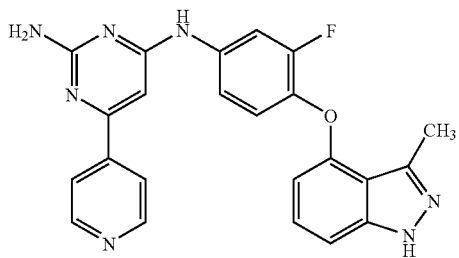

60 mg (0.23 mmol) of 3-fluoro-4-[(3-methyl-1H-indazol-4-yl)oxy]phenylamine (from example III) and 48 mg (0.23 mmol) of 4-chloro-6-(4-pyridinyl)-2-pyrimidineamine (from example XXIX) are suspended in 4 ml of water, and 0.02 ml of concentrated hydrochloric acid is added. The reaction mixture is heated at reflux overnight, resulting in the formation of a brown precipitate. This is filtered off, washed repeatedly with water and dried under high vacuum. This gives 65 mg (65% of theory) of the product as a brown solid.

LC-MS (Method 2): $R_t$=2.9 min

MS (ESI pos.): m/z=428 (M+H)$^+$ $^1$H-NMR (DMSO-d$_6$, 300 MHz): δ=2.56 (s, 3H), 6.27 (d, 1H), 6.79 (s, 1H), 7.18 (m, 3H), 7.47 (d, 1H), 7.89 (d, 2H), 8.22 (d, 1H), 8.86 (d, 2H), 10.88 (s, 1H), 12.75 (s, 1H).

Example 2

N-{4-[(3-Amino-1,2-benzisoxazol-4-yl)oxy]-3-fluorophenyl}-N-[2-amino-6-(4-pyridinyl)-4-pyrimidinyl]amine

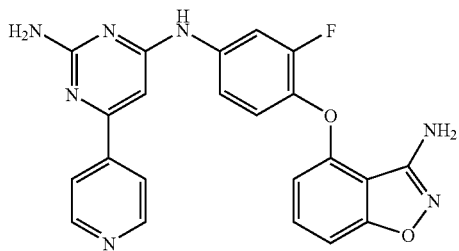

70 mg (0.27 mmol) of 4-(4-amino-2-fluorophenoxy)-1,2-benzisoxazole-3-amine (from example VII) and 55.8 mg (0.27 mmol) of 4-chloro-6-(4-pyridinyl)-2-pyrimidineamine (from example XXIX) are suspended in 4 ml of water, and 0.02 ml of concentrated hydrochloric acid is added. The reaction mixture is heated at reflux overnight, resulting in the formation of a lightly colored precipitate. This is filtered off, washed repeatedly with water and dried under high vacuum.

Yield: 60 mg (52% of theory)

LC-MS (Method 6): $R_t$=2.7 min

MS (ESI pos.): m/z=429 (M+H)$^+$ $^1$H-NMR (DMSO-d$_6$, 300 MHz): δ=5.28 (m, 4H), 6.33 (d, 1H), 6.97 (s, 1H), 7.14 (d, 1H), 7.43 (m, 2H), 7.58 (d, 1H), 8.02 (d, 2H), 8.28 (d, 1H), 8.93 (d, 2H), 11.43 (s, 1H).

Example 3

N-{4-[(3-Amino-1,2-benzisoxazol-4-yl)oxy]-3-fluorophenyl}-N-(2-amino-6-chloro-4-pyrimidinyl)amine

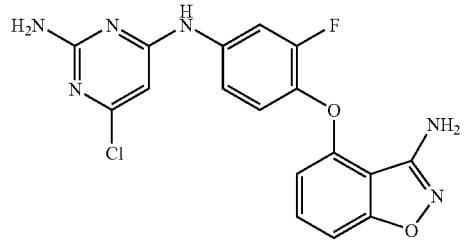

100 mg (0.39 mmol) of 4-(4-amino-2-fluorophenoxy)-1,2-benzisoxazole-3-amine (from example VII) and 63.3 mg (0.39 mmol) of 2-amino-4,6-dichloropyrimidine are suspended in 3 ml of water, and 0.04 ml of concentrated hydrochloric acid is added. The reaction mixture is heated at reflux overnight, resulting in the formation of a colorless precipitate. This is filtered off, washed repeatedly with water and dried under high vacuum.

Yield: 100 mg (67% of theory)

LC-MS (Method 8): $R_t$=3.38 min

MS (ESI pos.): m/z=387 (M+H)$^+$

Example 4

4-[(4aR,7aR)-Octahydro-6H-pyrrolo[3,4-b]pyridin-6-yl]-6-({4-[(3-amino-1,2-benz-isoxazol-4-yl)oxy]-3-fluorophenyl}amino)-2-pyrimidinylamine

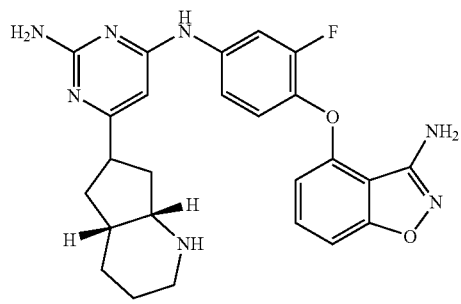

88 mg (0.23 mmol) of N-{4-[(3-amino-1,2-benzisoxazol-4-yl)oxy]-3-fluorophenyl}-N-(2-amino-6-chloro-4-pyrimidinyl)amine (from example 3) and 114.8 mg (0.91 mmol) of [(4aR,7aR)-octahydro-6H-pyrrolo[3,4-b]pyridine together with 294.1 mg (2.28 mmol) of diisopropylethylamine are dissolved in 4 ml of 2-ethylhexanol, and the mixture is stirred at 150° C. for 3 h. After cooling, the reaction mixture is filtered and water is added. The mixture is extracted repeatedly with ethyl acetate, the organic phase is dried over magnesium sulfate and the solvent is removed under reduced pressure. The residue is purified by preparative HPLC.

Yield: 15 mg (14% of theory)

LC-MS (Method 8): $R_t$=2.2 min

MS (ESI pos.): m/z=477 (M+H)$^+$

Example 5

N-[2-Amino-6-(4-pyridinyl)-4-pyrimidinyl]-N-[3-fluoro-4-(1H-indazol-5-yloxy)-phenyl]amine

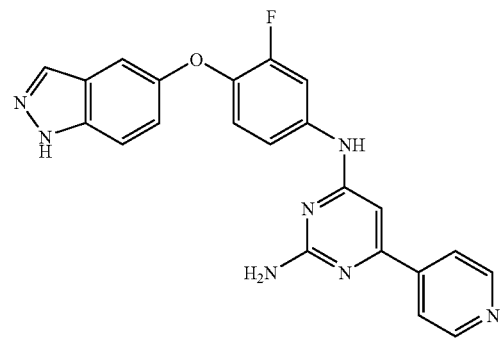

600 mg (2.47 mmol) of 5-(4-amino-2-fluorophenoxy)-1H-indazole (from example XII) are suspended in 100 ml of water. 510 mg (2.47 mmol) of 4-chloro-6-(4-pyridinyl)-2-pyrimidineamine (from example XXIX) and 0.25 ml of concentrated aqueous hydrogen chloride solution are added, and the mixture is stirred at 100° C. overnight. For work-up, the reaction solution was made alkaline with saturated sodium bicarbonate solution and extracted 3× with ethyl acetate. The precipitate obtained contains crude product and is filtered off with suction. The organic phase is dried with sodium sulfate and concentrated using a rotary evaporator. The residue is combined with the precipitate and purified by preparative HPLC.

Yield: 631 mg (62% of theory)

MS (ESI pos.): m/z=414 (M+H)$^+$ $^1$H-NMR (DMSO-d$_6$, 200 MHz): δ=6.56 (s, 1H), 6.63 (s, 2H), 7.06-7.19 (m, 3H), 7.33 (d, 1H), 7.53 (d, 1H), 7.84 (dd, 2H), 7.97 (s, 1H), 8.22 (dd, 1H), 8.72 (dd, 2H), 9.60 (s, 1H), 13.03-13.12 (br. s, 1H).

The following compounds are prepared analogously to example 5:

| Ex. No. | Structure | MS, HPLC, LC-MS | NMR |
|---|---|---|---|
| 6 | 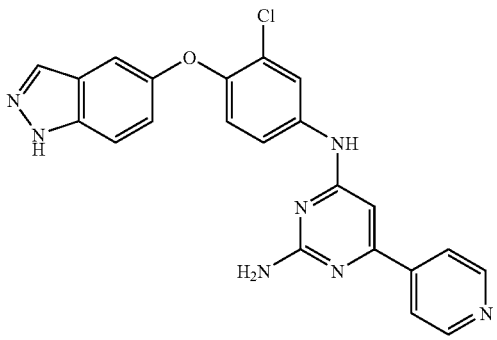 | MS (ESI pos.): m/z = 430 (M + H)$^+$ | $^1$H-NMR (DMSO-d$_6$, 200 MHz): δ = 6.58 (m, 3 H), 7.04 (d, 1 H), 7.11–7.19 (m, 2 H), 7.52–7.68 (m, 2 H), 7.85 (d, 2 H), 7.99 (s, 1 H), 8.16 (d, 1 H), 8.71 (d, 2 H), 9.52 (s, 1 H), 13.03–13.13 (br. s, 1 H). |

| Ex. No. | Structure | MS, HPLC, LC-MS | NMR |
|---|---|---|---|
| 7 | 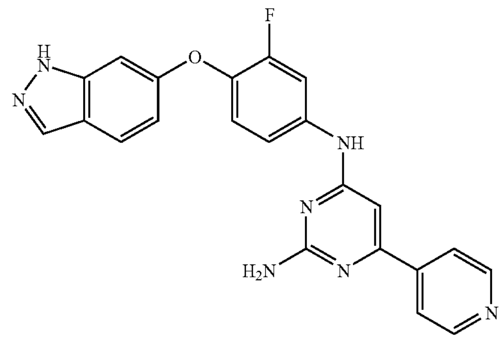 | MS (ESI pos.): m/z = 413 (M + H)+, LC-MS (Method Method 8): R$_t$ = 2.72 min | $^1$H-NMR (DMSO-d$_6$, 300 MHz): δ = 6.58 (s, 2 H), 6.80 (s, 1 H), 6.92 (dd, 1 H), 7.22 (t, 1 H), 7.39 (dd, 1 H), 7.73 (d, 1 H), 7.85 (d, 2 H), 8.01 (s, 1 H), 8.24 (dd, 1 H), 8.72 (d, 2 H), 9.62 (s, 1 H), 12.77 (s, 1 H). |

Example 8

N-[2-Amino-6-chloro-4-pyrimidinyl]-N-[3-fluoro-4-(1H-indazol-5-yloxy)phenyl]amine

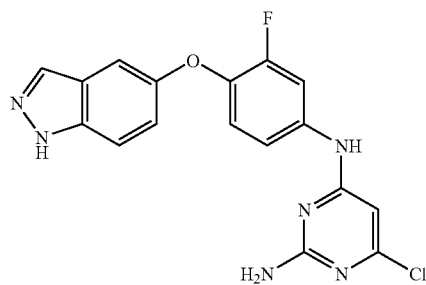

1.65 g (6.78 mmol) of 5-(4-amino-2-fluorophenoxy)-1H-indazole (from example XII) are suspended in 90 ml of water. 1.11 g (6.78 mmol) of 4,6-dichloro-2-pyrimidineamine and 0.68 ml of concentrated aqueous hydrogen chloride solution are added, and the mixture is stirred at 100° C. overnight. For work-up, the reaction solution is made alkaline with saturated sodium bicarbonate solution and extracted 3× with ethyl acetate. The organic phase is dried with sodium sulfate and concentrated using a rotary evaporator.

Yield: 2.88 g (quantitative)

LC-MS (Method 8): R$_t$=3.21 min

MS (ESI pos.): m/z=371 (M+H)$^+$

The following compounds are prepared analogously to example 8:

| Ex. No. | Structure | MS, HPLC, LC-MS | NMR |
|---|---|---|---|
| 9 | 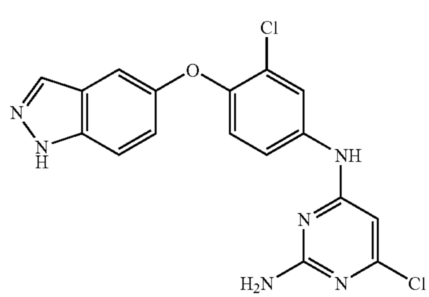 | MS (ESI pos.): m/z = 387 (M + H)+ HPLC (Method 7): R$_t$ = 3.93 min | $^1$H-NMR (DMSO-d$_6$, 300 MHz): δ = 5.98 (s, 1 H), 6.75 (s, 2 H), 6.99 (d, 1 H), 7.08–7.18 (m, 2 H), 7.49–7.57 (m, 2 H), 7.94–8.02 (m, 2 H), 9.42 (s, 1 H), 13.05 (s, 1 H). |

| Ex. No. | Structure | MS, HPLC, LC-MS | NMR |
|---|---|---|---|
| 10 | 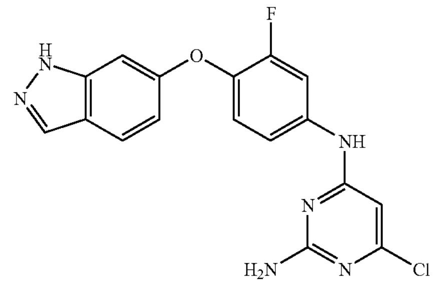 | MS (ESI pos.): m/z = 371 (M + H)+ LC-MS (Method 9): $R_t$ = 4.02 min | $^1$H-NMR (DMSO-$d_6$, 300 MHz): δ = 6.58 (s, 2 H), 6.80 (s, 1 H), 6.92 (dd, 1 H), 7.22 (t, 1 H), 7.39 (dd, 1 H), 7.73 (d, 1 H), 7.85 (d, 2 H), 8.01 (s, 1 H), 8.24 (dd, 1 H), 8.72 (d, 2 H), 9.62 (s, 1 H), 12.77 (s, 1 H). |

Example 11

6-[(4aR,7aR)-Octahydro-6H-pyrrolo[3,4-b]pyridin-6-yl]-N-4-[3-fluoro-4-(1H-indazol-5-yloxy)phenyl]-2,4-pyrimidinediamine

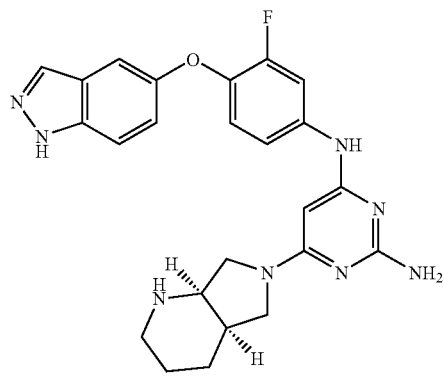

127 mg (340 μmol) of N-[2-amino-6-chloro-4-pyrimidinyl]-N-[3-fluoro-4-(1H-indazol-5-yloxy)phenyl]amine (from example 8) are suspended in 10 ml of 2-ethylhexanol. 173 mg (1.37 mmol) of [(4aR,7aR)-octahydro-6H-pyrrolo[3,4-b]-pyridine and 0.60 ml (3.43 mmol) of diisopropylethylamine are then added, and the mixture is stirred at 150° C. overnight. The reaction solution is chromatographed by MPLC using dichloromethane/methanol/concentrated aqueous ammonia solution 20:1:0→10:1:0→5:1:0→3:1:0.1.

Yield: 147 mg (93%)

LC-MS (Method 5): $R_t$=3.12 min

MS (ESI pos.): m/z=461 (M+H)+

$^1$H-NMR (DMSO-$d_6$, 200 MHz): δ=1.17-1.30 (m, 1H), 1.60-1.85 (m, 4H), 2.54-2.70 (m, 1H), 2.80-2.97 (m, 1H), 3.05-3.63 (several m, partially obscured by the H$_2$O peak, 4H in total), 3.65-3.80 (m, 1H), 5.12 (s, 1H), 5.98 (s, 2H), 6.92-7.26 (m, 4H), 7.52 (d, 1H), 7.93 (s, 1H), 8.11 (dd, 1H), 8.94 (s, 1H), 13.05 (s, 1H).

The following compounds are prepared analogously to example 11:

| Ex. No. | Structure | MS, HPLC, LC-MS, TLC | NMR |
|---|---|---|---|
| 12 | 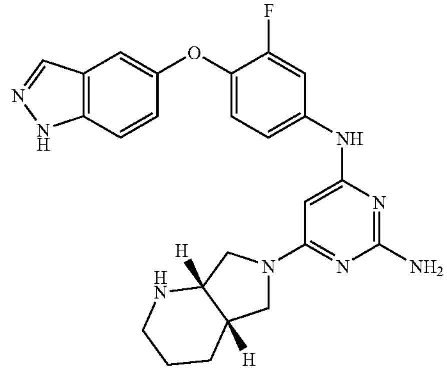 | MS (ESI pos.): m/z = 461 (M + H)+ LC-MS (Method 8): $R_t$ = 2.12 min | |

| Ex. No. | Structure | MS, HPLC, LC-MS, TLC | NMR |
|---|---|---|---|
| 13 | 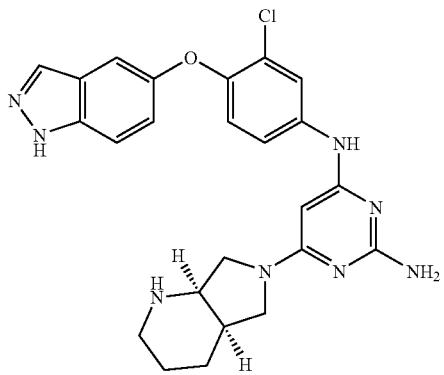 | MS (ESI pos.): m/z = 477 (M + H)⁺ LC-MS (Method 8): R$_t$ = 2.23 min TLC (silica gel): R$_f$ = 0.09 (dichloromethane/methanol 10:1) | |
| 14 | 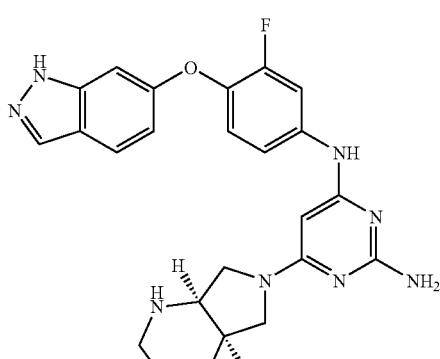 | MS (ESI pos.): m/z = 461 (M + H)⁺ LC-MS (Method 2): R$_t$ = 2.40 min | |
| 15 | 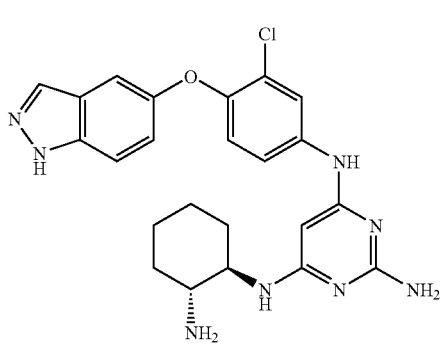 | MS (ESI pos.): m/z = 465 (M + H)⁺ MS (ESI neg.): m/z = 463 (M − H)⁻ LC-MS (Method 8): R$_t$ = 2.09 min | ¹H-NMR (DMSO-d$_6$, 400 MHz): δ = 1.12–1.34 (m, 6 H), 1.63–1.74 (m, 2 H), 1.85–2.01 (m, 2 H), 2.69–2.78 (m, 1 H), 3.50–3.63 (br. s, 1 H), 5.20 (s, 1 H), 5.80 (s, 2 H), 6.20–6.43 (m, 3 H), 6.94 (d, 1 H), 7.05–7.13 (m, 2 H), 7.48 (dd, 1 H), 7.53 (d, 1 H), 7.92–7.99 (m, 2 H), 8.74 (s, 1 H), 13.01–13.12 (br. s, 1 H). |

-continued

| Ex. No. | Structure | MS, HPLC, LC-MS, TLC | NMR |
|---|---|---|---|
| 16 | 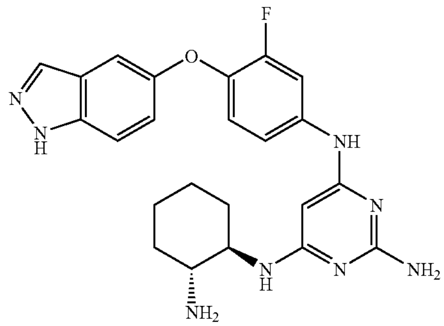 | MS (ESI pos.): m/z = 449 (M + H)+ HPLC (Method 7): R$_t$ = 3.78 min TLC (silica gel): R$_f$ = 0.22 (dichloromethane/ methanol 3:1) | |
| 17 | 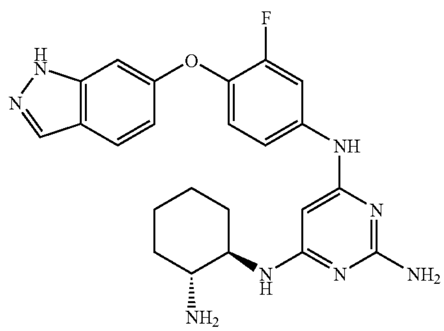 | MS (ESI pos.): m/z = 449 (M + H)+ HPLC (Method 7): R$_t$ = 3.82 min | |

Example 18

N-(2-Amino-6-phenyl-4-pyrimidinyl)-N-[3-fluoro-4-(1H-indazol-5-yloxy)phenyl]amine

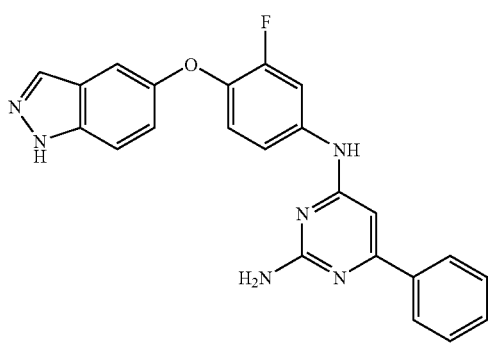

50 mg (130 μmol) of N-[2-amino-6-chloro-4-pyrimidinyl]-N-[3-fluoro-4-(1H-indazol-5-yloxy)phenyl]amine (from example 8) are suspended in 3 ml of toluene/ethanol (2:1), and 4.68 mg of tetrakis(triphenylphosphine)palladium (0) are added. After addition of 19.7 mg (160 μmol) of phenylboronic acid and 0.50 ml of 2M aqueous sodium carbonate solution, the mixture is stirred at 100° C. overnight. The mixture is evaporated to dryness using a rotary evaporator and purified by preparative HPLC.

Yield: 10 mg (17% of theory)

LC-MS (Method 9): R$_t$=3.55 min

MS (ESI pos.): m/z=413 (M+H)+

Example 19

N-[2-Amino-6-(4-pyridinyl)-4-pyrimidinyl]-N-[3-fluoro-4-(1H-pyrrolo[2,3-b]pyridin-4-yloxy)phenyl] amine

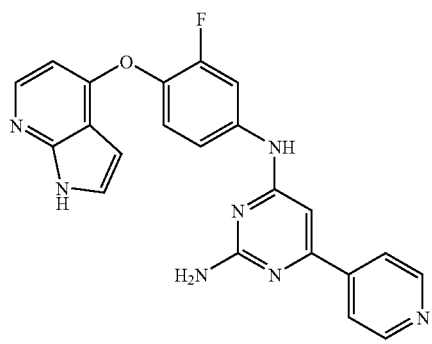

55.6 mg (230 µmol) of 3-fluoro-4-(1H-pyrrolo[2,3-b]pyridin-4-yloxy)aniline (from example XIX) are suspended in 5 ml of water. 47.2 mg (230 µmol) of 4-chloro-6-(4-pyridinyl)-2-pyrimidineamine (from example XXIX) and 0.01 ml of concentrated hydrochloric acid are added, and the mixture is stirred at 100° C. overnight. For work-up, the reaction solution is made alkaline using saturated sodium bicarbonate solution and extracted 3× with ethyl acetate, and the extracts are dried over sodium sulfate and concentrated using a rotary evaporator. The residue is purified by preparative HPLC.

Yield: 6.5 mg (6.0% of theory)

LC-MS (Method 6): $R_t$=2.52 min

MS (ESI pos.): m/z=207 (M+H)$^{2+}$

MS (ESI neg.): m/z=412 (M−H)$^−$

Example 20

N-[2-Amino-6-(4-pyridinyl)-4-pyrimidinyl]-N-[2-fluoro-4-(1H-pyrrolo[2,3-b]-pyridin-4-yloxy)phenyl]amine

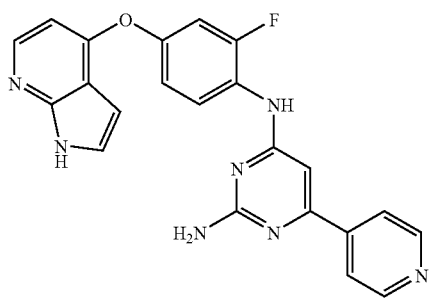

11 mg (50 µmol) of 2-fluoro-4-(1H-pyrrolo[2,3-b]pyridin-4-yloxy)aniline (from example XX) are suspended in 5 ml of water. 9.3 mg (50 µmol) of 4-chloro-6-(4-pyridinyl)-2-pyrimidineamine (from example XXIX) and 0.01 ml of concentrated hydrochloric acid are added, and the mixture is stirred at 100° C. overnight. For work-up, the reaction solution is made alkaline with saturated sodium bicarbonate solution and extracted 3× with ethyl acetate, and the extracts are dried over sodium sulfate and concentrated using a rotary evaporator.

Yield: 20 mg (98% of theory)

LC-MS (Method 6): $R_t$=2.47 min

MS (ESI pos.): m/z=414 (M+H)$^+$, 207 (M+H)$^{2+}$

MS (ESI neg.): m/z=412 (M−H)$^−$ $^1$H-NMR (DMSO-$d_6$, 400 MHz): δ=6.25 (d, 1H), 6.45 (s, 1H), 6.52 (d, 1H), 6.76 (s, 2H), 7.00 (d, 1H), 7.23 (dd, 1H), 7.38 (s, 1H), 7.80-7.89 (m, 2H), 8.14 (d, 1H), 8.25 (t, 1H), 8.62-8.77 (m, 2H), 9.06 (s, 1H), 11.88-12.08 (br. s, 1H).

Example 21

N-[2-Amino-6-(4-pyridinyl)-4-pyrimidinyl]-N-[4-(1-benzofuran-4-yloxy)-3-fluoro-phenyl]amine

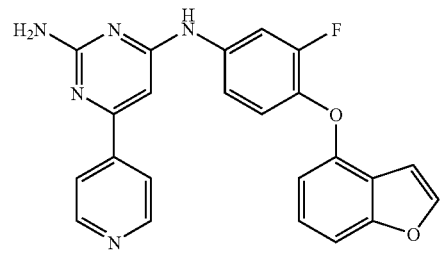

32 mg (0.13 mmol) of 4-(1-benzofuran-4-yloxy)-3-fluorophenylamine (from example XXIII) and 28.5 mg (0.14 mmol) of 4-chloro-6-(4-pyridinyl)-2-pyrimidine-amine (from example XXIX) are suspended in 1.5 ml of water, and 19 µl of concentrated hydrochloric acid are added. The reaction mixture is heated at reflux overnight, resulting in the formation of a brown precipitate. Using 1N sodium hydroxide solution, the suspension is adjusted to pH 10. The precipitate is filtered off with suction and the filtrate is discarded. The crude product is purified by preparative HPLC.

Yield: 43 mg (79% of theory)

LC-MS (Method 2): $R_t$=3.2 min

MS (ESI pos.): m/z=414 (M+H)$^+$ $^1$H-NMR (DMSO-$d_6$, 200 MHz): δ=6.67 (s, 2H), 6.88 (s, 1H), 7.32 (m, 4H), 7.86 (m, 2H), 8.00 (d, 1H), 8.28 (dd, 1H), 8.84 (d, 2H), 10.46 (s, 1H).

Example 22

N-[2-Amino-6-(4-pyridinyl)-4-pyrimidinyl]-N-[3-fluoro-4-(1H-indazol-4-yloxy)phenyl]amine

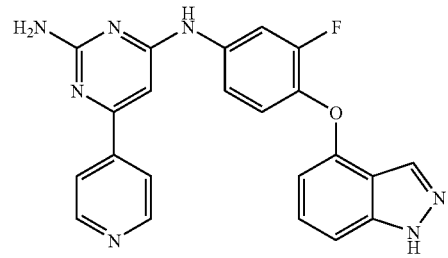

45 mg (0.19 mmol) of 3-fluoro-4-(1H-indazol-4-yloxy)aniline (from example XXVI) and 40.1 mg (0.19 mmol) of 4-chloro-6-(4-pyridinyl)-2-pyrimidineamine (from example XXIX) are suspended in 2 ml of water, and 27 µl of concentrated hydrochloric acid are added. The reaction mixture is heated at reflux overnight, resulting in the formation of a brown precipitate. Using 1N sodium hydroxide solution, the suspension is adjusted to pH 10. The precipitate is filtered off from the aqueous phase, and the filtrate is discarded. The crude product is purified by HPLC.

Yield: 20 mg (26% of theory)

LC-MS (Method 2): $R_t$=2.9 min

MS (ESI pos.): m/z=414 (M+H)$^+$

1H-NMR (DMSO-d$_6$, 200 MHz): δ=6.34 (dd, 1H), 6.64 (s, 2H), 6.60 (s 1H), 7.28 (m, 4H), 7.85 (d, 2H), 7.96 (s, 1H), 8.26 (dd, 1H), 8.70 (d, 2H), 9.67 (s, 1H), 13.2 (s, 1H).

Example 23

N$^4$-{3-Fluoro-4-[(3-methyl-1H-pyrrolo[2,3-b]pyridin-4-yl)oxy]phenyl}-6-pyridin-4-ylpyrimidine-2,4-diamine

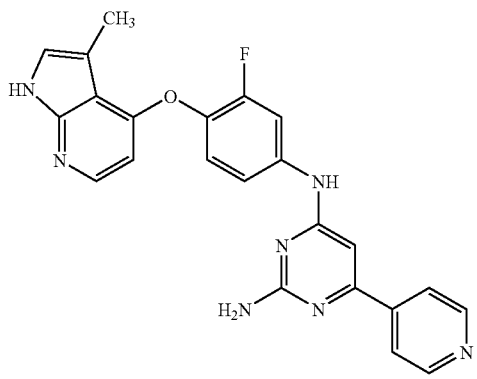

10 mg (0.04 mmol) of {3-fluoro-4-[(3-methyl-1H-pyrrolo[2,3-b]pyridin-4-yl)oxy]-phenyl}amine (from example XLII) and 8.40 mg (0.04 mmol) of 4-chloro-6-(4-pyridinyl)-2-pyrimidineamine (from example XXIX) are suspended in 1.5 ml of water. 5.6 µl of concentrated hydrochloric acid are added, and the mixture is stirred at 100° C. overnight. For work-up, the reaction solution is made alkaline using saturated sodium carbonate solution and extracted three times with ethyl acetate, and the extracts are dried over sodium sulfate and concentrated using a rotary evaporator. The residue is purified by preparative HPLC.

Yield: 3.30 mg (20% of theory)

LC-MS (Method 9): R$_t$=1.97 min

Example 24

N$^4$-{3-Fluoro-4-[(3-methyl-1H-pyrrolo[2,3-b]pyridin-4-yl)oxy]phenyl}-6-(4-fluorophenyl)pyrimidine-2,4-diamine

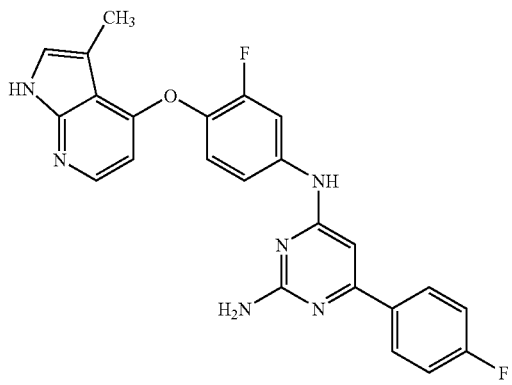

180 mg (0.70 mmol) of {3-fluoro-4-[(3-methyl-1H-pyrrolo[2,3-b]pyridin-4-yl)oxy]-phenyl}amine (from example XLII) and 191 mg (0.73 mmol) of 4-chloro-6-(4-fluorophenyl)pyrimidine-2-amine (from example LIX) are suspended in 10 ml of water. 101 µl of concentrated hydrochloric acid are added, and the mixture is stirred at 100° C. overnight. For work-up, the reaction solution is made alkaline using saturated sodium carbonate solution and extracted three times with ethyl acetate, and the extracts are dried over sodium sulfate and concentrated using a rotary evaporator. The residue is purified by preparative HPLC.

Yield: 70 mg (23% of theory)

LC-MS (Method 17): R$_t$=1.73 min

MS (ESI pos.): m/z=445 (M+H)$^+$

Example 25

6-(4-Fluorophenyl)-N$^4$-[3-fluoro-4-(1H-pyrrolo[2,3-b]pyridin-4-yloxy)phenyl]-pyrimidine-2,4-diamine

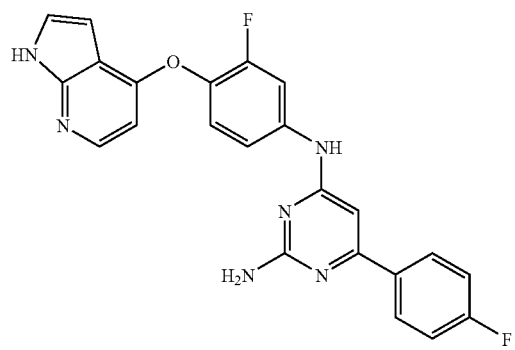

36 mg (0.15 mmol) of 3-fluoro-4-(1H-pyrrolo[2,3-b]pyridin-4-yloxy)aniline (from example XIX) and 38.5 mg (0.15 mmol) of 4-chloro-6-(4-fluorophenyl)pyrimidine-2-amine (from example LIX) are suspended in 1.5 ml of water, and 0.1 ml of 2 molar hydrochloric acid is added. The mixture is heated under reflux overnight. Ethyl acetate and a few drops of dimethylformamide are then added. The mixture is made alkaline using saturated sodium carbonate solution, the organic phase is separated off and the solvent is removed under reduced pressure. The product is purified by preparative HPLC.

Yield: 28 mg (40% of theory)

LC-MS (Method 10): R$_t$=2.22 min

MS (ESI pos.): m/z=431 (M+H)$^+$

1H-NMR (DMSO-d$_6$, 400 MHz): δ=6.27 (d, 1H), 6.37 (d, 1H), 6.50 (s, 1H), 6.52 (s, 2H), 7.27-7.43 (m, 5H), 8.00 (dd, 2H), 8.07 (d, 1H), 8.28 (dd, 1H), 9.58 (s, 1H), 11.75 (s, 1H).

Example 26

N$^4$-[3,5-Difluoro-4-(1H-pyrrolo[2,3-b]pyridin-4-yloxy)phenyl]-6-(4-fluorophenyl)-pyrimidine-2,4-diamine

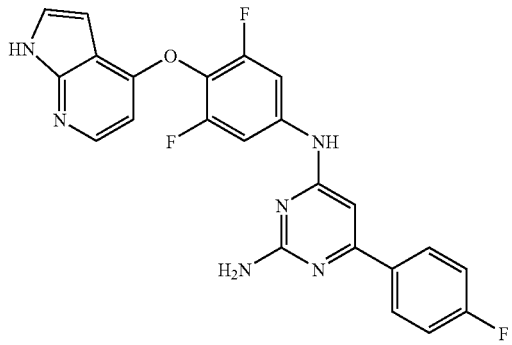

Analogously to example 25, the title compound is synthesized from 100 mg (0.36 mmol) of [3,5-difluoro-4-(1H-pyrrolo[2,3-b]pyridin-4-yloxy)phenyl]amine (from example XXXIV) and 110 mg (0.36 mmol) of 4-chloro-6-(4-fluorophenyl)pyrimidine-2-amine (from example LIX). Purification by preparative HPLC gives the product.

Yield: 17 mg (10% of theory)
LC-MS (Method 10): R$_t$=2.32 min
MS (ESI pos.): m/z=449 (M+H)$^+$
$^1$H-NMR (DMSO-d$_6$, 400 MHz): δ=6.31 (dd, 1H), 6.43 (d, 1H), 6.48 (s, 1H), 6.63 (br. s, 2H), 7.33 (t, 2H), 7.41 (dd, 1H), 7.83 (d, 2H), 8.01 (dd, 2H), 8.09 (d, 1H), 9.72 (s, 1H), 11.82 (s, 1H).

Example 27

N$^4$-[3,5-Difluoro-4-(1H-pyrrolo[2,3-b]pyridin-4-yloxy)phenyl]-6-pyridin-4-yl-pyrimidine-2,4-diamine

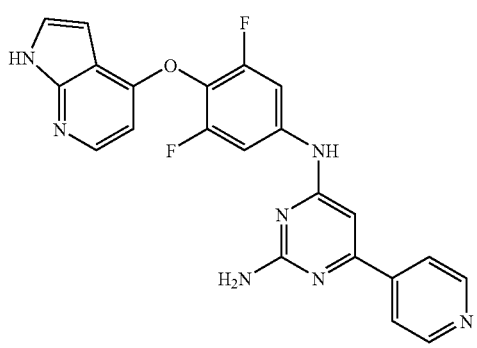

Analogously to example 25, the title compound is synthesized from 100 mg (0.36 mmol) of [3,5-difluoro-4-(1H-pyrrolo[2,3-b]pyridin-4-yloxy)phenyl]amine (from example XXXIV) and 87 mg (0.36 mmol) of 4-chloro-6-(4-pyridinyl)-2-pyrimidineamine (from example XXIX). Purification by preparative HPLC gives the product.

Yield: 67 mg (43% of theory)
LC-MS (Method 10): R$_t$=2.17 min
MS (ESI pos.): m/z=432 (M+H)$^+$
$^1$H-NMR (DMSO-d$_6$, 400 MHz): δ=6.32 (dd, 1H), 6.44 (d, 1H), 6.59 (s, 1H), 6.76 (br. s, 2H), 7.41 (dd, 1H), 7.82-7.88 (m, 4H), 8.09 (d, 1H), 8.72 (d, 2H), 9.85 (s, 1H), 11.83 (s, 1H).

Example 28

N$^4$-[4-(2,3-Dihydro-1H-pyrrolo[2,3-b]pyridin-4-yloxy)-3-fluorophenyl]-6-pyridin-4-ylpyrimidine-2,4-diamine

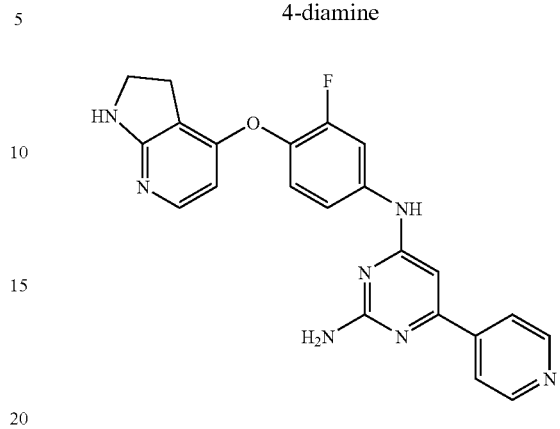

Analogously to example 25, the title compound is prepared from 19.7 mg (0.08 mmol) of [4-(2,3-dihydro-1H-pyrrolo[2,3-b]pyridin-4-yloxy)-3-fluoro-phenyl]amine (from example XLVI) and 17.4 mg (0.08 mmol) of 4-chloro-6-(4-pyridinyl)-2-pyrimidineamine (from example XXIX). Purification by preparative HPLC gives the product.

Yield: 7 mg (21% of theory)
LC-MS (Method 12): R$_t$=1.74 min
MS (ESI pos.): m/z=416 (M+H)$^+$
$^1$H-NMR (DMSO-d$_6$, 300 MHz): δ=2.85 (t, 2H), 3.50 (t, 2H), 5.92 (d, 1H), 6.55 (s, 1H), 6.60 (s, 2H), 6.85 (s, 1H), 7.22 (t, 1H), 7.40 (m, 1H), 7.62 (d, 1H), 7.85 (d, 2H), 8.30 (m, 1H), 8.70 (d, 2H), 9.62 (s, 1H).

Example 29

N$^4$-[4-(2,3-Dihydro-1H-pyrrolo[2,3-b]pyridin-4-yloxy)-3-fluorophenyl]-6-(4-fluoro-phenyl)pyrimidine-2,4-diamine

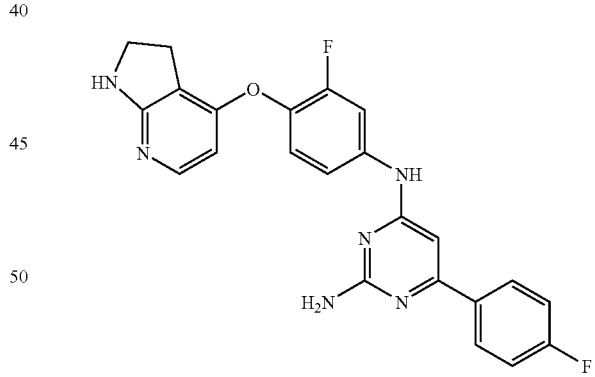

Analogously to example 25, the title compound is synthesized from 35 mg (0.14 mmol) of [4-(2,3-dihydro-1H-pyrrolo[2,3-b]pyridin-4-yloxy)-3-fluoro-phenyl]amine (from example XLVI) and 39 mg (0.15 mmol) of 4-chloro-6-(4-fluorophenyl)pyrimidine-2-amine (from example LIX). Purification by preparative HPLC gives the product.

Yield: 20 mg (32% of theory)
LC-MS (Method 9): R$_t$=2.35 min
MS (ESI pos.): m/z=433 (M+H)$^+$
$^1$H-NMR (DMSO-d$_6$, 300 MHz): δ=2.85 (t, 2H), 3.51 (t, 2H), 5.85 (d, 1H), 6.55-6.65 (m, 4H), 7.10-7.40 (m, 4H), 7.62 (d, 1H), 7.95 (m, 2H), 8.25 (m, 1H), 9.52 (s, 1H).

The following compounds are prepared analogously to example 25:

| Ex. No. | Starting materials (Ex. No.) | Structure | MS, HPLC, LC-MS, ¹H-NMR |
|---|---|---|---|
| 30 | XXIX | 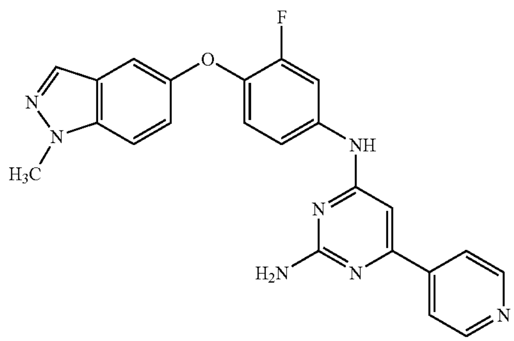 | MS (ESI pos.): m/z = 428 (M + H)⁺<br>HPLC (Method 7): $R_t$ = 3.86 min |
| 31 | LIII, XXIX | 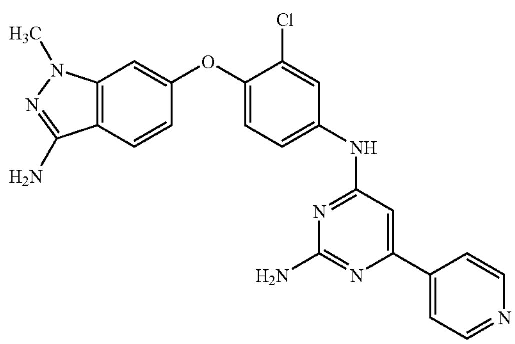 | MS (ESI pos.): m/z = 459 (M + H)⁺<br>LC-MS (Method 9): $R_t$ = 3.56 min<br>¹H-NMR (DMSO-d₆, 400 MHz): δ = 3.61 (s, 3 H), 5.42 (br. s, 2 H), 6.57–6.60 (m, 4 H), 6.74 (d, 1 H), 7.09 (d, 1 H), 7.63–7.68 (m, 2 H), 7.85 (d, 2 H), 8.17 (d, 1 H), 8.70 (d, 2 H), 9.56 (s, 1 H). |
| 32 | XXXVI, XXIX | 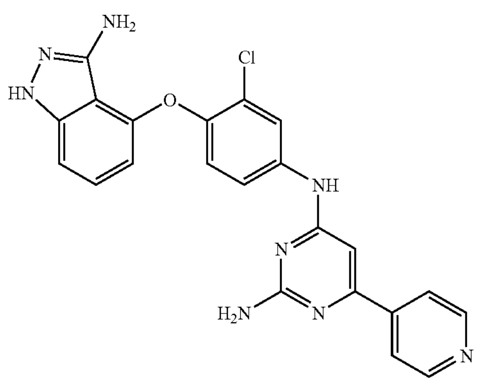 | MS (ESI pos.): m/z = 445 (M + H)⁺<br>HPLC (Method 7): $R_t$ = 3.40 min |
| 33 | XII, LIX | 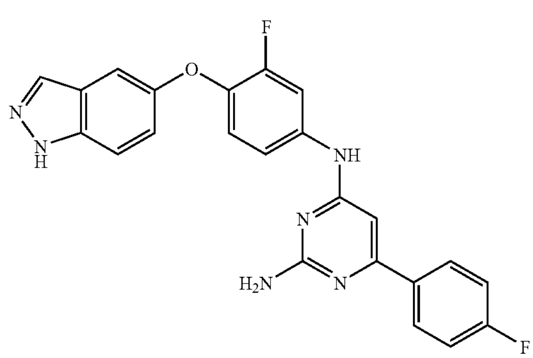 | MS (ESI pos.): m/z = 431 (M + H)⁺<br>HPLC (Method 7): $R_t$ = 4.18 min |

-continued

| Ex. No. | Starting materials (Ex. No.) | Structure | MS, HPLC, LC-MS, ¹H-NMR |
|---|---|---|---|
| 34 | XIII, LIX | 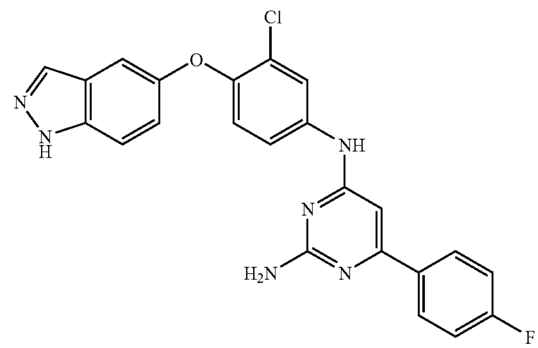 | MS (ESI pos.): m/z = 447 (M + H)⁺<br>HPLC (Method 7): $R_t$ = 4.21 min |
| 35 | LIII, LIX | 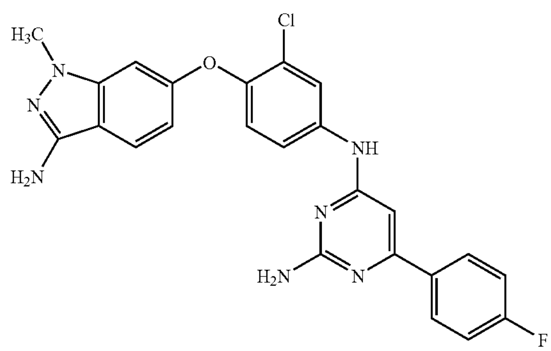 | MS (ESI pos.): m/z = 476 (M + H)⁺<br>LC-MS (Method 9): $R_t$ = 3.73 min |
| 36 | LIV, LIX | 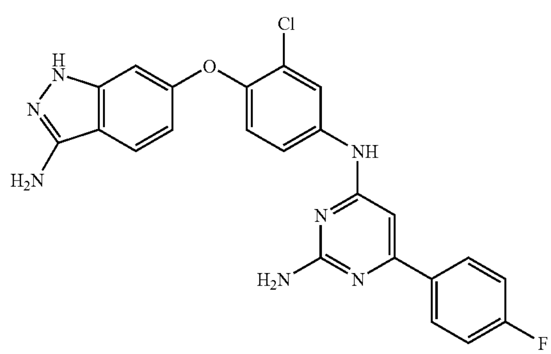 | MS (ESI pos.): m/z = 462 (M + H)⁺<br>LC-MS (Method 9): $R_t$ = 3.66 min<br>¹H-NMR (DMSO-$d_6$, 400 MHz): δ = 5.33 (s, 2 H), 6.45–6.48 (m, 4 H), 6.66 (d, 1 H), 7.15 (d, 1 H), 7.32 (dt, 2 H), 7.67 (mc, 2 H), 8.16 (d, 1 H), 9.46 (s, 1 H), 11.15 (s, 1 H). |
| 37 | XXXVI, LIX | 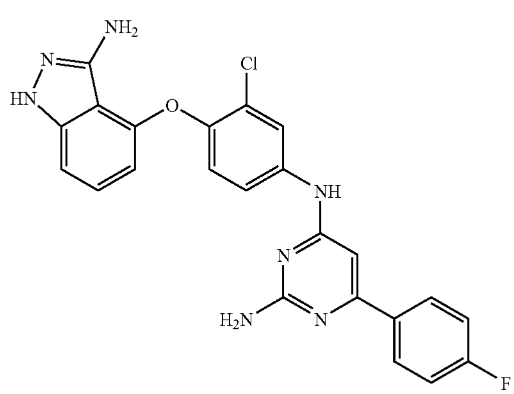 | MS (ESI pos.): m/z = 462 (M + H)⁺<br>HPLC (Method 7): $R_t$ = 3.91 min<br>¹H-NMR (DMSO-$d_6$, 400 MHz): δ = 5.05 (br. s, 2 H), 5.91 (d, 1 H), 6.47 (s, 3 H), 6.90 (d, 1 H), 7.06 (t, 1 H), 7.24 (d, 1 H), 7.32 (t, 2 H), 7.72 (dd, 1 H), 7.99 (dd, 2 H), 8.18 (d, 1 H), 9.47 (s, 1 H), 11.59 (s, 1 H). |

-continued

| Ex. No. | Starting materials (Ex. No.) | Structure | MS, HPLC, LC-MS, ¹H-NMR |
|---|---|---|---|
| 38 | XIX, LVII | (structure) | MS (ESI pos.): m/z = 448 (M + H)⁺<br>LC-MS (Method 10): $R_t$ = 2.21 min<br>¹H-NMR (DMSO-$d_6$, 400 MHz): δ = 6.27 (dd, 1 H), 6.37 (d, 1 H), 6.55 (s, 1 H), 6.65 (br. s, 2 H), 7.31 (t, 1 H), 7.37 (dd, 1 H), 7.66 (d, 1 H), 8.07 (d, 1 H), 8.28 (dd, 1 H), 8.32 (dd, 1 H), 8.93 (d, 1 H), 9.66 (s, 1 H), 11.75 (s, 1 H). |
| 39 | XIX, LVIII | (structure) | MS (ESI pos.): m/z = 416 (M + H)⁺<br>LC-MS (Method 9): $R_t$ = 1.94 min<br>¹H-NMR (400 MHz, DMSO-$d_6$): δ = 3.97 (s, 3 H), 6.09 (s, 1 H), 6.25 (m, 2 H), 6.36 (d, 1 H), 6.35 (m, 3 H), 6.53 (m, 1 H), 6.87 (s, 1 H), 7.28 (t, 1 H), 7.36 (m, 2 H), 8.06 (d, 1 H), 8.24 (dd, 1 H), 9.38 (s, 1 H), 11.74 (s, 1 H) |
| 40 | XIX, LXXIII | (structure) | MS (ESI pos.): m/z = 419.2 (M + H)⁺<br>HPLC (Method 7): $R_t$ = 3.98 min |
| 41 | XII, LVII | (structure) | MS (ESI pos.): m/z = 448 (M + H)⁺<br>LC-MS (Method 2): $R_t$ = 2.87 min |

| Ex. No. | Starting materials (Ex. No.) | Structure | MS, HPLC, LC-MS, ¹H-NMR |
|---|---|---|---|
| 42 | XII, LX | [structure] | MS (ESI pos.): m/z = 449 (M + H)⁺<br>HPLC (Method 7): $R_t$ = 4.18 min |
| 43 | XII, LXI | [structure] | MS (ESI pos.): m/z = 438 (M + H)⁺<br>HPLC (Method 11): $R_t$ = 4.17 min |
| 44 | XII, LVI | [structure] | MS (ESI pos.): m/z = 438 (M + H)⁺<br>HPLC (Method 11): $R_t$ = 4.06 min<br>¹H-NMR DMSO-$d_6$, 400 MHz): δ = 6.55 (s, 1 H), 6.57 (s, 2 H), 7.10 (t, 1 H), 7.14–7.18 (m, 2 H), 7.34 (dd, 1 H), 7.55 (d, 1 H), 7.72 (t, 1 H), 7.94 (d, 1 H), 7.98 (s, 1 H), 8.16–8.24 (m, 2 H), 8.34 (s, 1 H), 9.52 (s, 1 H), 13.06 (s, 1 H). |
| 45 | XII, LXII | [structure] | MS (ESI pos.): m/z = 438 (M + H)⁺<br>HPLC (Method 11): $R_t$ = 4.06 min |

-continued

| Ex. No. | Starting materials (Ex. No.) | Structure | MS, HPLC, LC-MS, ¹H-NMR |
|---|---|---|---|
| 46 | XII, LXIII | (1H-indazol-5-yloxy)-fluorophenyl-NH-pyrimidine(2-NH₂)-pyridin-3-yl | MS (ESI pos.): m/z = 414 (M + H)⁺<br>HPLC (Method 11): $R_t$ = 3.69 min |
| 47 | XII, LXIV | (1H-indazol-5-yloxy)-fluorophenyl-NH-pyrimidine(2-NH₂)-(6-methylpyridin-3-yl) | MS (ESI pos.): m/z = 428 (M + H)⁺<br>HPLC (Method 7): $R_t$ = 3.64 min |
| 48 | XII, LXV | (1H-indazol-5-yloxy)-fluorophenyl-NH-pyrimidine(2-NH₂)-(3-nitrophenyl) | MS (ESI pos.): m/z = 458 (M + H)⁺<br>HPLC (Method 7): $R_t$ = 4.13 min |
| 49 | XIII, LXVI | (1H-indazol-5-yloxy)-chlorophenyl-NH-pyrimidine(2-NH₂)-(4-bromophenyl) | MS (ESI pos.): m/z = 507 (M + H)⁺<br>HPLC (Method 7): $R_t$ = 4.35 min |

-continued

| Ex. No. | Starting materials (Ex. No.) | Structure | MS, HPLC, LC-MS, $^1$H-NMR |
|---|---|---|---|
| 50 | XIII, LXVII | 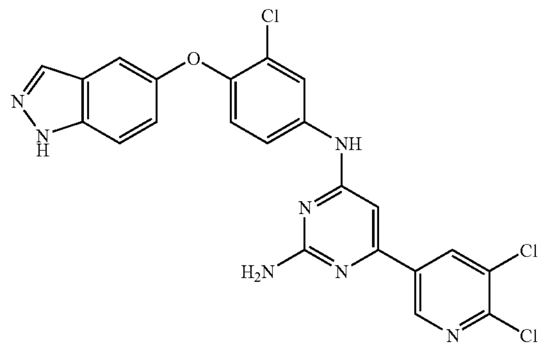 | MS (ESI pos.): m/z = 498 (M + H)$^+$<br>HPLC (Method 7): R$_t$ = 4.27 min<br>$^1$H-NMR (DMSO-d$_6$, 400 MHz): δ = 6.56 (s, 1 H), 6.62 (br. s, 2 H), 7.03 (d, 1 H), 7.11–7.17 (m, 2 H), 7.57 (d, 1 H), 7.63 (dd, 1 H), 7.98 (s, 1 H), 8.12 (d, 1 H), 8.53 (d, 1 H), 8.87 (d, 1 H), 9.52 (s, 1 H), 13.07 (s, 1 H). |
| 51 | XIII, LVII | 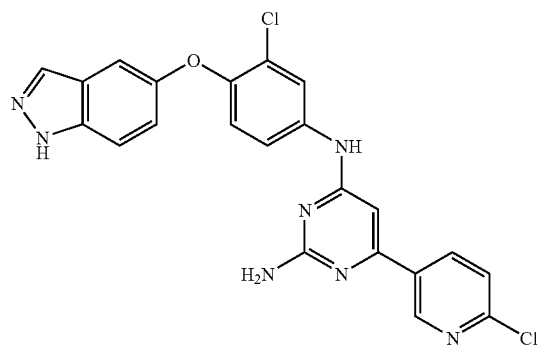 | MS (ESI pos.): m/z = 466 (M + H)$^+$<br>HPLC (Method 7): R$_t$ = 4.11 min<br>$^1$H-NMR (DMSO-d$_6$, 400 MHz): δ = 6.51 (s, 1 H), 6.57 (br. s, 2 H), 7.03 (d, 1 H), 7.12–7.16 (m, 2 H), 7.56 (d, 1 H), 7.62–7.66 (m, 2 H), 7.98 (s, 1 H), 8.13 (d, 1 H), 8.30 (dd, 1 H), 8.92 (d, 1 H), 9.51 (s, 1 H), 13.07 (s, 1 H). |
| 52 | XIII, LXVIII | 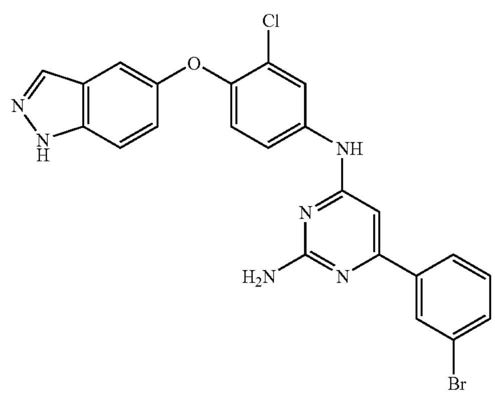 | MS (ESI pos.): m/z = 508 (M + H)$^+$<br>HPLC (Method 7): R$_t$ = 4.33 min |

Example 53

Methyl 2-amino-6-{[3-fluoro-4-(1H-pyrrolo[2,3-b]pyridin-4-yloxy)phenyl]amino}-pyrimidine-4-carboxylate

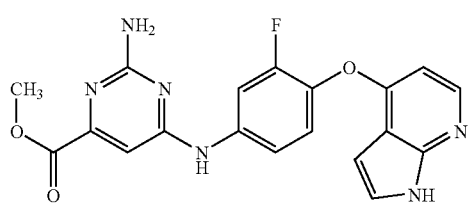

0.209 g (1.12 mmol) of methyl 2-amino-6-chloropyrimidine-4-carboxylate (prepared according to G. Doyle Daves, Fred Baiocchi, Roland K. Robins, and C. C. Cheng, *J. Org. Chem.*, 26 (1961), 2755-2763) and 0.4 g (1.12 mmol) of [3-fluoro-4-(1H-pyrrolo[2,3-b]pyridin-4-yloxy)phenyl]amine (example XIX) are suspended in 5 ml of water and 5 ml of ethanol. 0.11 ml (1.34 mmol) of 37% strength hydrochloric acid is added. The mixture is stirred at 100° C. for 18 hours. After cooling, the mixture is neutralized using an aqueous saturated sodium bicarbonate solution. The resulting precipitate is filtered off with suction and dried. This gives 0.46 g of product (68% of theory).

HPLC (Method 11): R$_t$=3.53 min

MS (ESI pos): m/z=395 (M+H)$^+$ $^1$H-NMR (400 MHz, DMSO-d$_6$): δ=3.82 (s, 3H), 6.17 (s, 1H), 6.25 (dd, 1H), 6.36 (d, 1H), 6.68 (s, 1H), 6.78 (s, 2H), 7.31 (t, 1H), 7.37 (dd, 2H), 7.39 (dd, 1H), 8.06 (d, 1H), 8.25 (dd, 1H), 9.76 (s, 1H), 11.75 (s, 1H).

Example 54

Methyl 2-amino-6-{[3-fluoro-4-(1H-indazol-5-yloxy)phenyl]amino}pyrimidine-4-carboxylate

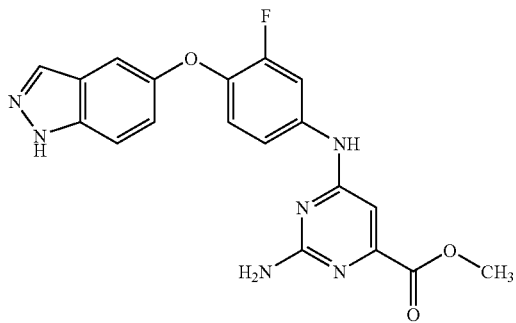

Analogously to example 53, the title compound is synthesized from 1.01 g (4.05 mmol) of 5-(4-amino-2-fluorophenoxy)-1H-indazole (from example XII) and 0.84 g (4.06 mmol) of methyl 2-amino-6-chloropyrimidine-4-carboxylate.

Yield: 1.55 g (93% of theory)

LC-MS (Method 16): R$_t$=1.56 min

MS (ESI pos.): m/z=395 (M+H)$^+$ $^1$H-NMR (300 MHz, DMSO-d$_6$): δ=3.85 (s, 3H), 6.72 (s, 1H), 7.101 (t, 1H), 7.15 (dd, 1H), 7.20 (d, 1H), 7.34 (m, 1H), 7.56 (d, 1H), 7.98 (s, 1H), 8.16 (dd, 1H), 10.04 (s, 1H), 13.06 (s, 1H).

Example 55

N$^4$-[3-Fluoro-4-(1H-pyrrolo[2,3-b]pyridin-4-yloxy)phenyl]-6-(piperazin-1-yl-carbonyl)pyrimidine-2,4-diamine

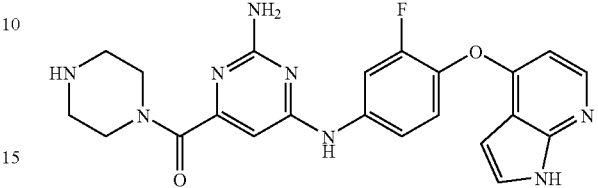

0.072 g (0.18 mmol) of methyl 2-amino-6-{[3-fluoro-4-(1H-pyrrolo[2,3-b]pyridin-4-yl-oxy)phenyl]amino}pyrimidine-4-carboxylate (from example 53) is suspended in 3 ml of water. 0.9 ml of a 1 molar sodium hydroxide solution is added. The reaction mixture is stirred at 100° C. for 18 hours. After cooling, the mixture is adjusted to pH 4.5 using 0.95 ml of a 1N hydrochloric acid solution. The precipitate formed is filtered off with suction and dried. The solid is suspended in DMF. 0.066 mg (0.175 mmol) of HATU, 0.025 g (0.184 mmol) of HOAT, 0.064 ml (0.368 mmol) of diisopropylethylamine and 0.031 g (0.368 mmol) of piperazine are added successively. The reaction mixture is stirred at 40° C. for 5 hours. After cooling, the solution is purified by preparative HPLC. This gives 0.012 g (15% of theory) of product.

LC-MS (Method 14): R$_t$=1.24 min

MS (ESI pos): m/z=449 (M+H)$^+$ $^1$H-NMR (200 MHz, DMSO-d$_6$): δ=2.76 (m, 4H), 3.54 (m, 4H), 6.05 (s, 1H), 6.25 (dd, 1H), 6.36 (d, 1H), 6.78 (s, 2H), 7.30 (t, 1H), 7.36 (m, 2H), 8.07 (d, 1H), 8.23 (dd, 1H), 9.62 (s, 1H), 11.77 (s, 1H).

The following compounds are prepared analogously to example 55:

| Ex. No. | Starting materials (Ex. No.) | Structure | MS, HPLC, LC-MS, $^1$H-NMR |
|---|---|---|---|
| 56 | 53 | 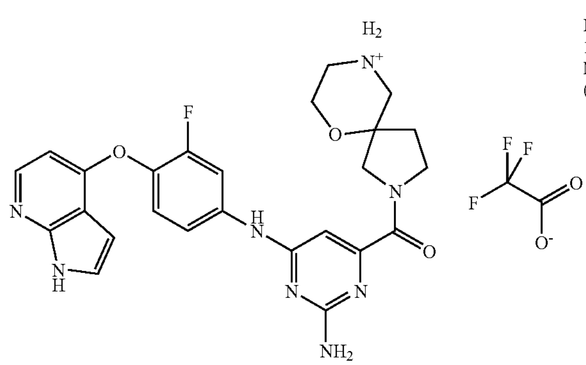 | LC-MS (Method 16): R$_t$ = 1.26 min<br>MS (ESI pos): m/z = 505 (M + H)$^+$ |

-continued

| Ex. No. | Starting materials (Ex. No.) | Structure | MS, HPLC, LC-MS, $^1$H-NMR |
|---|---|---|---|
| 57 | 53 | 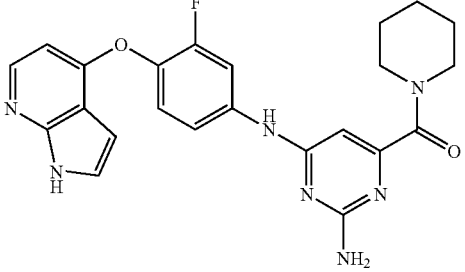 | LC-MS (Method 9): $R_t$ = 2.59 min<br>MS (ESI pos): m/z = 448 (M + H)$^+$ |
| 58 | 53 | 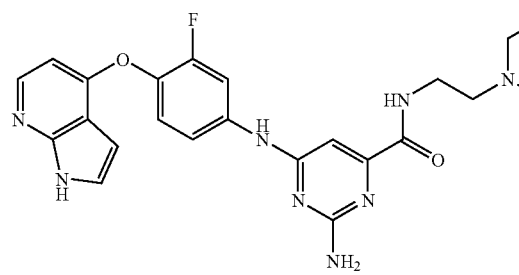 | LC-MS (Method 9): $R_t$ = 2.32 min<br>MS (ESI pos): m/z = 491 (M + H)$^+$ |
| 59 | 54 | 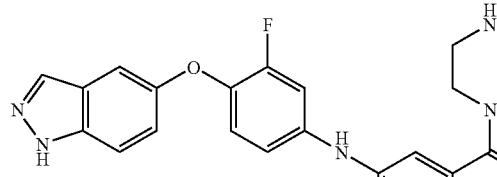 | LC-MS (Method 10): $R_t$ = 1.85 min<br>MS (ESI pos): m/z = 449 (M + H)$^+$ |

Example 60

6-Chloro-N$^4$-[3-fluoro-4-(1H-pyrrolo[2,3-b]pyridin-4-yloxy)phenyl]pyrimidine-2,4-diamine

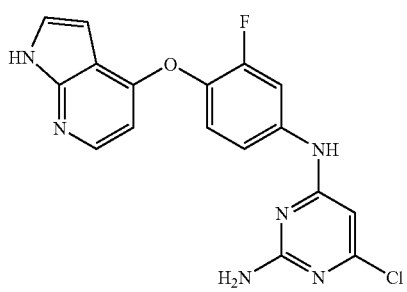

Analogously to example 8, the title compound is synthesized from 266 mg (1.09 mmol) of 3-fluoro-4-(1H-pyrrolo[2,3-b]pyridin-4-yloxy)aniline (from example XIX) and 179 mg (1.09 mmol) of 4,6-dichloro-2-pyrimidineamine.

Yield: 275 mg (68% of theory)
LC-MS (Method 10): $R_t$=2.41 min
MS (ESI pos.): m/z=371 (M+H)$^+$
$^1$H-NMR (DMSO-d$_6$, 300 MHz): δ=6.04 (s, 1H), 6.25 (dd, 1H), 6.36 (d, 1H), 6.86 (br. s, 2H), 7.25-7.37 (m, 3H), 8.07 (d, 1H), 8.17 (dd, 1H), 9.60 (s, 1H), 11.73 (s, 1H).

Example 61

6-Chloro-N$^4$-[3,5-difluoro-4-(1H-pyrrolo[2,3-b]pyridin-4-yloxy)phenyl]pyrimidine-2,4-diamine

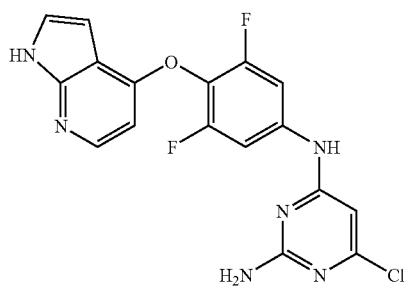

Analogously to example 8, the title compound is synthesized from 384 mg (1.47 mmol) of [3,5-difluoro-4-(1H-pyrrolo[2,3-b]pyridin-4-yloxy)phenyl]amine (from example XXXIV) and 241 mg (1.47 mmol) of 4,6-dichloro-2-pyrimidineamine.

Yield: 550 mg (96% of theory)
HPLC (Method 7): $R_t$=2.41 min
MS (ESI pos.): m/z=389 (M+H)$^+$
$^1$H-NMR (DMSO-d$_6$, 400 MHz): δ=6.04 (s, 1H), 6.31 (dd, 1H), 6.42 (d, 1H), 7.00 (br. s, 2H), 7.41 (dd, 1H), 7.75 (d, 2H), 8.08 (d, 1H), 9.79 (s, 1H), 11.83 (s, 1H).

Example 62

N$^4$-[3-Fluoro-4-(1H-pyrrolo[2,3-b]pyridin-4-yloxy)phenyl]-6-piperazin-1-ylpyrimidine-2,4-diamine

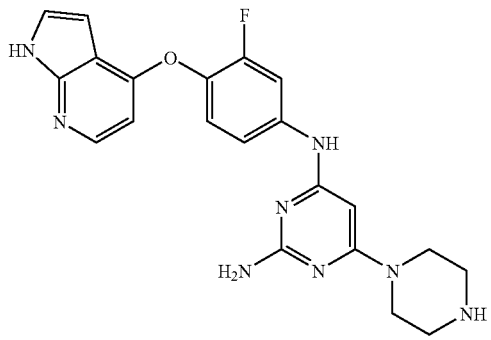

75 mg (0.20 mmol) of 6-chloro-N$^4$-[3-fluoro-4-(1H-pyrrolo[2,3-b]pyridin-4-yloxy)-phenyl]pyrimidine-2,4-diamine (from example 60) are dissolved in 3 ml of 1-butanol. 0.35 ml of N-ethyldiisopropylamine and 70 mg (0.81 mmol) of piperazine are added, and the mixture is heated at reflux for 5 hours. The solvent is then removed under reduced pressure and the residue is purified by preparative HPLC.

Yield: 37 mg (44% of theory)
LC-MS (Method 12): $R_t$=1.60 min
MS (ESI neg.): m/z=419 (M−H)$^−$ $^1$H-NMR (DMSO-d$_6$, 400 MHz): δ=2.75-2.82 (m, 4H), 3.24-3.26 (m, 2H), 3.41-3.44 (m, 2H), 4.18 (mc, 1H), 5.41 (s, 1H), 6.02 (br. s, 2H), 6.34 (mc, 1H), 6.42 (d, 1H), 7.30 (t, 1H), 7.35-7.38 (m, 1H), 7.44 (mc, 1H), 8.14 (d, 1H), 8.25 (dd, 1H), 9.07 (s, 1H), 11.81 (s, 1H).

Example 63

N$^4$-[3-Fluoro-4-(1H-pyrrolo[2,3-b]pyridin-4-yloxy)phenyl]-6-morpholin-4-yl-pyrimidine-2,4-diamine

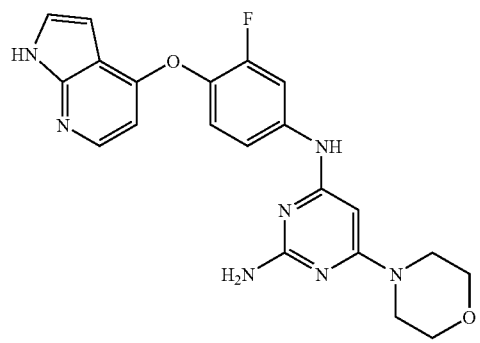

52 mg (0.14 mmol) of 6-chloro-N$^4$-[3-fluoro-4-(1H-pyrrolo[2,3-b]pyridin-4-yloxy)-phenyl]pyrimidine-2,4-diamine (from example 60) are dissolved in 2.5 ml of 2-ethylhexanol. 0.24 ml of N-ethyldiisopropylamine and 36 mg (0.42 mmol) of morpholine are added, and the mixture is heated at 150° C. bath temperature for 20 hours. After cooling, a little DMF is added and the mixture is chromatographed on silica gel 60 (gradient column: mobile phase: DCM:methanol=50:1, then 3:1). This gives an oil which is purified by preparative HPLC.

Yield: 13 mg (22% of theory)
HPLC (Method 7): $R_t$=3.61 min
MS (ESI pos.): m/z=422 (M+H)$^+$
$^1$H-NMR (DMSO-d$_6$, 400 MHz): δ=3.39 (mc, 4H), 3.66 (mc, 4H), 5.33 (s, 1H), 6.00 (br. s, 2H), 6.25 (mc, 1H), 6.32 (d, 1H), 7.22 (t, 1H), 7.27-7.30 (m 1H), 7.35 (dd, 1H), 8.05 (d, 1H), 8.17 (d, 1H), 9.05 (s, 1H), 11.73 (s, 1H).

The following compounds are prepared analogously to example 63:

| Ex. No. | Starting materials (Ex. No.) | Structure | MS, HPLC, LC-MS, $^1$H-NMR |
|---|---|---|---|
| 64 | 61 | (structure shown) | MS (ESI pos.): m/z = 467 (M + H)$^+$<br>LC-MS (Method 15): $R_t$ = 1.05 min |

-continued

| Ex. No. | Starting materials (Ex. No.) | Structure | MS, HPLC, LC-MS, $^1$H-NMR |
|---|---|---|---|
| 65 | 61 | 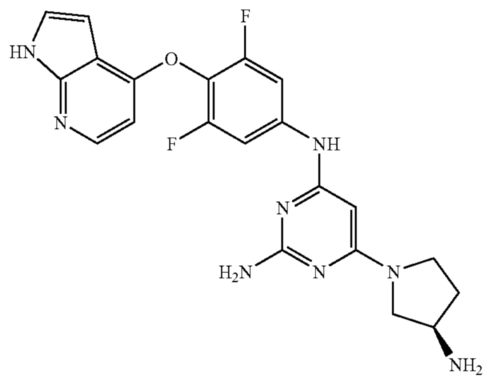 | MS (ESI pos.): m/z = 439 (M + H)$^+$<br>LC-MS (Method 9): R$_t$ = 1.50 min |
| 66 | 60 | 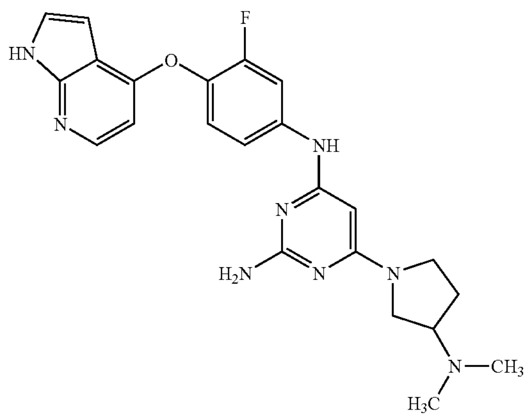 | MS (ESI neg.): m/z = 447 (M − H)$^-$<br>LC-MS (Method 12): R$_t$ = 1.59 min |
| 67 | 60 | 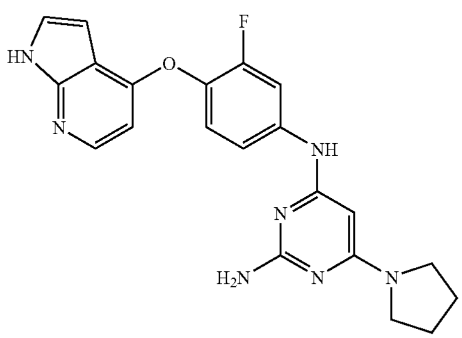 | MS (ESI pos.): m/z = 406 (M + H)$^+$<br>LC-MS (Method 16): R$_t$ = 1.50 min |
| 68 | 60 | 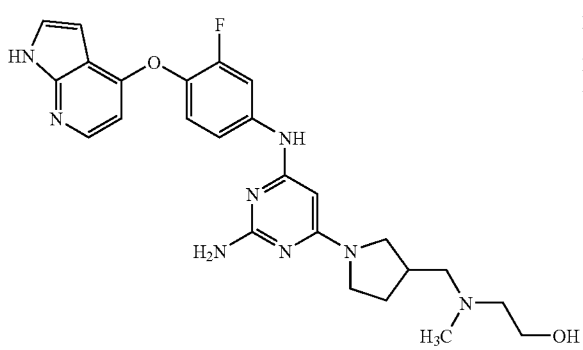 | MS (ESI pos.): m/z = 493 (M + H)$^+$<br>HPLC (Method 11): R$_t$ = 3.46 min |

-continued

| Ex. No. | Starting materials (Ex. No.) | Structure | MS, HPLC, LC-MS, ¹H-NMR |
|---|---|---|---|
| 69 | 60 | (structure) | MS (ESI pos.): m/z = 461 (M + H)⁺<br>LC-MS (Method 10): $R_t$ = 1.67 min |
| 70 | 60 | (structure) | LC-MS (Method 12): $R_t$ = 1.52 min |
| 71 | 60 | (structure) | MS (ESI neg.): m/z = 419 (M − H)⁻<br>LC-MS (Method 12): $R_t$ = 1.53 min |
| 72 | 60 | (structure) | MS (ESI pos.): m/z = 435 (M + H)⁺<br>LC-MS (Method 13): $R_t$ = 1.10 min |

-continued

| Ex. No. | Starting materials (Ex. No.) | Structure | MS, HPLC, LC-MS, ¹H-NMR |
|---|---|---|---|
| 73 | 60 | (structure) | MS (ESI pos.): m/z = 450 (M + H)⁺<br>LC-MS (Method 9): $R_t$ = 1.95 min |
| 74 | 60 | (structure) | MS (ESI pos.): m/z = 461 (M + H)⁺<br>LC-MS (Method 16): $R_t$ = 1.18 min |
| 75 | 60 | (structure) | MS (ESI pos.): m/z = 447 (M + H)⁺<br>LC-MS (Method 9): $R_t$ = 2.01 min |
| 76 | 60 | (structure) | MS (ESI pos.): m/z = 422 (M + H)⁺<br>LC-MS (Method 16): $R_t$ = 1.36 min |

| Ex. No. | Starting materials (Ex. No.) | Structure | MS, HPLC, LC-MS, ¹H-NMR |
|---|---|---|---|
| 77 | 60 | (structure) | MS (ESI pos.): m/z = 511 (M + H)⁺<br>HPLC (Method 11): $R_t$ = 3.94 min |
| 78 | XIX | (structure) | MS (ESI pos.): m/z = 366 (M + H)⁺<br>LC-MS (Method 16): $R_t$ = 1.39 min |
| 79 | 60 | (structure) | MS (ESI pos.): m/z = 447 (M + H)⁺<br>LC-MS (Method 9): $R_t$ = 1.37 min |
| 80 | 60 | (structure) | MS (ESI pos.): m/z = 435 (M + H)⁺<br>LC-MS (Method 10): $R_t$ = 2.13 min |

-continued
| Ex. No. | Starting materials (Ex. No.) | Structure | MS, HPLC, LC-MS, ¹H-NMR |
|---|---|---|---|
| 81 | 60 | 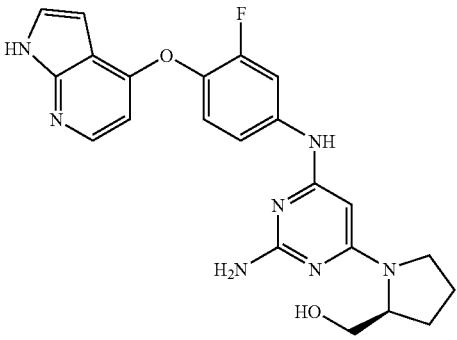 | MS (ESI pos.): m/z = 436 (M + H)⁺<br>LC-MS (Method 9): $R_t$ = 1.82 min |
| 82 | 60 | 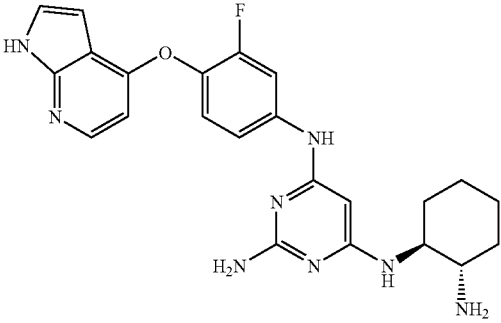 | MS (ESI pos.): m/z = 449 (M + H)⁺<br>HPLC (Method 7): $R_t$ = 3.57 min |
| 83 | 60 | 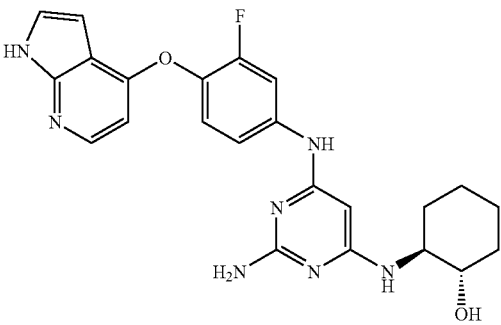 | MS (ESI pos.): m/z = 450 (M + H)⁺<br>LC-MS (Method 15): $R_t$ = 1.33 min |
| 84 | 60 | 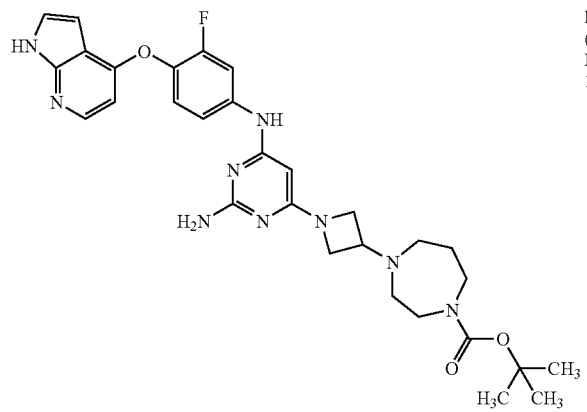 | MS (ESI pos.): m/z = 590 (M + H)⁺<br>LC-MS (Method 14): $R_t$ = 1.57 min |

| Ex. No. | Starting materials (Ex. No.) | Structure | MS, HPLC, LC-MS, ¹H-NMR |
|---|---|---|---|
| 85 | 60 | (structure) | MS (ESI pos.): m/z = 489 (M + H)⁺<br>LC-MS (Method 13): R$_t$ = 1.34 min |
| 86 | 60 | (structure) | MS (ESI pos.): m/z = 477 (M + H)⁺<br>LC-MS (Method 17): R$_t$ = 1.21 min |
| 87 | 60 | (structure) | MS (ESI pos.): m/z = 519 (M + H)⁺<br>LC-MS (Method 10): R$_t$ = 2.12 min |
| 88 | 60 | (structure) | MS (ESI pos.): m/z = 411 (M + H)⁺<br>LC-MS (Method 9): R$_t$ = 1.93 min<br>¹H-NMR (DMSO-d$_6$, 400 MHz): δ= 3.30 (s, 3H), 3.59 (dd, 2 H), 4.29 (dd, 2 H), 5.39 (s, 1 H), 6.25 (d, 1 H), 6.34 (d, 1 H), 6.41 (br. s, 2 H), 7.22-7.36 (m, 3 H), 8.06 (d, 1 H), 8.12–8.18 (m, 1 H), 9.27 (s, 1 H), 11.74 (s, 1 H). |

-continued

| Ex. No. | Starting materials (Ex. No.) | Structure | MS, HPLC, LC-MS, $^1$H-NMR |
|---|---|---|---|
| 89 | 8 | 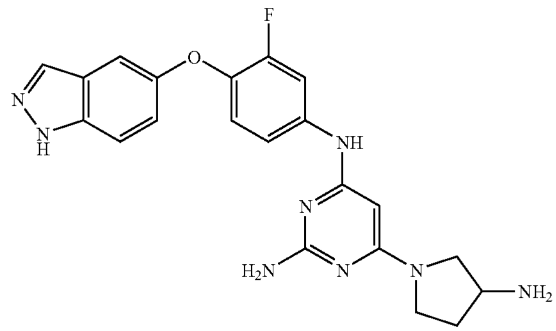 | MS (ESI pos.): m/z = 421 (M + H)$^+$<br>LC-MS (Method 2): R$_t$ = 2.20 min |
| 90 | 8 | 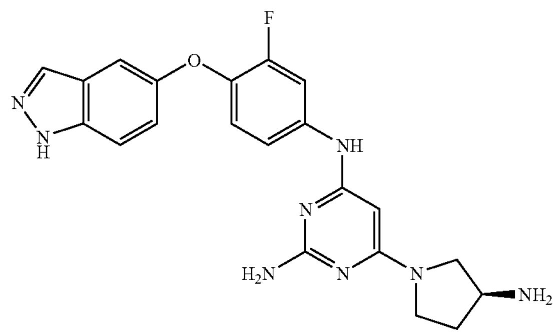 | MS (ESI pos.): m/z = 421 (M + H)$^+$<br>LC-MS (Method 2): R$_t$ = 2.20 min |
| 91 | 8 | 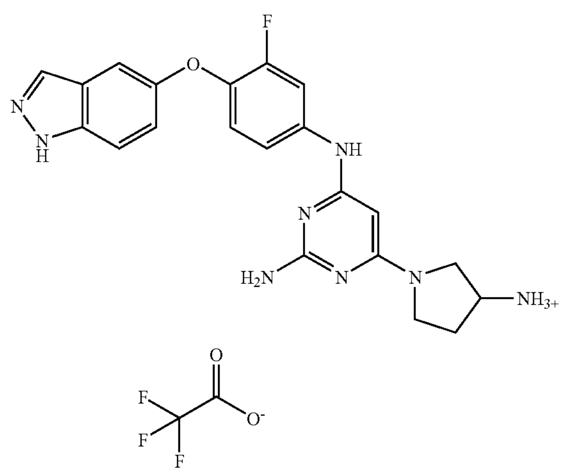 | MS (ESI pos.): m/z = 421 (M + H)$^+$<br>LC-MS (Method 8): R$_t$ = 1.91 min |
| 92 | 8 | 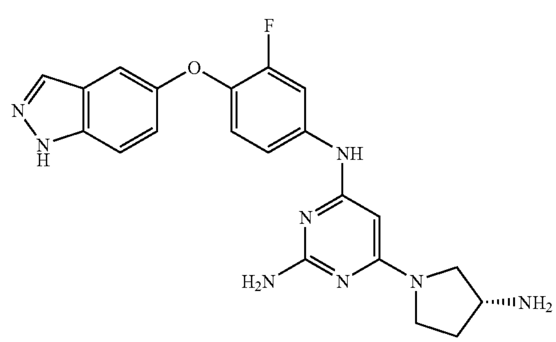 | MS (ESI pos.): m/z = 421 (M + H)$^+$<br>LC-MS (Method 2): R$_t$ = 2.20 min |

-continued

| Ex. No. | Starting materials (Ex. No.) | Structure | MS, HPLC, LC-MS, ¹H-NMR |
|---|---|---|---|
| 93 | 8 | (structure) | MS (ESI pos.): m/z = 435 (M + H)⁺<br>HPLC (Method 7): $R_t$ = 3.56 min |
| 94 | 8 | (structure) | MS (ESI pos.): m/z = 449 (M + H)⁺<br>HPLC (Method 7): $R_t$ = 3.59 min |
| 95 | 8 | (structure) | MS (ESI pos.): m/z = 492 (M + H)⁺<br>LC-MS (Method 8): $R_t$ = 2.45 min |
| 96 | 8 | (structure) | MS (ESI pos.): m/z = 422 (M + H)⁺<br>LC-MS (Method 2): $R_t$ = 2.50 min |

-continued
| Ex. No. | Starting materials (Ex. No.) | Structure | MS, HPLC, LC-MS, $^1$H-NMR |
|---|---|---|---|
| 97 | 9 | 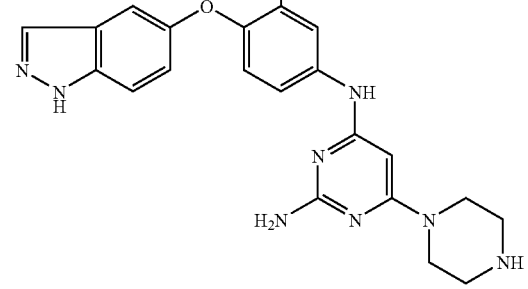 | MS (ESI pos.): m/z = 435 (M + H)$^+$<br>LC-MS (Method 10): R$_t$ = 1.63 min |
| 98 | 9 | 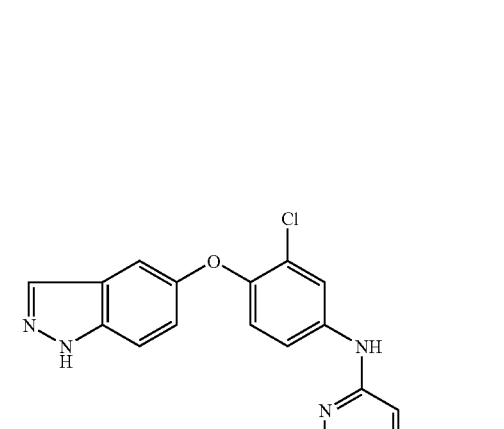 | MS (ESI pos.): m/z = 438 (M + H)$^+$<br>HPLC (Method 7): R$_t$ = 3.89 min |
| 99 | 60 | 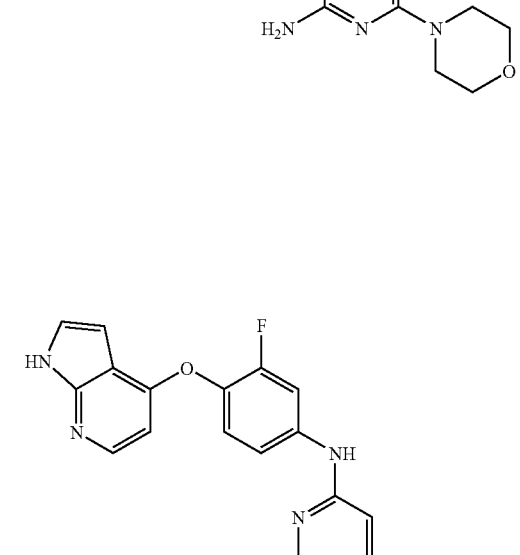 | MS (ESI pos.): m/z = 488 (M + H)$^+$<br>HPLC (Method 7): R$_t$ = 3.83 min |

Example 100

6-[3-(1,4-Diazepan-1-yl)azetidin-1-yl]-N-4-[3-fluoro-4-(1H-pyrrolo[2,3-b]pyridin-4-yloxy)phenyl]pyrimidine-2,4-diamine

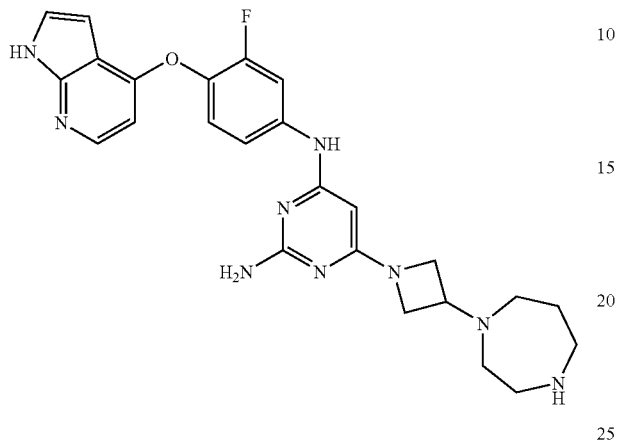

34 mg (0.06 mmol) of the compound from example 84 in 1 ml of a 4 molar solution of hydrogen chloride and dioxane are stirred at RT. The mixture is then concentrated under reduced pressure and the residue is triturated with diethyl ether. The solvent is decanted off and the residue is dried under high vacuum, which gives the hydrochloride of the title compound.

Yield: 30 mg (96% of theory)
LC-MS (Method 17): $R_t$=1.18 min
MS (ESI pos.): m/z=490 (M+H)$^+$

Example 101

3-[(2-Amino-6-{[3-fluoro-4-(1H-pyrrolo[2,3-b]pyridin-4-yloxy)phenyl]amino}-pyrimidin-4-yl)amino]propan-1-ol

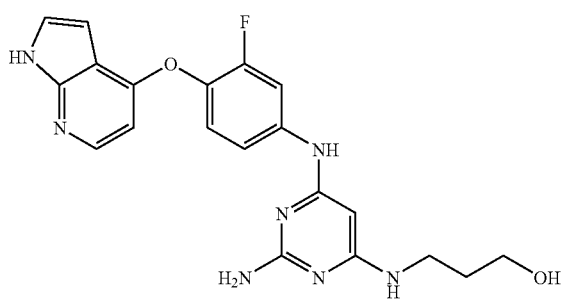

78 mg (0.21 mmol) of 6-chloro-N$^4$-[3-fluoro-4-(1H-pyrrolo[2,3-b]pyridin-4-yloxy)-phenyl]pyrimidine-2,4-diamine (from example 60), 190 mg (0.84 mmol) of 3-[(2,4-dimethoxybenzyl)amino]propan-1-ol in 1 ml of 1-butanol and 0.37 ml of N-ethyl-diisopropylamine are, in a closed pressure vessel, heated at 130° C. overnight. Volatile components are removed under reduced pressure, and the residue is purified by preparative HPLC. The substrate obtained is taken up in 2 ml of DCM, and 0.5 ml of TFA is added. The mixture is stirred at RT for 20 min and then poured into ethyl acetate and extracted with sat. sodium carbonate solution. The organic phase is dried over sodium sulfate and the solvent is removed under reduced pressure. The residue is purified by preparative HPLC.

Yield: 10 mg (16% of theory)
LC-MS (Method 10): $R_t$=1.85 min
MS (ESI pos.): m/z=410 (M+H)$^+$

Example 102

N$^4$-[3-Fluoro-4-(1H-indazol-5-yloxy)phenyl]-6-[4-(trifluoromethyl)phenyl]-pyrimidine-2,4-diamine

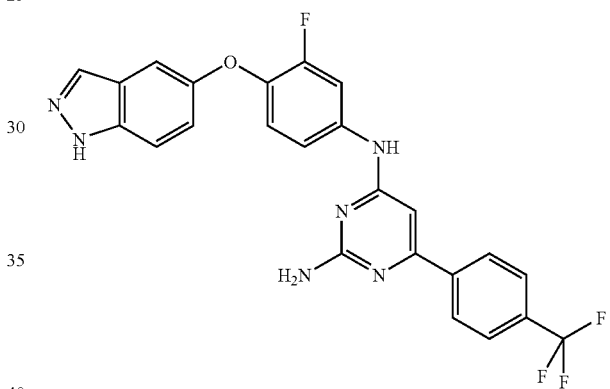

52.55 mg (0.14 mmol) of 6-chloro-N$^4$-[3-fluoro-4-(1H-indazol-5-yloxy)phenyl]pyrimidine-2,4-diamine (from example 8) and 35.71 mg (0.42 mmol) of sodium bicarbonate are stirred in 2.4 ml of dimethoxyethane and 0.7 ml of water at 85° C. for 30 minutes. 5 mg (0.007 mmol) of 1,1'-bis(diphenylphosphino)ferrocene-palladium(II) chloride are added. The mixture is stirred at 85° C. for 12 hours. For work-up, the mixture is diluted with dimethoxyethane and washed with a saturated sodium chloride solution. The organic phase is dried and concentrated. The residue is purified by preparative HPLC. This gives 2.80 g (65% of theory) of product.

LC-MS (Method 16): $R_t$=1.84 min
MS (ESI pos): m/z=481 (M+H)$^+$ $^1$H-NMR (200 MHz, DMSO-d$_6$): δ=6.57 (s, 3H), 7.10 (dd, 1H), 7.16 (m, 2H), 7.34 (dd, 1H), 7.56 (d, 1H), 7.86 (d, 2H), 7.98 (s, 1H), 8.14 (m, 2H), 8.21 (dd, 1H), 9.56 (s, 1H), 13.07 (s, 1H).

The following compounds are prepared analogously to example 102:

| Ex. No. | Starting materials (Ex. No.) | Structure | MS, HPLC, LC-MS, ¹H-NMR |
|---|---|---|---|
| 103 | 8 | (indazole-O-fluorophenyl-NH-pyrimidine(NH₂)-phenyl-N(CH₃)₂) | MS (ESI pos.): m/z = 456 (M + H)⁺<br>LC-MS (Method 16): R$_t$ = 1.84 min<br>¹H-NMR (200 MHz, DMSO-d$_6$): δ = 2.97 (s, 6 H), 6.29 (s, 2 H), 6.27 (s, 1 H), 6.77 (d, 2 H), 7.08 (t, 1 H), 7.15 (m, 2 H), 7.31 (dd, 1 H), 7.54 (d, 1 H), 7.82 (d, 2 H), 7.97 (s, 1 H), 8.19 (dd, 1 H), 9.56 (s, 1 H), 13.07 (s, 1 H). |
| 104 | 8 | (indazole-O-fluorophenyl-NH-pyrimidine(NH₂)-phenyl-NO₂) | MS (ESI pos.): m/z = 458 (M + H)⁺<br>LC-MS (Method 10): R$_t$ = 2.4 min |
| 105 | 60 | (7-azaindole-O-fluorophenyl-NH-pyrimidine(NH₂)-phenyl-morpholine) | MS (ESI pos.): m/z = 498 (M + H)⁺<br>LC-MS (Method 16): R$_t$ = 1.58 min |
| 106 | 60 | (7-azaindole-O-fluorophenyl-NH-pyrimidine(NH₂)-phenyl-CH₂OH) | MS (ESI pos.): m/z = 443 (M + H)⁺<br>LC-MS (Method 12): R$_t$ = 2.10 min |

-continued

| Ex. No. | Starting materials (Ex. No.) | Structure | MS, HPLC, LC-MS, $^1$H-NMR |
|---|---|---|---|
| 107 | 60 | 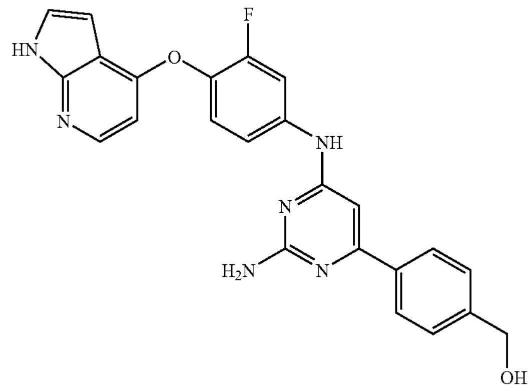 | MS (ESI pos.): m/z = 443 (M + H)$^+$<br>LC-MS (Method 9): R$_t$ = 1.85 min<br>$^1$H-NMR DMSO-d$_6$, 400 MHz): δ = 4.56 (d, 2 H), 5.27 (t, 1 H), 6.27 (dd, 1 H), 6.36 (d, 1 H), 6.48 (s, 2 H), 6.52 (s, 1 H), 7.30 (t, 1 H), 7.36–7.44 (m, 4 H), 7.92 (d, 2 H), 8.07 (d, 1 H), 8.28 (dd,1 H), 9.54 (s, 1 H), 11.75 (s, 1 H). |
| 108 | 60 | 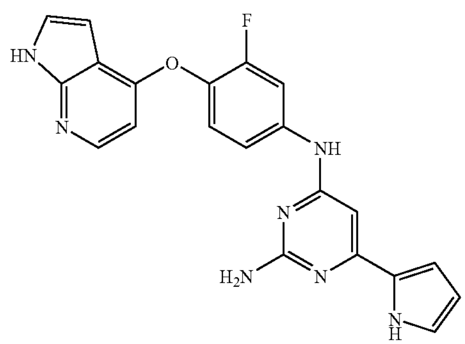 | MS (ESI pos.): m/z = 402 (M + H)$^+$<br>LC-MS (Method 9): R$_t$ = 1.83 min |

Example 109

N$^4$-[3-Fluoro-4-(1H-indazo-5-yloxy)phenyl]pyrimidine-2,4,6-triamine

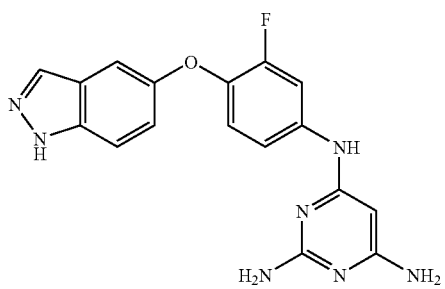

Analogously to example 25, the title compound is synthesized from 150 mg (0.62 mmol) of [3-fluoro-4-(1H-indazol-5-yloxy)phenyl]amine (from example XII) and 94 mg (0.65 mmol) of 6-chloropyrimidine-2,4-diamine. Purification by preparative HPLC gives the product.

Yield: 11 mg (5% of theory)
LC-MS (Method 8): R$_t$=2.10 min
MS (ESI pos.): m/z=416 (M+H)$^+$ $^1$H-NMR (DMSO-d$_6$, 300 MHz): δ=5.19 (m, 1H), 5.67 (m, 2H), 5.82 (m, 2H), 7.02 (t, 1H), 7.10-7.30 (m, 3H), 7.53 (m, 1H), 7.90-8.10 (m, 2H), 8.70 (s, 1H), 13.00 (s, 1H).

Example 110

4-[(2-Amino-6-{[3-fluoro-4-(1H-pyrrolo[2,3-b]pyridin-4-yloxy)phenyl]amino}-pyrimidin-4-yl)amino]benzonitrile

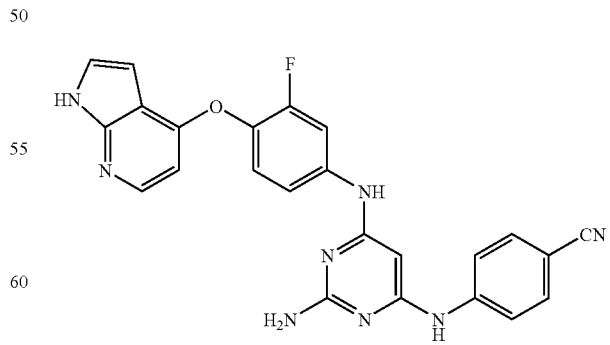

Analogously to example 25, the title compound is synthesized from 51 mg (0.21 mmol) of [3-fluoro-4-(1H-pyrrolo[2,3-b]pyridin-4-yloxy)phenyl]amine (from example XIX) and 54 mg (0.22 mmol) of 4-[(2-amino-6-chloropyrimidin-4-yl)amino]benzonitrile (from example XLVII). Purification by preparative HPLC gives the product.

Yield: 8 mg (8% of theory)
LC-MS (Method 8): $R_t$=2.30 min
MS (ESI pos.): m/z=453 (M+H)$^+$ $^1$H-NMR (DMSO-$d_6$, 300 MHz): δ=5.62 (s, 1H), 6.25 (m, 1H), 6.30 (s, 2H), 6.35 (d, 1H), 7.25 (m, 1H), 7.30-7.40 (m, 2H), 7.65 (d, 2H), 7.90 (d, 2H), 8.00-8.19 (m, 2H), 9.15 (s, 1H), 9.35 (s, 1H), 11.70 (s, 1H).

The following compounds are prepared analogously to example 110:

| Ex. No. | Starting materials (Ex. No.) | Structure | MS, HPLC, LC-MS, $^1$H-NMR |
|---|---|---|---|
| 111 | XIX, XLVIII | 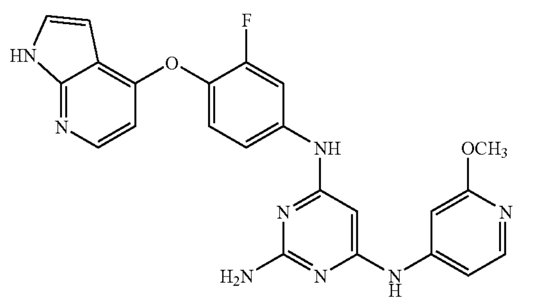 | MS (ESI pos.): m/z = 459 (M + H)$^+$<br>LC-MS (Method 9): $R_t$ = 1.95 min |
| 112 | XIX, XLIX | 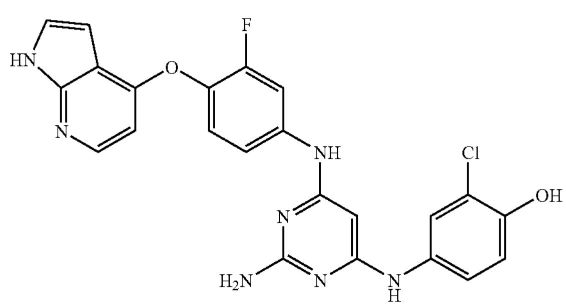 | MS (ESI pos.): m/z = 478 (M + H)$^+$<br>LC-MS (Method 16): $R_t$ = 1.53 min |
| 113 | XIX, XLIII | 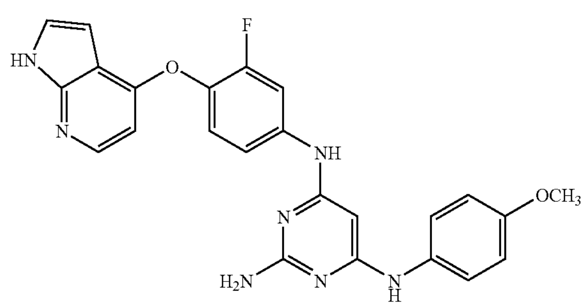 | LC-MS (Method 2): $R_t$ = 2.73 min |

| Ex. No. | Starting materials (Ex. No.) | Structure | MS, HPLC, LC-MS, ¹H-NMR |
|---|---|---|---|
| 114 | XIX, L | (structure) | MS (ESI pos.): m/z = 444 (M + H)⁺<br>LC-MS (Method 16): $R_t$ = 1.26 min |
| 115 | XIX, LI | (structure) | MS (ESI pos.): m/z = 418 (M + H)⁺<br>LC-MS (Method 10): $R_t$ = 1.90 min |

Example 116

Benzyl 6-[(tert-butylamino)methyl]-N⁴-[3-fluoro-4-(1H-pyrrolo[2,3-b]pyridin-4-yloxy)phenyl]pyrimidine-2,4-diamine

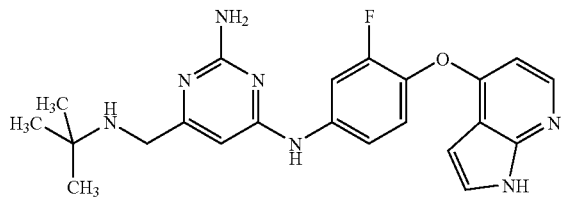

0.060 g (0.28 mmol) of 4-[(tert-butylamino)methyl]-6-chloropyrimidine-2-amine and 4-[(tert-butylamino)methyl]-6-bromopyrimidine-2-amine (from example LXXX) and 0.068 g (0.28 mmol) of [3-fluoro-4-(1H-pyrrolo[2,3-b]pyridin-4-yloxy)phenyl]amine (from example XIX) are suspended in 2 ml of water and 2 ml of ethanol. 0.051 ml (0.61 mmol) of 37% strength hydrochloric acid is added. The mixture is stirred at 100° C. for 18 hours. After cooling, the mixture is neutralized using a 12N sodium hydroxide solution. After addition of 1 ml of DMSO, the suspension is re-dissolved and purified by preparative HPLC. This gives 0.074 g (63% of theory) of product.

LC-MS (Method 15): $R_t$=1.12 min
MS (ESI pos): m/z=422 (M+H)⁺
¹H-NMR (200 MHz, DMSO-$d_6$): δ=1.11 (s, 9H), 3.52 (s, 2H), 6.17 (s, 1H), 6.27 (m, 1H), 6.34 (m, 3H), 7.27 (t, 1H), 7.39 (m, 2H), 8.06 (d, 1H), 8.24 (dd, 1H), 9.46 (s, 1H), 11.76 (s, 1H).

Example 117

N⁴-[3-Fluoro-4-(1H-pyrrolo[2,3-b]pyridin-4-yloxy)phenyl]-6-(piperidin-1-ylmethyl)-pyrimidine-2,4-diamine

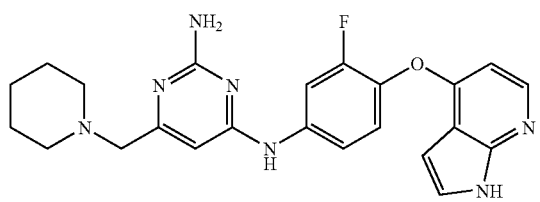

Analogously to example 116, the title compound is obtained by reacting 33 mg (0.137 mmol) of [3-fluoro-4-(1H-pyrrolo[2,3-b]pyridin-4-yloxy)phenyl]amine (from example XIX) and 31 mg (0.137 mmol) of 4-chloro-6-(piperidin-1-ylmethyl)pyrimidine-2-amine (from example LXXXI).

Yield: 13 mg (22% of theory)
LC-MS (Method 13): $R_t$=1.39 min
MS (ESI pos): m/z=218½(M+H)²⁺
¹H-NMR (200 MHz, DMSO-$d_6$): δ=1.42 (m, 2H), 1.54 (m, 4H), 2.39 (m, 4H), 3.17 (d, 2H), 4.06 (q, 1H), 6.19 (s, 1H), 6.24 (dd, 1H), 6.28 (s, 2H), 6.35 (d, 1H), 7.26 (t, 1H), 7.37 (m, 2H), 8.06 (d, 1H), 8.21 (dd, 1H), 9.37 (s, 1H), 11.71 (s, 1H).

The following compounds are prepared analogously to example 116:

| Ex. No. | Starting materials (Ex. No.) | Structure | MS, HPLC, LC-MS, ¹H-NMR |
|---|---|---|---|
| 118 | LXXXV XIX | 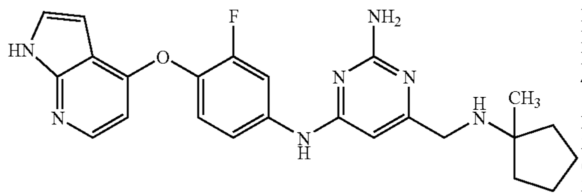 | LC-MS (Method 15): $R_t$ = 1.22 min<br>MS (ESI pos): m/z = 448 (M + H)⁺<br>¹H-NMR (300 MHz, DMSO-d₆): δ = 1.14 (s, 3 H), 1.24 (m, 1 H), 1.40 (m, 2 H), 1.62 (m, 6 H), 3.43 (s, 2 H), 6.23 (m, 4 H), 6.34 (d, 1 H), 7.25 (t, 1 H), 7.37 (m, 2 H), 8.06 (d, 1 H), 8.21 (dd, 1 H), 9.37 (s, 1 H), 11.71 (s, 1 H). |
| 119 | LXXXIX XIX | 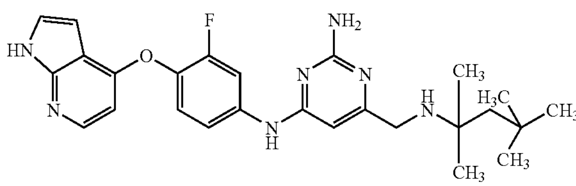 | LC-MS (Method 15): $R_t$ = 1.53 min<br>MS (ESI pos): m/z = 478 (M + H)⁺ |
| 120 | LXXXII XIX | 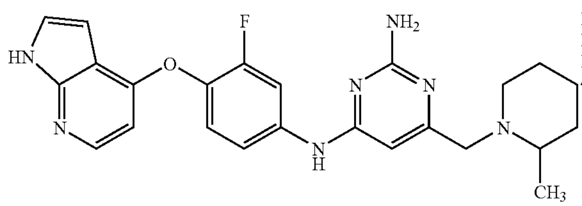 | LC-MS (Method 15): $R_t$ = 1.19 min<br>MS (ESI pos): m/z = 448 (M + H)⁺ |
| 121 | LXXXVIII XIX | 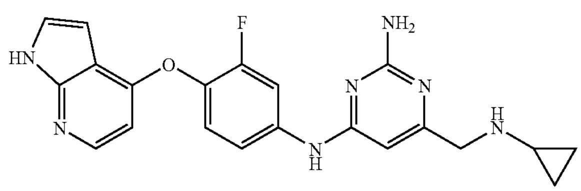 | LC-MS (Method 15): $R_t$ = 1.14 min<br>MS (ESI pos): m/z = 204 1/2 (M + H)²⁺<br>¹H-NMR (200 MHz, DMSO-d₆): δ = 0.28 (m, 2 H), 0.37 (m, 2 H), 2.12 (m, 1 H), 3.50 (s, 2 H), 6.11 (s, 1 H), 6.26 (m, 1 H), 6.36 (m, 3 H), 7.27 (t, 1 H), 7.36 (m, 2 H), 8.06 (d, 1 H), 8.23 (dd, 1 H), 9.40 (s, 1 H), 11.75 (s, 1 H). |
| 122 | LXXXIV XIX | 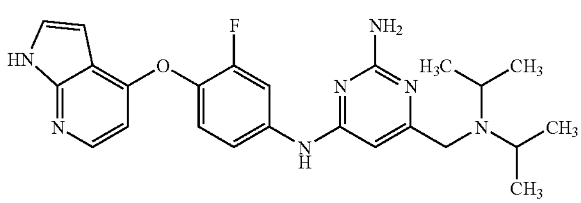 | LC-MS (Method 13): $R_t$ = 1.59 min<br>MS (ESI pos): m/z = 451 (M + H)⁺ |
| 123 | LXXXIII XIX | 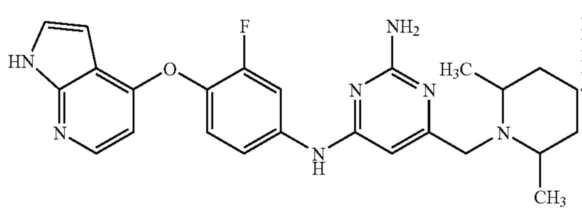 | LC-MS (Method 15): $R_t$ = 1.31 min<br>MS (ESI pos): m/z = 462 (M + H)⁺ |

-continued

| Ex. No. | Starting materials (Ex. No.) | Structure | MS, HPLC, LC-MS, $^1$H-NMR |
|---|---|---|---|
| 124 | LXXXVI XIX | 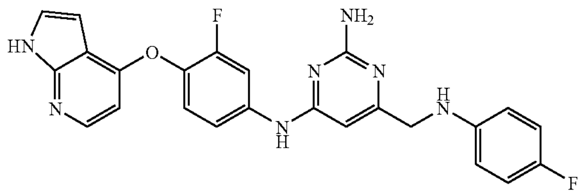 | LC-MS (Method 13): $R_t$ = 1.76 min<br>MS (ESI pos): m/z = 460 (M + H)$^+$ |
| 125 | LXXXVII XIX | 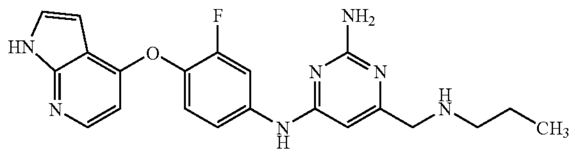 | LC-MS (Method 13): $R_t$ = 1.59 min<br>MS (ESI pos): m/z = 408 (M + H)$^+$ |
| 126 | LXXX XII | 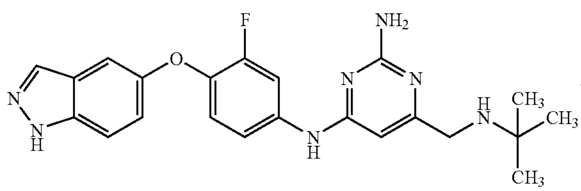 | LC-MS (Method 15): $R_t$ = 1.41 min<br>MS (ESI pos): m/z = 42 (M + H)$^+$ |

Example 127

(2-Amino-6-{[3-fluoro-4-(1H-pyrrolo[2,3-b]pyridin-4-yloxy)phenyl]amino}-pyrimidin-4-yl)methanol

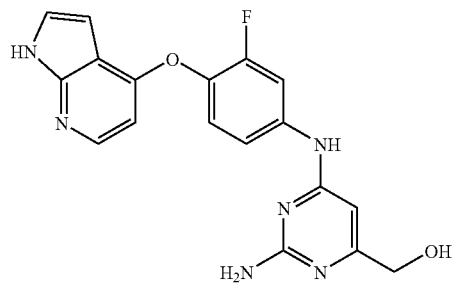

Analogously to example 116, the title compound is obtained by reacting 106 mg (0.44 mmol) of [3-fluoro-4-(1H-pyrrolo[2,3-b]pyridin-4-yloxy)phenyl]amine (from example XIX) with 70 mg (0.44 mmol) of (2-amino-6-chloropyrimidin-4-yl)methanol (from example LXXVIII).

Yield: 49 mg (30% of theory)

LC-MS (Method 14): $R_t$=1.30 min

MS (ESI pos): m/z=367 (M+H)$^+$ $^1$H-NMR (200 MHz, DMSO-d$_6$): δ=4.22 (d, 2H), 5.24 (t, 1H), 6.25 (m, 4H), 6.37 (d, 1H), 7.28 (t, 1H), 7.39 (m, 2H), 8.05 (d, 1H), 8.22 (dd, 1H), 9.42 (s, 1H), 11.71 (s, 1H).

Example 128

Ethyl(2-amino-6-{[3-fluoro-4-(1H-pyrrolo[2,3-b]pyridin-4-yloxy)phenyl]-amino}pyrimidin-4-yl)acetate

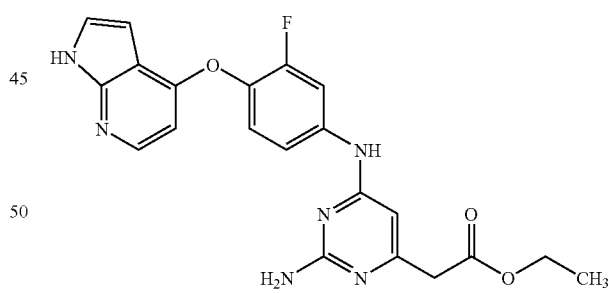

The title compound is synthesized analogously to example 25 from 220 mg (0.908 mmol) of 3-fluoro-4-(1H-pyrrolo[2,3-b]pyridin-4-yloxy)aniline (from example XIX) and 195 mg (0.908 mmol) of ethyl(2-amino-6-chloropyrimidin-4-yl)acetate (from example LXIX).

Yield: 16 mg (4% of theory)

LC-MS (Method 16): $R_t$=1.44 min

MS (ESI pos.): m/z=423 (M+H)$^+$ $^1$H-NMR (DMSO-d$_6$, 400 MHz): δ=1.20 (t, 3H), 3.46 (s, 2H), 4.09 (q, 2H), 6.01 (s, 1H), 6.25 (m, 1H), 6.35 (d, 1H), 6.43 (s, 2H), 7.28 (t, 1H), 7.37 (m, 2H), 8.06 (d, 1H), 8.21 (dd, 1H), 9.46 (s, 1H), 11.74 (s, 1H).

Example 129

N⁴-[3-Fluoro-4-(1H-pyrrolo[2,3-b]pyridin-4-yloxy)phenyl]-6-methylpyrimidine-2,4-diamine

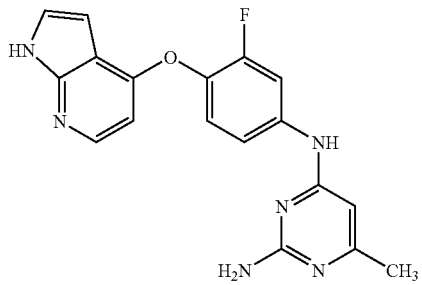

In example 128, the title compound is formed as a byproduct by hydrolysis of the ethyl ester and subsequent decarboxylation.

Yield: 22 mg (7% of theory)
LC-MS (Method 16): $R_t$=1.35 min
MS (ESI pos.): m/z=351 (M+H)⁺
¹H-NMR (DMSO-d₆, 400 MHz): δ=2.12 (s, 3H), 5.90 (s, 1H), 6.26 (m, 1H), 6.32 (s, 2H), 6.34 (d, 1H), 7.27 (t, 1H), 7.36 (m, 2H), 8.06 (d, 1H), 8.21 (dd, 1H), 9.34 (s, 1H), 11.74 (s, 1H).

Example 130

4-(2-Amino-6-{[3-fluoro-4-(1H-pyrrolo[2,3-b]pyridin-4-yloxy)phenyl]amino}-pyrimidin-4-yl)butyric acid

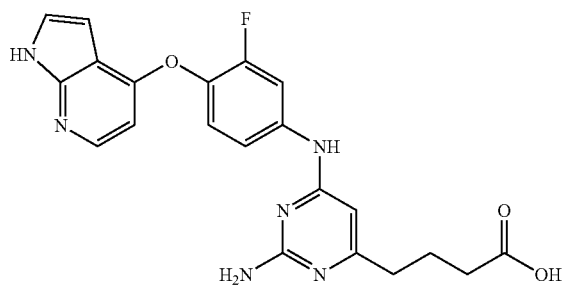

The title compound is synthesized analogously to example 25 from 327 mg (1.34 mmol) of 3-fluoro-4-(1H-pyrrolo[2,3-b]pyridin-4-yloxy)aniline (from example XIX) and 230 mg (1.34 mmol) of 4-(2-amino-6-chloropyrimidin-4-yl)butyric acid (from example LXX) and isolated as the hydrochloride.

Yield: 414 mg (67% of theory)
LC-MS (Method 15): $R_t$=1.15 min
MS (ESI pos.): m/z=423 (M+H)⁺
¹H-NMR (DMSO-d₆, 200 MHz): δ=1.87 (tt, 2H), 2.34 (t, 2H), 2.62 (t, 2H), 4.02 (3H), 6.30 (s, 1H), 6.42 (m, 1H), 6.61 (d, 1H), 7.44-7.61 (m, 3H), 8.24 (d, 1H), 8.25-8.35 (m, 1H), 11.13 (s, 1H), 12.40 (s, 1H), 12.93 (s, 1H).

Example 131

N⁴-[3-Fluoro-4-(1H-pyrrolo[2,3-b]pyridin-4-yloxy)phenyl]-6-(4-oxo-4-piperidin-1-ylbutyl)pyrimidine-2,4-diamine

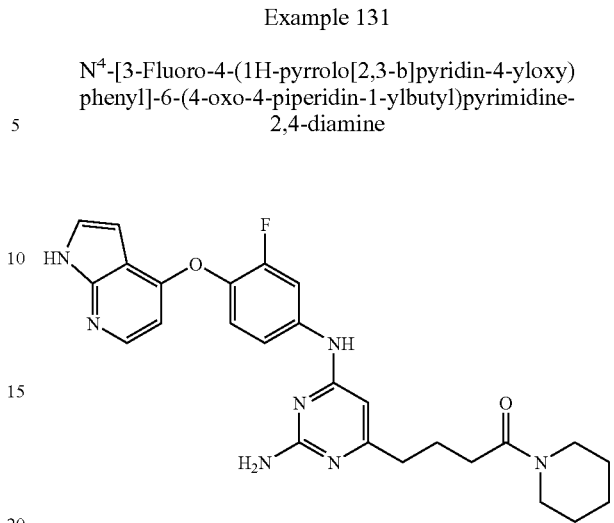

70 mg (0.17 mmol) of 4-(2-amino-6-{[3-fluoro-4-(1H-pyrrolo[2,3-b]pyridin-4-yloxy)phenyl]amino}pyrimidin-4-yl)butyric acid (from example 130) are dissolved in 2.0 ml of DMF, 60 mg (0.16 mmol) of HATU, 23 mg (0.17 mmol) of 1-hydroxy-1H-azobenzotriazole hydrate, 43 mg (0.33 mmol) of diisopropylamine and 28 mg (0.33 mmol) of piperidine are added and the mixture is stirred at RT for 20 hours. Volatile components are removed under reduced pressure and the product is purified by preparative HPLC. The resulting product is purified further by thick-layer chromatography (1 mm silica gel coating, mobile phase: DCM:methanol=9:1).

Yield: 25 mg (31% of theory)
LC-MS (Method 13): $R_t$=1.69 min
MS (ESI pos.): m/z=490 (M+H)⁺
¹H-NMR (DMSO-d₆, 400 MHz): δ=1.40-1.47 (mc, 4H), 1.56 (mc, 2H), 1.82 (tt, 2H), 2.32 (t, 2H), 2.40 (t, 2H), 3.42 (m, 4H), 5.90 (s, 1H), 6.25-6.29 (m, 3H), 6.35 (d, 1H), 7.30 (t, 1H), 7.35 (m, 2H), 8.06 (d, 1H), 8.21 (dd, 1H), 9.33 (s, 1H), 11.74 (s, 1H).

Example 132

Ethyl 4-(2-amino-6-{[3-fluoro-4-(1H-pyrrolo[2,3-b]pyridin-4-yloxy)phenyl]amino}-pyrimidin-4-yl)butanoate

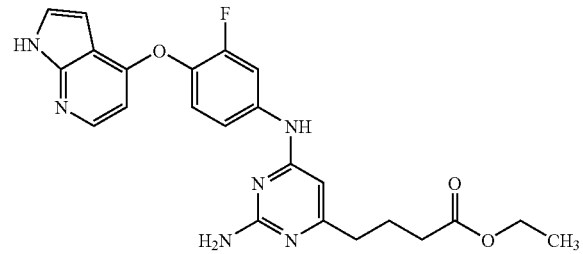

396 mg (0.86 mmol) of 4-(2-amino-6-{[3-fluoro-4-(1H-pyrrolo[2,3-b]pyridin-4-yloxy)phenyl]amino}pyrimidin-4-yl)butyric acid (from example 130) in 20 ml of ethanol are, after addition of 0.10 ml of sulfuric acid, heated under RF for 20 hours. The mixture is concentrated under reduced pressure, dichloromethane and a little methanol are added and the mixture is extracted with sodium bicarbonate solution. The organic phase is dried over sodium sulfate and the solvent is removed under reduced pressure. This gives the title compound.

Yield: 379 mg (95% of theory)
LC-MS (Method 13): $R_t$=1.55 min
MS (ESI pos.): m/z=451 (M+H)$^+$
$^1$H-NMR (DMSO-d$_6$, 400 MHz): δ=1.19 (t, 3H), 1.87 (quint., 2H), 2.04 (t, 2H), 2.59 (t, 2H), 4.07 (q, 2H), 6.13 (br. s, 1H), 6.25 (dd, 1H), 6.38 (d, 1H), 7.31-7.44 (m, 3H), 8.09 (d, 1H), 8.22 (br. s, 1H), 10.51 (br. s, 1H), 11.79 (s, 1H), 12.33 (br. s, 1H).

Example 133

4-(2-Amino-6-{[3-fluoro-4-(1H-pyrrolo[2,3-b]pyridin-4-yloxy)phenyl]amino}-pyrimidin-4-yl)butan-1-ol

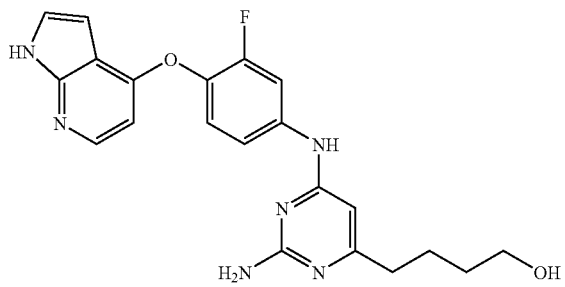

300 mg (0.67 mmol) of 4-(2-amino-6-{[3-fluoro-4-(1H-pyrrolo[2,3-b]pyridin-4-yloxy)phenyl]amino}pyrimidin-4-yl)butan-1-ol (from example 132) are suspended in 15 ml of ethanol, and 253 mg (6.66 mmol) of sodium borohydrate are added a little at a time at RT. The mixture is stirred at RT for 24 hours and then concentrated, and ethyl acetate and water are added. The organic phase is dried over sodium sulfate. The product is purified by column chromatography (silica gel 60; gradient column, mobile phase: DCM:methanol=9:1 to 3:1). 133 mg (27%) of the starting material are recovered. The product fraction is re-purified by preparative HPLC. This gives the title compound.

Yield: 43 mg (16% of theory)
LC-MS (Method 13): $R_t$=1.37 min
MS (ESI neg.): m/z=407 (M−H)$^−$
$^1$H-NMR (DMSO-d$_6$, 400 MHz): δ=1.45 (tt, 2H), 1.62 (tt, 2H), 2.39 (t, 2H), 3.41 (dt, 2H), 4.37 (t, 1H), 5.90 (s, 1H), 6.24-6.26 (m, 1H), 6.27 (br. s, 2H), 6.34 (d, 1H), 7.27 (dd, 1H), 7.34-7.37 (m, 2H), 8.06 (d, 1H), 8.21 (dd, 1H), 9.31 (s, 1H), 11.74 (s, 1H).

Example 134

N$^4$-[3-Fluoro-4-(1H-pyrrolo[2,3-b]pyridin-4-yloxy)phenyl]-6-piperidin-3-ylpyrimidine-2,4-diamine

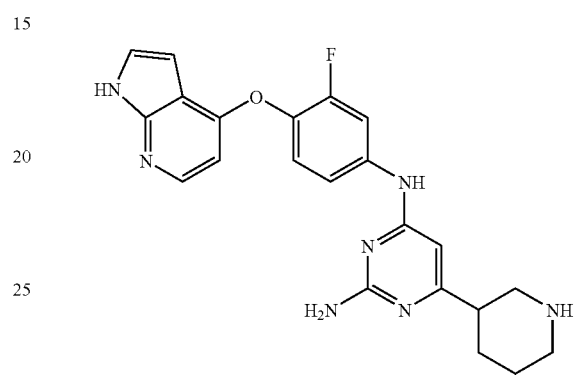

At room temperature, 1.36 g (2.46 mmol) of benzyl 3-(2-amino-6-{[3-fluoro-4-(1H-pyrrolo[2,3-b]pyridin-4-yloxy)phenyl]amino}pyrimidin-4-yl)piperidine-1-carboxylate (from example LXXIV) and 0.4 g of 10% palladium-on-carbon in ethanol are stirred under an atmosphere of hydrogen for 24 hours. The suspension is filtered off with suction through Celite®, and the filtrate is concentrated.

Yield: 0.66 g (60% of theory)
LC-MS (Method 13): $R_t$=1.37 min
MS (ESI neg.): m/z=407 (M−H)$^−$
$^1$H-NMR (DMSO-d$_6$, 300 MHz): δ=1.46-1.70 (m, 4H), 1.89 (m, 1H), 2.57 (m, 1H), 2.67 (t, 1H), 2.97 (m, 1H), 3.10 (m, 1H), 4.07 (br. s, 1H), 5.90 (s, 1H), 6.25 (m, 1H), 6.30 (s, 2H), 6.35 (d, 1H), 7.26 (t, 1H), 7.37 (m, 2H), 8.06 (d, 1H), 8.18 (dd, 1H), 9.35 (s, 1H), 11.71 (s, 1H).

The following compounds are prepared analogously to example 134:

| Ex. No. | Starting materials (Ex. No.) | Structure | MS, HPLC, LC-MS, $^1$H-NMR |
|---|---|---|---|
| 135 | XCI | 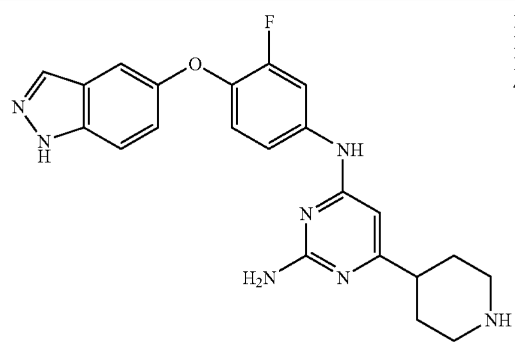 | LC-MS (Method 12): $R_t$ = 2.30 min MS (ESI pos): m/z = 420 (M + H)$^+$ |

-continued

| Ex. No. | Starting materials (Ex. No.) | Structure | MS, HPLC, LC-MS, ¹H-NMR |
|---|---|---|---|
| 136 | LXXV | 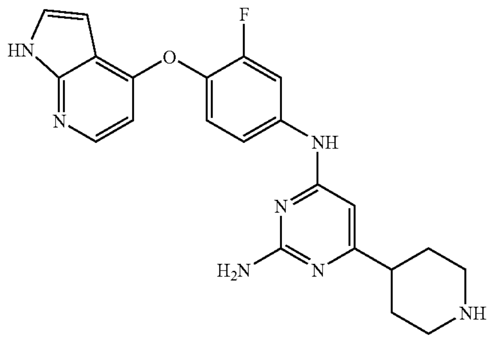 | LC-MS (Method 16): $R_t$ = 1.19 min<br>MS (ESI pos): m/z = 420 (M + H)⁺ |
| 137 | LXXVI | 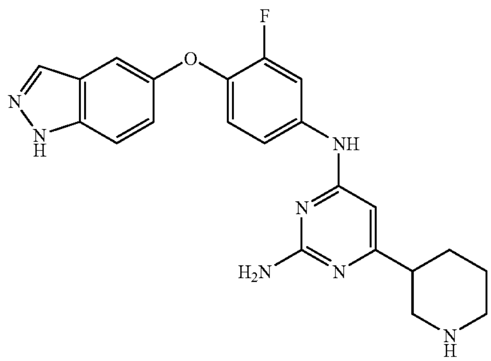 | HPLC (Method 7): $R_t$ = 3.66 min<br>MS (ESI pos): m/z = 420 (M + H)⁺ |
| 138 | LXXVII | 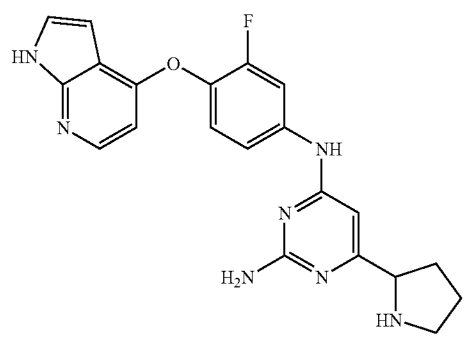 | HPLC (Method 7): $R_t$ = 3.35 min<br>MS (ESI pos): m/z = 406 (M + H)⁺ |

Example 139

6-(1-Acetylpiperidin-3-yl)-N⁴-[3-fluoro-4-(1H-pyrrolo[2,3-b]pyridin-4-yloxy)phenyl]pyrimidine-2,4-diamine

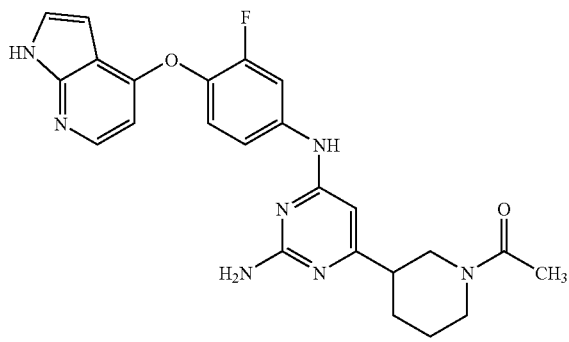

50 mg (0.119 mmol) of N⁴-[3-fluoro-4-(1H-pyrrolo[2,3-b]pyridin-4-yloxy)phenyl]-6-piperidin-3-ylpyrimidine-2,4-diamine (from example 134) are suspended in ethanol. 0.013 ml (0.146 mmol) of acetic anhydride are added, and the mixture is stirred at room temperature for 18 hours. The mixture is then concentrated. The residue is purified by preparative HPLC.

Yield: 24 mg (40% of theory)

HPLC (Method 7): $R_t$=3.58 min

MS (ESI pos.): m/z=462 (M+H)⁺

¹H-NMR (DMSO-d₆, 300 MHz): δ=1.23-1.78 (m, 4H), 1.94 (m, 1H), 2.02 (s, 3H), 2.32 (m, 1H), 2.57 (m, 1H), 2.99 (t, 1H), 3.84 (t, 1H), 4.31 (dd, 0.5H), 4.55 (dd, 0.5H), 5.92 (s, 0.5H), 5.95 (s, 0.5H), 6.25 (m, 1H), 6.30 (s, 2H), 6.35 (d, 1H), 7.26 (t, 1H), 7.37 (m, 2H), 8.06 (d, 1H), 8.19 (dd, 1H), 9.36 (d, 1H), 11.71 (s, 1H).

Example 140

N⁴-[3-Fluoro-4-(1H-pyrrolo[2,3-b]pyridin-4-yloxy)phenyl]-6-(1-isopropylpiperidin-3-yl)pyrimidine-2,4-diamine

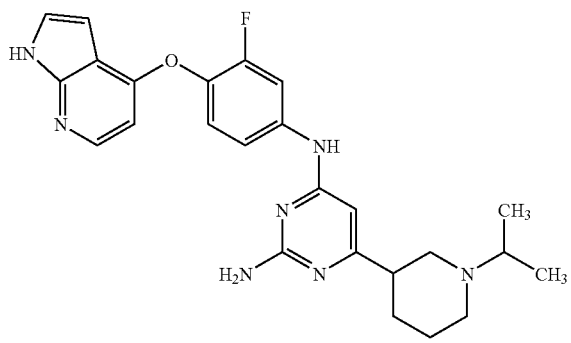

50 mg (0.119 mmol) of N⁴-[3-fluoro-4-(1H-pyrrolo[2,3-b]pyridin-4-yloxy)phenyl]-6-piperidin-3-ylpyrimidine-2,4-diamine (from example 134) are dissolved in DMF. 0.013 ml (0.143 mmol) of 2-bromopropane and 49 mg (0.358 mmol) of potassium carbonate are added, and the mixture is stirred at room temperature for 18 hours. The suspension is filtered off with suction and the filtrate is purified by preparative HPLC.

Yield: 15 mg (27% of theory)
LC-MS (Method 13): $R_f$=1.28 min
MS (ESI neg.): m/z=460.5 (M−H)⁻

Example 141

N⁴-[3-Fluoro-4-(1H-indazol-5-yloxy)phenyl]pyrimidine-2,4-diamine

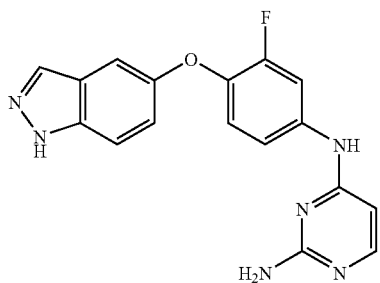

50 mg (0.135 mmol) of 6-chloro-N⁴-[3-fluoro-4-(1H-indazol-5-yloxy)phenyl]pyrimidine-2,4-diamine (from example 8) are dissolved in ethanol. 50 mg of 10% palladium-on-carbon are added, and the suspension is stirred overnight under an atmosphere of hydrogen. The palladium catalyst is filtered off with suction and the filtrate is concentrated.

Yield: 40 mg (70% of theory)
LC-MS (Method 9): $R_f$=1.81 min
MS (ESI pos.): m/z=337.2 (M+H)⁺

Example 142

N⁴-[3-Fluoro-4-(1H-pyrrolo[2,3-b]pyridin-4-yloxy)phenyl]pyrimidine-2,4-diamine

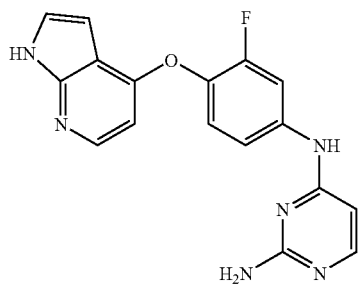

Analogously to example 141, the title compound is obtained by reducing 53 mg (0.14 mmol) of 6-chloro-N⁴-[3-fluoro-4-(1H-pyrrolo[2,3-b]pyridin-4-yloxy)phenyl]-pyrimidine-2,4-diamine (from example 60).

Yield: 16 mg (32% of theory)
LC-MS (Method 16): $R_f$=1.30 min
MS (ESI neg.): m/z=335 (M−H)⁻
¹H-NMR (DMSO-d₆, 300 MHz): δ=6.02 (d, 1H), 6.25 (dd, 1H), 6.32 (br. s, 2H), 6.35 (d, 1H), 7.27 (t, 1H), 7.34-7.40 (m, 2H), 7.86 (d, 1H), 8.06 (d, 1H), 8.21 (dd, 1H), 9.39 (s, 1H), 11.72 (s, 1H).

B. ASSESSMENT OF THE PHYSIOLOGICAL ACTIVITY

The inhibition of the enzyme is investigated in an in vitro assay with recombinant Rho kinase II. The vessel-relaxing action is determined using phenylephrin-induced contractions of isolated rings of the saphenous artery of rabbits. The suitability of the compounds according to the invention for treating cardiovascular disorders can be demonstrated by examining the hypotensive effect on anesthetized rats.

Inhibition of Recombinant Rho Kinase II (ROKα)

The activity of Rho kinase is determined by the uptake of ³³P phosphate into a substrate peptide. To this end, commercially available Rho kinase II (Upstate Biotechnology) is pre-incubated at 37° C. in the presence of the S6 phosphate-acceptor peptide with the test substances or a solvent control for 10 min. The kinase reaction is then started by addition of ³³P-labelled ATP. After 20 min at 37° C., the reaction is stopped by addition of H₃PO₄. Aliquots are pipetted onto filters and the filters are washed and then covered with scintillator. The radioactivity of the ³³P-labelled peptides bound to the filter is measured in a Micro-Beta counter. The IC₅₀ value corresponds to the concentration of a test substance at which the Rho-kinase-catalysed uptake of ³³P into the peptide is inhibited by 50%, compared to a solvent control. The experimental data are summarized in the table below.

| Example No. | IC₅₀ (nM) |
| --- | --- |
| 1 | 680 |
| 5 | 20 |
| 6 | 30 |
| 7 | 100 |
| 11 | 6 |

-continued

| Example No. | IC$_{50}$ (nM) |
|---|---|
| 12 | 55 |
| 13 | 9 |
| 15 | 20 |
| 16 | 50 |
| 18 | 43 |
| 19 | 2 |
| 68 | 1 |
| 134 | 2 |

Vessel-Relaxing Action In Vitro

Individual 3-mm-wide rings of the isolated saphenous artery of rabbits are introduced into 5 ml organ baths with Krebs-Henseleit solution (37° C., gassed with carbogen). The vessel tone is monitored isometrically and registered. Contractions are induced by addition of $3 \times 10^{-8}$ g of phenylephrin/ml, which is washed out again after 4 min. After a number of control cycles, the rings are pre-incubated with the substance to be examined, with the dosage being increased for each further cycle, and the subsequent contraction is compared to the intensity of the last control contraction. The concentration required to reduce the intensity of the control value by 50% (IC$_{50}$) is calculated. The experimental data are summarized in the table below.

| Example No. | IC$_{50}$ (nM) |
|---|---|
| 1 | 6800 |
| 5 | 1020 |
| 6 | 4330 |
| 7 | 6700 |
| 11 | 350 |
| 12 | 2700 |
| 13 | 2000 |
| 16 | 6900 |
| 19 | 350 |
| 68 | 260 |
| 116 | 150 |
| 117 | 80 |

Measurement of Blood Pressure in Anesthetized Rats

Male Wistar rats of a body weight of 300-350 g are anesthetized with thiopental (100 mg/kg i.p.). Following tracheotomy, a catheter is introduced into the femoral artery to measure the blood pressure. The substances to be tested are administered as solutions, either orally via a stomach tube or intravenously via the femoral vein.

C. WORKING EXAMPLES FOR PHARMACEUTICAL COMPOSITIONS

The compounds according to the invention can be converted into pharmaceutical preparations as follows:

Tablet:

Composition:

100 mg of the compound from Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg. Diameter 8 mm, spherical radius 12 mm.

Preparation:

The mixture of inventive compound, lactose and starch is granulated with a 5% strength solution (w/w) of the PVP in water. After drying, the granules are mixed for 5 min with the magnesium stearate. This mixture is compacted in a conventional tablet press (dimensions of the tablet: see above). The standard value used for compacting is a compaction force of 15 kN.

Suspension for Oral Administration:

Composition:

1000 mg of the compound from Example 1, 1000 mg of ethanol (96%), 400 mg of Rhodigel (xanthan gum from FMC, Pennsylvania, USA) and 99 g of water.

A single dose of 100 mg of the compound according to the invention corresponds to 10 ml of oral suspension.

Preparation:

The Rhodigel is suspended in ethanol and the active compound is added to the suspension. The water is added with stirring. The mixture is stirred for about 6 h until the Rhodigel is completely swollen.

The invention claimed is:

1. A compound of the formula

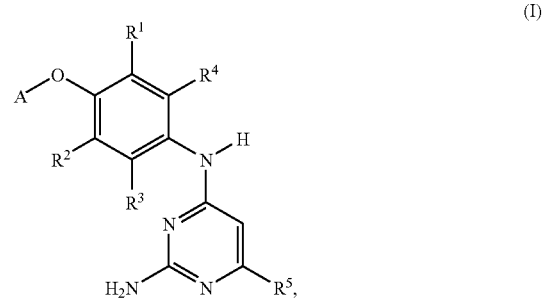

(I)

in which

A represents a radical

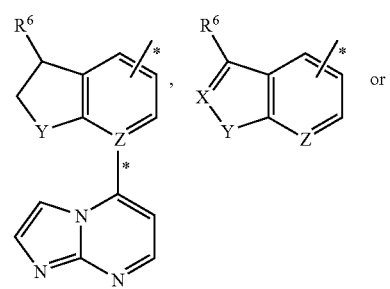

in which

X represents N or C—H,

Y represents N—R$^7$, O or S in which

R$^7$ represents hydrogen, benzyl, phenyl, (C$_1$-C$_6$)-alkyl or (C$_3$-C$_8$)-cycloalkyl, where alkyl and cycloalkyl for their part may be substituted by fluorine, hydroxyl, amino, carboxyl, (C$_1$-C$_6$)-alkoxy, (C$_1$-C$_6$)-alkylamino or morpholinyl, Z represents N or C—H, R$^6$ represents hydrogen, halogen, trifluoromethyl, ($C_1$-$C_6$)-alkylamino or W—R$^7$, in which W represents NH, O or a bond, R$^7$ is as defined above and

* denotes the point of attachment to the phenolic oxygen,

R$^1$ and R$^2$ independently of one another represent hydrogen, halogen or cyano, R$^3$ and R$^4$ independently of one another represent hydrogen, fluorine or chlorine, R$^5$ represents a radical selected from the group consisting of:

hydrogen, hydroxyl, halogen, trifluoromethyl, ($C_3$-$C_8$)-cycloalkyl, ($C_1$-$C_6$)-alkyl, ($C_1$-$C_6$)-alkoxy, where cycloalkyl, alkyl and alkoxy for their part may be substituted by hydroxyl, carboxyl, ($C_1$-$C_6$)-alkoxy, ($C_1$-$C_6$)-alkoxycarbonyl, ($C_6$-$C_{10}$)-aryl, NR$^8$R$^9$ or C(=O)NR$^8$R$^9$, in which R$^8$ and R$^9$ independently of one another represent hydrogen, ($C_1$-$C_8$)-alkyl, optionally ($C_1$-$C_6$)-alkyl-substituted ($C_3$-$C_6$)-cycloalkyl, optionally halogen-substituted ($C_6$-$C_{10}$)-aryl or 5- to 10-membered heteroaryl or R$^8$ and R$^9$ together with the nitrogen atom to which they are attached form a 5- or 6-membered heterocycle which may contain a further heteroatom O or N in the ring and which may be substituted by ($C_1$-$C_6$)-alkyl, ($C_1$-$C_6$)-alkanoyl or ($C_1$-$C_6$)-alkoxycarbonyl, ($C_6$-$C_{10}$)-aryl, ($C_6$-$C_{10}$)-aryloxy, 5- to 10-membered heteroaryl, 5- to 10-membered heteroaryloxy, 5- to 10-membered heterocyclyl which is attached via a carbon atom, where aryl, aryloxy, heteroaryl, heteroaryloxy and heterocyclyl for their part may be substituted by halogen, cyano, nitro, carboxyl, amino, trifluoromethyl, optionally hydroxyl-substituted ($C_1$-$C_6$)-alkyl, ($C_1$-$C_6$)-alkoxy, ($C_1$-$C_6$)-alkylamino, ($C_1$-$C_6$)-alkanoyl, ($C_1$-$C_6$)-alkoxycarbonyl, ($C_1$-$C_6$)-alkanoylamino, ($C_1$-$C_6$)-alkoxycarbonylamino or 5- or 6-membered heterocyclyl,

NR$^{10}$R$^{11}$ in which

R$^{10}$ and R$^{11}$ independently of one another represent hydrogen, ($C_1$-$C_6$)-alkyl, ($C_3$-$C_8$)-cycloalkyl, ($C_6$-$C_{10}$)-aryl or 5- to 10-membered heteroaryl, where alkyl and cycloalkyl for their part may be substituted by hydroxyl, ($C_1$-$C_6$)-alkoxy, ($C_6$-$C_{10}$)-aryl, 5- to 10-membered heteroaryl or NR$^{15}$R$^{16}$, in which R$^{15}$ and R$^{16}$ independently of one another represent hydrogen, ($C_1$-$C_6$)-alkyl, ($C_3$-$C_6$)-cycloalkyl, ($C_6$-$C_{10}$)-aryl or 5- or 6-membered heteroaryl or R$^{15}$ and R$^{16}$ together with the nitrogen atom to which they are attached form a 5- or 6-membered heterocycle which may contain a further heteroatom O or N in the ring and which may be substituted by ($C_1$-$C_6$)-alkyl, ($C_1$-$C_6$)-alkanoyl or ($C_1$-$C_6$)-alkoxycarbonyl, and aryl and heteroaryl for their part may be substituted by halogen, hydroxyl, amino, cyano, trifluoromethyl, ($C_1$-$C_6$)-alkyl, ($C_1$-$C_6$)-alkoxy, ($C_1$-$C_6$)-alkylamino or ($C_1$-$C_6$)-alkanoylamino, or R$^{10}$ and R$^{11}$ together with the nitrogen atom to which they are attached form a 4- to 6-membered heterocycle which may contain a further heteroatom O or N in the ring and which may be substituted by fluorine, hydroxyl, carboxyl, 5- to 7-membered heterocyclyl which may contain one or two further heteroatoms N and/or O in the ring and which for its part may be substituted by ($C_1$-$C_4$)-alkyl or ($C_1$-$C_4$)-alkoxycarbonyl, ($C_1$-$C_4$)-alkoxy, optionally hydroxyl-, ($C_1$-$C_4$)-alkoxy- or NR$^{17}$R$^{18}$-substituted ($C_1$-$C_4$)-alkyl, ($C_1$-$C_4$)-alkanoyl, ($C_1$-$C_4$)-alkoxycarbonyl or NR$^{12}$R$^{13}$, where R$^{12}$ and R$^{13}$ independently of one another represent hydrogen, ($C_1$-$C_6$)-alkyl, ($C_1$-$C_4$)-alkoxycarbonyl, ($C_3$-$C_8$)-cycloalkyl or ($C_1$-$C_4$)-alkanoyl or R$^{12}$ and R$^{13}$ together with the nitrogen atom to which they are attached form a 5- or 6-membered heterocycle which may contain a further heteroatom O or N in the ring and which may be substituted by ($C_1$-$C_6$)-alkyl, ($C_1$-$C_6$)-alkanoyl or ($C_1$-$C_6$)-alkoxycarbonyl, and R$^{17}$ and R$^{18}$ independently of one another represent hydrogen, optionally hydroxyl-substituted ($C_1$-$C_6$)-alkyl, ($C_3$-$C_6$)-cycloalkyl, ($C_6$-$C_{10}$)-aryl or 5- or 6-membered heteroaryl or R$^{17}$ and R$^{18}$ together with the nitrogen atom to which they are attached form a 5- or 6-membered heterocycle which may contain a further heteroatom O or N in the ring and which may be substituted by ($C_1$-$C_6$)-alkyl, ($C_1$-$C_6$)-alkanoyl or ($C_1$-$C_6$)-alkoxycarbonyl, or R$^{10}$ and R$^{11}$ together with the nitrogen atom to which they are attached form a 7- to 12-membered bicyclic or tricyclic heterocycle which is fused or spirocyclic and which may have one or two further heteroatoms from the group consisting of N and O in the ring and which may be substituted by fluorine, ($C_1$-$C_4$)-alkyl, ($C_1$-$C_4$)-alkoxycarbonyl, ($C_1$-$C_4$)-alkanoyl or benzyl, and C(=O)R$^{14}$, in which R$^{14}$ represents ($C_1$-$C_6$)-alkoxy, ($C_1$-$C_6$)-alkylamino or a 5- to 10-membered mono- or bicyclic heterocycle which is attached via a nitrogen atom, which is fused or spirocyclic and which may have one or two further heteroatoms from the group consisting of N and O in the ring, where alkylamino for its part may be substituted by a 5- or 6-membered heterocycle, or a salt thereof.

2. The compound as claimed in claim 1
in which
A represents a radical

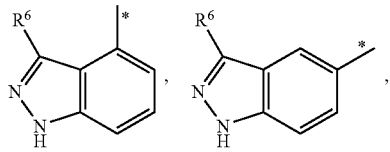

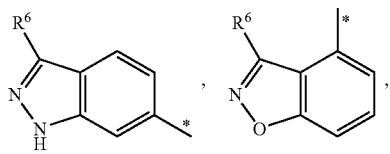

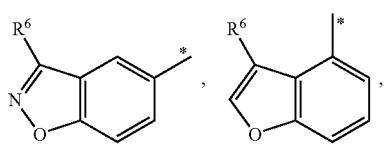

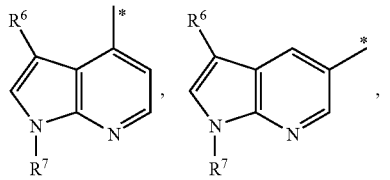

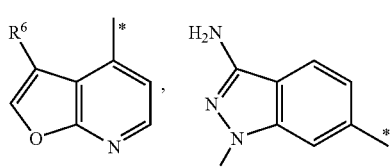

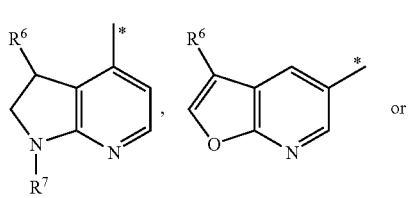

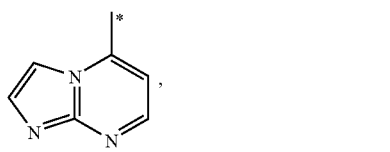

in which
$R^6$ represents hydrogen, $(C_1-C_4)$-alkyl or NH—$R^7$,
$R^7$ represents hydrogen or $(C_1-C_4)$-alkyl
and
\* denotes the point of attachment to the phenolic oxygen,
$R^1$ and $R^2$ independently of one another represent hydrogen, fluorine or chlorine,
$R^3$ and $R^4$ independently of one another represent hydrogen or fluorine,
$R^5$ represents a radical selected from the group consisting of:
hydrogen, chlorine, $(C_3-C_8)$-cycloalkyl, $(C_1-C_6)$-alkyl, $(C_1-C_6)$-alkoxy,
where alkyl and alkoxy for their part may be substituted by hydroxyl, carboxyl, $(C_1-C_4)$-alkoxy, $(C_1-C_4)$-alkoxycarbonyl, $NR^8R^9$ or $C(=O)NR^8R^9$,
in which
$R^8$ and $R^9$ independently of one another represent hydrogen, $(C_1-C_8)$-alkyl, optionally $(C_1-C_4)$-alkyl-substituted $(C_3-C_6)$-cycloalkyl, optionally halogen-substituted phenyl or 5- or 6-membered heteroaryl
or
$R^8$ and $R^9$ together with the nitrogen atom to which they are attached form a morpholine, piperazine, piperidine or pyrrolidine ring, where the rings for their part may be substituted by $(C_1-C_4)$-alkyl,
$(C_6-C_{10})$-aryl, 5- or 6-membered heteroaryl, 5- or 6-membered heterocyclyl which is attached via a carbon atom,
where aryl, heteroaryl and heterocyclyl for their part may be substituted by halogen, cyano, nitro, carboxyl, amino, trifluoromethyl, optionally hydroxyl-substituted $(C_1-C_4)$-alkyl, $(C_1-C_4)$-alkoxy, $(C_1-C_4)$-alkylamino, $(C_1-C_4)$-alkanoyl, $(C_1-C_4)$-alkoxycarbonyl, $(C_1-C_4)$-alkanoylamino, $(C_1-C_4)$-alkoxycarbonylamino or 6-membered heterocyclyl,
$NR^{10}R^{11}$
in which
$R^{10}$ and $R^{11}$ independently of one another represent hydrogen, $(C_1-C_6)$-alkyl, $(C_3-C_8)$-cycloalkyl, phenyl or 5- or 6-membered heteroaryl,
where alkyl and cycloalkyl for their part may be substituted by hydroxyl, $(C_1-C_4)$-alkoxy, phenyl, 5- or 6-membered heteroaryl or $NR^{15}R^{16}$,
in which
$R^{15}$ and $R^{16}$ independently of one another represent hydrogen, $(C_1-C_4)$-alkyl, $(C_3-C_6)$-cycloalkyl, phenyl or 5- or 6-membered heteroaryl
or
$R^{15}R^{16}$ together with the nitrogen atom to which they are attached form a morpholine, piperazine, piperidine or pyrrolidine ring, where the rings for their part may be substituted by $(C_1-C_4)$-alkyl,
and
phenyl and heteroaryl for their part may be substituted by fluorine, chlorine, hydroxyl, amino, cyano, trifluoromethyl, $(C_1-C_4)$-alkyl, $(C_1-C_4)$-alkoxy, $(C_1-C_4)$-alkylamino or $(C_1-C_4)$-alkanoylamino,
or
$R^{10}$ and $R^{11}$ together with the nitrogen atom to which they are attached form a 4- to 6-membered heterocycle which may contain a further heteroatom O or N in the ring and which may be substituted by fluorine, hydroxyl, carboxyl, 5- to 7-membered heterocyclyl which may contain one or two further heteroatoms N and/or O in the ring and which for its part may be substituted by $(C_1-C_4)$-alkyl or $(C_1-C_4)$-alkoxycarbonyl, $(C_1-C_4)$-alkoxy, optionally hydroxyl-, $(C_1-C_4)$- alkoxy- or $NR^{17}R^{18}$-substituted $(C_1-C_4)$-alkyl, $(C_1-C_4)$-alkanoyl, $(C_1-C_4)$-alkoxycarbonyl or $NR^{12}R^{13}$,
where
$R^{12}$ and $R^{13}$ independently of one another represent hydrogen or $(C_1-C_4)$-alkyl
or
$R^{12}$ and $R^{13}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl,
and
$R^{17}$ and $R^{18}$ independently of one another represent hydrogen, optionally hydroxyl-substituted $(C_1-C_4)$-alkyl or phenyl
or
$R^{17}$ and $R^{18}$ together with the nitrogen atom to which they are attached form a pyrrolidine ring,
or
$R^{10}$ and $R^{11}$ together with the nitrogen atom to which they are attached form a 7- to 12-membered bicyclic or tricyclic heterocycle which is fused or spirocyclic, which may have one or two further hetero atoms from the group consisting of N and O in the ring and which may be substituted by $(C_1-C_4)$-alkyl, $(C_1-C_4$-alkoxycarbonyl, $(C_1-C_4)$-alkanoyl or benzyl,
and $C(=O)R^{14}$
in which
$R^{14}$ represents $(C_1-C_6)$-alkoxy, $(C_1-C_6)$-alkylamino or a 5- to 10-membered mono- or bicyclic heterocycle which is attached via a nitrogen atom, which is fused or spirocyclic and which may have one or two further heteroatoms from the group consisting of N and O in the ring,
where alkylamino for its part may be substituted by a 5- or 6-membered heterocyclyl, or a salt thereof.

3. The compound as claimed in claim 1
in which
A represents a radical $R^6$ or $R^6$ in which
$R^6$ represents hydrogen or methyl
and
\* denotes the point of attachment to the phenolic oxygen,
$R^1$ and $R^2$ independently of one another represent hydrogen, fluorine or chlorine,
$R^3$ and $R^4$ represent hydrogen,
$R^5$ represents a radical selected from the group consisting of:
hydrogen, chlorine, cyclohexyl, $(C_1-C_4)$-alkyl, $(C_1-C_4)$-alkoxy,
where alkyl and alkoxy for their part may be substituted by hydroxyl, carboxyl, $(C_1-C_4)$-alkoxy, methyloxycarbonyl, ethyloxycarbonyl, $NR^8R^9$ or $C(=O)NR^8R^9$,
in which
$R^8$ and $R^9$ independently of one another represent hydrogen, $(C_1-C_8)$-alkyl, cyclopropyl, optionally methyl-substituted cyclopentyl or optionally fluorine-substituted phenyl
or
$R^8$ and $R^9$ together with the nitrogen atom to which they are attached form a piperidine, 2-methylpiperidine or 2,6-dimethylpiperidine ring,
phenyl, pyridyl, pyrrolyl, piperidin-3-yl, piperidin-4-yl, pyrrolidin-2-yl,
where phenyl, pyridyl and pyrrolyl for their part may be substituted by fluorine, chlorine, bromine, cyano, nitro, trifluoromethyl, methyl, hydroxymethyl, methoxy, dimethylamino or morpholinyl,
and
piperidin-3-yl, piperidin-4-yl and pyrrolidin-2-yl for their part may be substituted by methyl, ethyl, n-propyl, isopropyl, methylcarbonyl or ethylcarbonyl,
$NR^{10}R^{11}$
in which
$R^{10}$ and $R^{11}$ independently of one another represent hydrogen, $(C_1-C_4)$-alkyl, 3-hydroxypropyl, 2-hydroxycyclohexyl, 2-aminocyclohexyl, phenyl, pyridyl or pyrazolyl,
where phenyl and pyridyl for their part may be substituted by chlorine, hydroxyl, amino, cyano, methyl or methoxy,
or
$R^{10}$ and $R^{11}$ together with the nitrogen atom to which they are attached form a piperazine, 3-methylpiperazine, 3,5-dimethylpiperazine, 4-isobutylpiperazine, morpholine, pyrrolidine, 3-aminopyrrolidine, 3-methylaminopyrrolidine, 3-(N,N-dimethylamino)pyrrolidine, 2-aminomethylpyrrolidine, 3-hydroxypyrrolidine, 2-hydroxymethylpyrrolidine or 2-methoxymethylpyrrolidine ring or a radical -continued

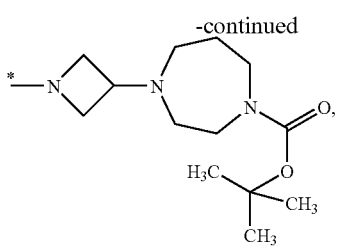

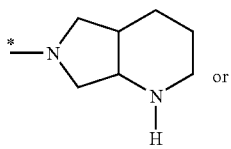 or

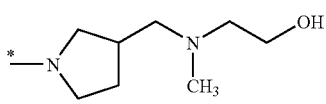

in which

* denotes the point of attachment to the pyrimidine ring, and C(=O)$R^{14}$ in which $R^{14}$ represents methoxy, piperidinyl-N-ethylamino, piperidinyl or piperazinyl, or a salt thereof.

4. A process for preparing compounds as defined in claim 1, characterized in that either

[A] compounds of the formula (II)

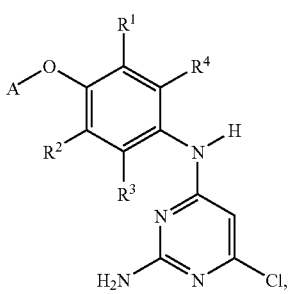

(II)

in which

A, $R^1$, $R^2$, $R^3$ and $R^4$ are as defined in claim 1 are reacted with compounds of the formula (III)

$R^5$—$X^1$ (III), in which $R^5$ is as defined in claim 1 and $X^1$ represents hydrogen, B(OH)$_2$ or a boronic acid ester such as

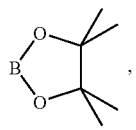, or

[B] compounds of the formula (IV)

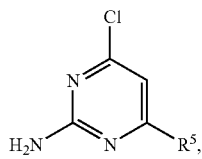

(IV)

in which $R^5$ is as defined in claim 1 are reacted with compounds of the formula (V)

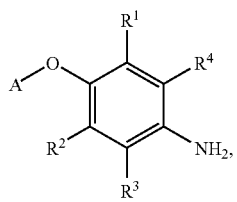

(V)

in which

A, $R^1$, $R^2$, $R^3$ and $R^4$ are as defined in claim 1.

5. A pharmaceutical composition comprising a compound as defined in claim 1 in combination with an inert nontoxic pharmaceutically acceptable auxiliary.

6. A method for the treatment of erectile dysfunction in a human or animal, comprising administering to said human or animal, a cardiovascularly effective amount of a compound as defined in claim 1.

* * * * *